(12) United States Patent
Monaghan et al.

(10) Patent No.: US 12,427,474 B2
(45) Date of Patent: Sep. 30, 2025

(54) SYSTEM AND METHOD FOR CONCENTRATING GAS

(71) Applicant: INVACARE CORPORATION, Elyria, OH (US)

(72) Inventors: Matthew E. Monaghan, Chagrin Falls, OH (US); Pankaj Patil, Wooster, OH (US)

(73) Assignee: VENTEC LIFE SYSTEMS, INC., Bothell, WA (US)

(*) Notice: Subject to any disclaimer, the term of this patent is extended or adjusted under 35 U.S.C. 154(b) by 410 days.

(21) Appl. No.: 17/376,241

(22) Filed: Jul. 15, 2021

(65) Prior Publication Data

US 2022/0016564 A1 Jan. 20, 2022

Related U.S. Application Data

(60) Provisional application No. 63/212,920, filed on Jun. 21, 2021, provisional application No. 63/052,694, filed on Jul. 16, 2020.

(51) Int. Cl.
*B01D 53/02* (2006.01)
*B01D 53/04* (2006.01)
(Continued)

(52) U.S. Cl.
CPC ....... *B01D 53/229* (2013.01); *B01D 53/0407* (2013.01); *B01D 53/0446* (2013.01);
(Continued)

(58) Field of Classification Search
CPC .......... A61M 16/101; A61M 2205/276; B01D 2053/223; B01D 2253/108;
(Continued)

(56) References Cited

U.S. PATENT DOCUMENTS 3,494,296 A 2/1970 Gluntz
3,602,527 A 8/1971 Goetz
(Continued)

FOREIGN PATENT DOCUMENTS

AU 1999015998 A 8/1999
AU 200072682 A1 5/2001
(Continued)

OTHER PUBLICATIONS

US 6,979,301 B2, 12/2005, Van Brunt et al. (withdrawn)
(Continued)

*Primary Examiner* — Christopher P Jones
(74) *Attorney, Agent, or Firm* — Calfee, Halter & Griswold LLP

(57) ABSTRACT

Systems and methods are provided that obtain the same or better level of performance by using lower operating flow rates, pressures and/or optimized flow distributions within the system. This extends the life of system components and lower energy consumption. In one embodiment, gas separation (or sieve) beds that are used to separate gaseous components are provided that have lower flow and pressure requirements compared to conventional beds. The sieve beds include, for example, a diffuser having low solid area in cross-section and maximum open area for flow while providing adequate mechanical properties to contain sieve material and support filter media. In another embodiment, systems and methods are provided having an indicator when a component has been serviced or repaired. This provides an indication whether the component has been tampered with in any manner. This allows the manufacturer to determine if the component was serviced, repaired, or tampered with outside the manufacturer's domain.

20 Claims, 30 Drawing Sheets

(51) Int. Cl.
*B01D 53/047* (2006.01)
*B01D 53/22* (2006.01)
*B01D 69/04* (2006.01)
*B01D 71/02* (2006.01)

(52) U.S. Cl.
CPC ......... *B01D 53/047* (2013.01); *B01D 53/226* (2013.01); *B01D 69/046* (2013.01); *B01D 71/0281* (2022.08); *B01D 2053/223* (2013.01); *B01D 2256/12* (2013.01); *B01D 2257/102* (2013.01); *B01D 2259/4533* (2013.01)

(58) Field of Classification Search
CPC .......... B01D 2256/12; B01D 2257/102; B01D 2259/4533; B01D 2259/4541; B01D 39/06; B01D 53/0407; B01D 53/0415; B01D 53/0446; B01D 53/047; B01D 53/053; B01D 53/226; B01D 53/229; B01D 69/046; B01D 71/0281
See application file for complete search history.

(56) References Cited

U.S. PATENT DOCUMENTS

| | | |
|---|---|---|
| 3,608,833 A | 9/1971 | Hankins |
| 3,964,519 A | 6/1976 | De Baun |
| 4,127,395 A | 11/1978 | McKey et al. |
| 4,144,037 A | 3/1979 | Armond et al. |
| 4,247,311 A | 1/1981 | Seibert |
| 4,378,982 A | 4/1983 | Mcombs |
| 4,449,990 A | 5/1984 | Tedford |
| 4,454,596 A | 6/1984 | Wunsch et al. |
| 4,561,287 A | 12/1985 | Rowland |
| 4,575,042 A | 3/1986 | Grimland |
| 4,648,888 A | 3/1987 | Rowland |
| 4,826,510 A | 5/1989 | McCombs |
| 4,832,711 A | 5/1989 | Christel, Jr. et al. |
| 4,932,402 A | 6/1990 | Snook et al. |
| 4,971,609 A | 11/1990 | Pawlos |
| 5,057,822 A | 10/1991 | Hoffman |
| 5,099,837 A | 3/1992 | Russel et al. |
| 5,101,656 A | 4/1992 | Miller |
| 5,144,945 A | 9/1992 | Nishino et al. |
| 5,258,056 A | 11/1993 | Shirley et al. |
| 5,294,049 A | 3/1994 | Trunkle et al. |
| 5,298,226 A | 3/1994 | Nowobilski |
| 5,469,372 A | 11/1995 | McBrearty et al. |
| 5,474,595 A | 12/1995 | McCombs |
| 5,538,544 A | 7/1996 | Nowobilski |
| 5,593,478 A | 1/1997 | Hill et al. |
| 5,626,131 A | 5/1997 | Chua et al. |
| 5,680,409 A | 10/1997 | Qin et al. |
| 5,720,276 A | 2/1998 | Kobatake et al. |
| 5,779,773 A | 7/1998 | Cam et al. |
| 5,785,681 A | 7/1998 | Indravudh |
| 5,906,672 A | 5/1999 | Michaels et al. |
| 5,917,135 A | 6/1999 | Michaels et al. |
| 5,931,160 A | 8/1999 | Gilmore et al. |
| 5,983,416 A | 11/1999 | Idland |
| 5,988,165 A | 11/1999 | Richey, II et al. |
| 6,022,634 A | 2/2000 | Ramunni |
| 6,051,051 A | 4/2000 | Hees et al. |
| 6,106,245 A | 8/2000 | Cabuz |
| 6,139,426 A | 10/2000 | Koerber |
| 6,151,586 A | 11/2000 | Brown |
| 6,152,134 A | 11/2000 | Webber et al. |
| 6,266,995 B1 | 7/2001 | Scott |
| 6,279,377 B1 | 8/2001 | Cao |
| 6,427,690 B1 | 8/2002 | McCombs et al. |
| 6,442,433 B1 | 8/2002 | Linberg |
| 6,472,988 B1 | 10/2002 | Feld et al. |
| 6,517,610 B1 | 2/2003 | La Houssaye |
| 6,520,176 B1 | 2/2003 | Dubois et al. |
| 6,561,187 B2 | 5/2003 | Schmidt et al. |
| 6,629,525 B2 | 10/2003 | Hill et al. |
| 6,651,658 B1 | 11/2003 | Hill et al. |
| 6,691,702 B2 | 2/2004 | Appel et al. |
| 6,764,534 B2 | 7/2004 | McCombs et al. |
| 6,837,244 B2 | 1/2005 | Yagi et al. |
| 6,878,186 B2 | 4/2005 | Neary |
| 6,949,133 B2 | 9/2005 | McCombs et al. |
| 6,962,654 B2 | 11/2005 | Arnaud |
| 7,036,729 B2 | 5/2006 | Chung |
| 7,115,104 B2 | 10/2006 | Van Brunt et al. |
| 7,278,983 B2 | 10/2007 | Ireland et al. |
| 7,294,170 B2 | 11/2007 | Richey, II et al. |
| 7,306,657 B2 | 12/2007 | Yagi et al. |
| 7,316,733 B1 | 1/2008 | Hedrick et al. |
| 7,329,304 B2 | 2/2008 | Bliss et al. |
| 7,331,340 B2 | 2/2008 | Barney |
| 7,393,382 B2 | 7/2008 | Givens |
| 7,425,203 B2 | 9/2008 | Van Brunt et al. |
| 7,431,032 B2 | 10/2008 | Jagger et al. |
| 7,445,663 B1 | 11/2008 | Hunter et al. |
| 7,455,717 B2 | 11/2008 | Sprinkle |
| 7,491,182 B2 | 2/2009 | Van Brunt |
| 7,505,374 B2 | 3/2009 | Booty, Jr. et al. |
| 7,552,731 B2 | 6/2009 | Jorczak et al. |
| 7,604,004 B2 | 10/2009 | Jagger et al. |
| 7,604,005 B2 | 10/2009 | Jagger et al. |
| 7,652,571 B2 | 1/2010 | Parkulo et al. |
| 7,662,638 B2 | 2/2010 | Dadala et al. |
| 7,686,870 B1 | 3/2010 | Deane et al. |
| 7,722,698 B2 | 5/2010 | Thompson et al. |
| 7,722,700 B2 | 5/2010 | Sprinkle |
| 7,753,996 B1 | 7/2010 | Deane et al. |
| 7,766,010 B2 | 8/2010 | Jagger et al. |
| 7,794,522 B2 | 9/2010 | Bliss et al. |
| 7,826,728 B2 | 11/2010 | Konno et al. |
| 7,866,315 B2 | 1/2011 | Jagger et al. |
| 7,875,105 B2 | 1/2011 | Chambers et al. |
| 7,922,789 B1 | 4/2011 | Deane et al. |
| 7,931,197 B2 | 4/2011 | Brandt et al. |
| 8,013,739 B2 | 9/2011 | Parkulo et al. |
| 8,062,003 B2 | 11/2011 | Goertzen et al. |
| 8,070,853 B2 | 12/2011 | Sprinkle |
| 8,092,396 B2 | 1/2012 | Bagha et al. |
| 8,231,541 B2 | 7/2012 | Colquitt et al. |
| 8,262,771 B2 | 9/2012 | Seki et al. |
| 8,366,402 B2 | 2/2013 | St. Michel |
| 8,366,815 B2 | 2/2013 | Taylor et al. |
| 8,377,181 B2 | 2/2013 | Taylor et al. |
| 8,388,745 B1 | 3/2013 | Pelletier et al. |
| 8,421,465 B2 | 4/2013 | Carter |
| 8,547,062 B2 | 10/2013 | Carter et al. |
| 8,568,519 B2 | 10/2013 | Taylor et al. |
| 8,599,016 B2 | 12/2013 | Parkulo et al. |
| 8,668,767 B2 | 3/2014 | Sprinkle et al. |
| 8,677,998 B2 | 3/2014 | Yamaura et al. |
| 8,726,744 B2 | 5/2014 | Alburty et al. |
| 8,818,824 B2 | 8/2014 | DeBusk et al. |
| 8,956,289 B2 | 2/2015 | Kitajima et al. |
| 9,058,741 B2 | 6/2015 | Steinhauer et al. |
| 9,072,849 B2 | 7/2015 | Steinhauer et al. |
| 9,132,377 B2 | 9/2015 | Richey, II et al. |
| 9,175,577 B2 | 11/2015 | Papamoschou et al. |
| 9,266,053 B2 | 2/2016 | Shelnutt et al. |
| 9,317,660 B2 | 4/2016 | Burich et al. |
| 9,327,090 B2 | 5/2016 | Steinhauer et al. |
| 9,352,110 B2 | 5/2016 | Steinhauer et al. |
| 9,364,626 B2 | 6/2016 | Carter et al. |
| 9,440,179 B2 | 9/2016 | Wilkinson et al. |
| 9,460,262 B2 | 10/2016 | Kaufman et al. |
| 9,462,977 B2 | 10/2016 | Horseman |
| 9,637,280 B2 * | 5/2017 | Gotoh ............... B29C 45/14778 |
| 9,693,734 B2 | 7/2017 | Horseman |
| 9,714,860 B2 | 7/2017 | Obenchain |
| 9,763,585 B2 | 9/2017 | Addison et al. |
| 9,782,557 B2 | 10/2017 | Wilkinson et al. |
| 9,788,735 B2 | 10/2017 | Al-Ali |
| 9,808,156 B2 | 11/2017 | Horseman |
| 9,833,142 B2 | 12/2017 | Horseman |
| 9,838,508 B2 | 12/2017 | Salem |
| 9,839,786 B2 | 12/2017 | Rondoni et al. |

(56) References Cited

U.S. PATENT DOCUMENTS

| | | |
|---|---|---|
| 9,872,623 B2 | 1/2018 | Al-Ali |
| 9,872,965 B2 | 1/2018 | Baloa et al. |
| 9,956,370 B2 | 5/2018 | Wilkinson et al. |
| 9,957,125 B2 | 5/2018 | Ray |
| 9,990,466 B2 | 6/2018 | DeBusk et al. |
| 10,004,435 B2 | 6/2018 | Larvenz et al. |
| 10,010,969 B2 | 7/2018 | Reed et al. |
| 10,037,044 B2 | 7/2018 | Laberge et al. |
| 10,058,269 B2 | 8/2018 | Lynn |
| 10,108,785 B2 | 10/2018 | Kamen et al. |
| 10,139,282 B2 | 11/2018 | Chrostowski |
| 10,148,912 B1 | 12/2018 | Oliver et al. |
| 10,179,217 B2 | 1/2019 | Steinhauer et al. |
| 10,252,037 B2 | 4/2019 | Degen et al. |
| 10,271,779 B2 | 4/2019 | Addison et al. |
| 10,349,901 B2 | 7/2019 | Osypka et al. |
| 10,357,628 B2 | 7/2019 | Jagger et al. |
| 10,391,019 B2 | 8/2019 | Stryker et al. |
| 10,426,904 B2 | 10/2019 | Broborg et al. |
| 10,496,788 B2 | 12/2019 | Amarasingham et al. |
| 10,521,720 B2 | 12/2019 | Detzler et al. |
| 10,592,637 B2 | 3/2020 | Velamuri et al. |
| 10,630,814 B2 | 4/2020 | Barnes et al. |
| 10,753,598 B2 | 8/2020 | Chien |
| 10,948,175 B2 | 3/2021 | Chien |
| 2002/0053286 A1 | 5/2002 | Czabala |
| 2002/0096174 A1 | 7/2002 | Hill et al. |
| 2003/0068828 A1 | 4/2003 | Dadala et al. |
| 2003/0180164 A1 | 9/2003 | Bunner et al. |
| 2003/0215342 A1 | 11/2003 | Higashino |
| 2003/0231967 A1 | 12/2003 | Najafi et al. |
| 2004/0079359 A1 | 4/2004 | Aylsworth et al. |
| 2004/0167464 A1 | 8/2004 | Ireland et al. |
| 2004/0237488 A1 | 12/2004 | Stenersen |
| 2005/0259088 A1 | 11/2005 | Ogasawara et al. |
| 2005/0263199 A1 | 12/2005 | Meheen |
| 2006/0005842 A1 | 1/2006 | Rashad |
| 2006/0013682 A1 | 1/2006 | Martin et al. |
| 2006/0025932 A1 | 2/2006 | Dadala et al. |
| 2006/0086251 A1 | 4/2006 | Sprinkle |
| 2006/0092768 A1 | 5/2006 | Demas |
| 2006/0092769 A1 | 5/2006 | Demas |
| 2006/0174871 A1 | 8/2006 | Jagger et al. |
| 2006/0174872 A1 | 8/2006 | Jagger |
| 2006/0219245 A1 | 10/2006 | Holder |
| 2006/0220881 A1 | 10/2006 | Al et al. |
| 2006/0227123 A1 | 10/2006 | Bychkov et al. |
| 2006/0230768 A1 | 10/2006 | Huber et al. |
| 2006/0230929 A1 | 10/2006 | Bliss et al. |
| 2006/0251408 A1 | 11/2006 | Konno et al. |
| 2007/0032733 A1 | 2/2007 | Burton |
| 2007/0034590 A1* | 2/2007 | Hidding ............... B65D 1/0246 215/252 |
| 2007/0056584 A1 | 3/2007 | Jagger et al. |
| 2007/0140869 A1 | 6/2007 | St. Michel |
| 2007/0144519 A1 | 6/2007 | Henry et al. |
| 2007/0250017 A1 | 10/2007 | Carred et al. |
| 2008/0007396 A1 | 1/2008 | Parkulo et al. |
| 2008/0066616 A1 | 3/2008 | Sprinkle |
| 2008/0136652 A1 | 6/2008 | Vaisnys et al. |
| 2008/0165629 A1 | 7/2008 | Billeaudeaux |
| 2008/0238323 A1 | 10/2008 | Chan et al. |
| 2008/0246277 A1 | 10/2008 | Gallagher et al. |
| 2008/0257145 A1 | 10/2008 | Sprinkle |
| 2008/0262657 A1 | 10/2008 | Howell et al. |
| 2008/0294348 A1 | 11/2008 | Tanaka et al. |
| 2009/0065526 A1 | 3/2009 | Sprinkle |
| 2009/0118632 A1 | 5/2009 | Goepp |
| 2009/0126736 A1 | 5/2009 | Taylor et al. |
| 2009/0209839 A1 | 8/2009 | Ochs et al. |
| 2009/0211438 A1 | 8/2009 | Thompson et al. |
| 2009/0211448 A1 | 8/2009 | McClain |
| 2009/0216747 A1 | 8/2009 | Li et al. |
| 2009/0232706 A1 | 9/2009 | Dadala et al. |
| 2009/0316533 A1 | 12/2009 | Liu |
| 2010/0024729 A1 | 2/2010 | Cao |
| 2010/0071698 A1 | 3/2010 | Kiritake |
| 2010/0095841 A1 | 4/2010 | Naheiri |
| 2010/0106458 A1 | 4/2010 | Leu |
| 2010/0114218 A1 | 5/2010 | Heath |
| 2010/0146426 A1 | 6/2010 | Parkulo et al. |
| 2010/0214877 A1 | 8/2010 | Turk |
| 2010/0242734 A1 | 9/2010 | Maeda et al. |
| 2010/0253505 A1 | 10/2010 | Chou |
| 2010/0294127 A1 | 11/2010 | Dolensky |
| 2011/0017216 A1 | 1/2011 | Van Brunt et al. |
| 2011/0036352 A1 | 2/2011 | Estes et al. |
| 2011/0046996 A1 | 2/2011 | Foucher et al. |
| 2011/0056904 A1 | 3/2011 | Rozenberg |
| 2011/0073107 A1 | 3/2011 | Rodman et al. |
| 2011/0080348 A1 | 4/2011 | Lin et al. |
| 2011/0126829 A1 | 6/2011 | Carter |
| 2011/0128008 A1 | 6/2011 | Carter |
| 2011/0148773 A1 | 6/2011 | Rudolph |
| 2011/0148775 A1 | 6/2011 | Rudolph et al. |
| 2011/0211425 A1 | 9/2011 | Liu |
| 2011/0260850 A1 | 10/2011 | Ringenwald |
| 2011/0276828 A1 | 11/2011 | Tamaki et al. |
| 2011/0315140 A1 | 12/2011 | Shuman |
| 2012/0036461 A1 | 2/2012 | Parkulo et al. |
| 2012/0122545 A1 | 5/2012 | Watkins et al. |
| 2012/0321529 A1 | 12/2012 | Guo |
| 2013/0012788 A1 | 1/2013 | Horseman |
| 2013/0012789 A1 | 1/2013 | Horseman |
| 2013/0012790 A1 | 1/2013 | Horseman |
| 2013/0193100 A1* | 8/2013 | Lamoureux ............ B65D 41/325 215/45 |
| 2013/0233168 A1 | 9/2013 | Richey, II |
| 2013/0264218 A1 | 10/2013 | Vinton et al. |
| 2013/0297330 A1 | 11/2013 | Kamen et al. |
| 2013/0333702 A1 | 12/2013 | Baloa et al. |
| 2014/0000604 A1 | 1/2014 | Steinhauer et al. |
| 2014/0000605 A1 | 1/2014 | Steinhauer et al. |
| 2014/0000607 A1 | 1/2014 | Steinhauer et al. |
| 2014/0000608 A1 | 1/2014 | Steinhauer et al. |
| 2014/0000609 A1 | 1/2014 | Steinhauer et al. |
| 2014/0002246 A1 | 1/2014 | Steinhauer et al. |
| 2014/0006041 A1 | 1/2014 | Steinhauer et al. |
| 2014/0006052 A1 | 1/2014 | Steinhauer et al. |
| 2014/0007405 A1 | 1/2014 | Chambers et al. |
| 2014/0049792 A1 | 2/2014 | Ha |
| 2014/0163335 A1 | 6/2014 | Horseman |
| 2014/0163336 A1 | 6/2014 | Horseman |
| 2014/0163337 A1 | 6/2014 | Horseman |
| 2014/0166003 A1 | 6/2014 | Van Brunt et al. |
| 2014/0188516 A1 | 7/2014 | Kamen et al. |
| 2014/0190348 A1 | 7/2014 | Richey, II et al. |
| 2014/0343854 A1 | 11/2014 | Wollard |
| 2015/0077245 A1 | 3/2015 | Kaufman et al. |
| 2015/0128800 A1 | 5/2015 | Bliss |
| 2015/0164390 A1 | 6/2015 | Larvenz et al. |
| 2015/0174359 A1 | 6/2015 | Elliott et al. |
| 2015/0213224 A1 | 7/2015 | Amarasingham et al. |
| 2015/0234993 A1 | 8/2015 | Detzler et al. |
| 2015/0238721 A1 | 8/2015 | Rumph |
| 2015/0250960 A1 | 9/2015 | Broberg et al. |
| 2015/0320953 A1 | 11/2015 | Acker et al. |
| 2015/0362929 A1 | 12/2015 | Laberge et al. |
| 2016/0022971 A1 | 1/2016 | Degen et al. |
| 2016/0034042 A1 | 2/2016 | Joo |
| 2016/0152430 A1 | 6/2016 | Ray |
| 2016/0189345 A1 | 6/2016 | Fujita et al. |
| 2016/0206838 A1 | 7/2016 | Steinhauer et al. |
| 2016/0275261 A1 | 9/2016 | Velamuri et al. |
| 2016/0303388 A1 | 10/2016 | Rondoni |
| 2016/0324425 A1 | 11/2016 | Addison et al. |
| 2016/0367197 A1 | 12/2016 | Addison et al. |
| 2016/0371479 A1 | 12/2016 | Wynen et al. |
| 2016/0375218 A1 | 12/2016 | Sprinkle et al. |
| 2016/0378067 A1 | 12/2016 | Bishop |
| 2017/0000395 A1 | 1/2017 | Addison et al. |
| 2017/0000423 A1 | 1/2017 | Addison et al. |
| 2017/0011131 A1 | 1/2017 | Li et al. |
| 2017/0017767 A1 | 1/2017 | Flower et al. |

(56) References Cited

U.S. PATENT DOCUMENTS

| | | | |
|---|---|---|---|
| 2017/0053077 A1 | 2/2017 | Osypka et al. | |
| 2017/0063456 A1 | 3/2017 | Yamasaki et al. | |
| 2017/0080262 A1 | 3/2017 | Freres et al. | |
| 2017/0117444 A1 | 4/2017 | Stoll et al. | |
| 2017/0119235 A1 | 5/2017 | Hyde et al. | |
| 2017/0122774 A1 | 5/2017 | Quady | |
| 2017/0202728 A1 | 7/2017 | Stryker | |
| 2017/0221414 A1 | 8/2017 | Endo | |
| 2017/0224231 A1 | 8/2017 | Al-Ali | |
| 2017/0224233 A1 | 8/2017 | Al-Ali | |
| 2017/0291708 A1 | 10/2017 | Buenting et al. | |
| 2018/0014791 A1 | 1/2018 | Montgomery et al. | |
| 2018/0156667 A1 | 6/2018 | Chrostowski | |
| 2018/0192965 A1 | 7/2018 | Rose et al. | |
| 2018/0271421 A1 | 9/2018 | Larvenz et al. | |
| 2018/0279475 A1 | 9/2018 | Kloth et al. | |
| 2018/0289992 A1 | 10/2018 | Peake | |
| 2018/0314416 A1 | 11/2018 | Powderly et al. | |
| 2018/0369532 A1 | 12/2018 | Nebrigic | |
| 2019/0065973 A1 | 2/2019 | Elwakeel | |
| 2019/0068760 A1 | 2/2019 | Barnes et al. | |
| 2019/0134340 A1 | 5/2019 | Nebrigac | |
| 2019/0143056 A1 | 5/2019 | Steinhauer et al. | |
| 2019/0200577 A1 | 7/2019 | Kath | |
| 2019/0295718 A1 | 9/2019 | Lawhorn | |
| 2019/0341793 A1 | 11/2019 | Chien | |
| 2019/0374139 A1 | 12/2019 | Kiani et al. | |
| 2020/0013501 A1 | 1/2020 | Page | |
| 2020/0016605 A1 | 1/2020 | Nebrigac | |
| 2020/0035348 A1 | 1/2020 | Sartor et al. | |
| 2020/0060545 A1 | 2/2020 | Maher et al. | |
| 2020/0064011 A1 | 2/2020 | Nakano | |
| 2020/0081856 A1 | 3/2020 | Kojima | |
| 2020/0146442 A1 | 5/2020 | Rutzke | |
| 2020/0193806 A1 | 6/2020 | Finke et al. | |
| 2020/0264031 A1 | 8/2020 | Lease et al. | |
| 2021/0038855 A1 | 2/2021 | Oddo et al. | |
| 2021/0069360 A1 | 3/2021 | Shane et al. | |
| 2021/0249010 A1 | 8/2021 | Tayshete et al. | |
| 2021/0252317 A1 | 8/2021 | Peake | |
| 2021/0366320 A1 | 11/2021 | Wang et al. | |
| 2022/0134035 A1 | 5/2022 | Miaralipour et al. | |
| 2022/0305428 A1 | 9/2022 | Yehya | |

FOREIGN PATENT DOCUMENTS

| | | |
|---|---|---|
| AU | 748829 B2 | 6/2002 |
| AU | 200072387 A | 6/2002 |
| AU | 2008240038 A1 | 10/2009 |
| AU | 2010282150 A1 | 7/2012 |
| AU | 2012279039 A1 | 1/2014 |
| AU | 2012279044 A1 | 1/2014 |
| AU | 2012279110 A1 | 1/2014 |
| AU | 2013364131 A1 | 7/2015 |
| AU | 2013364131 A8 | 9/2015 |
| AU | 2013364131 A2 | 10/2015 |
| AU | 2014357428 B2 | 5/2019 |
| AU | 2013364131 B2 | 7/2019 |
| AU | 2018258679 A1 | 11/2019 |
| AU | 2018295533 A1 | 1/2020 |
| BR | 112015015024 A2 | 7/2017 |
| CA | 2310667 A1 | 6/1999 |
| CA | 2379697 A1 | 2/2001 |
| CA | 2438457 C | 2/2004 |
| CA | 2772539 A1 | 6/2004 |
| CA | 2683367 A1 | 10/2008 |
| CA | 2506292 C | 5/2012 |
| CA | 2839287 A1 | 1/2013 |
| CA | 2840969 A1 | 1/2013 |
| CA | 2840975 A1 | 1/2013 |
| CA | 2840984 A1 | 1/2013 |
| CA | 3016496 A1 | 1/2013 |
| CA | 2310667 C | 7/2013 |
| CA | 2772539 C | 4/2014 |
| CA | 2896086 A1 | 6/2014 |
| CA | 2933599 A1 | 6/2015 |
| CA | 2945137 A1 | 10/2015 |
| CA | 2982855 A1 | 11/2016 |
| CA | 2840979 C | 7/2018 |
| CA | 3050643 A1 | 7/2018 |
| CA | 3059209 A1 | 11/2018 |
| CA | 3069278 A1 | 1/2019 |
| CA | 2933599 C | 12/2019 |
| CA | 3016496 C | 1/2020 |
| CN | 87102164 | 11/1987 |
| CN | 2585215 Y | 11/2003 |
| CN | 1610516 A | 4/2005 |
| CN | 1697681 A | 11/2005 |
| CN | 1697682 A | 11/2005 |
| CN | 1780655 A | 5/2006 |
| CN | 2839861 A | 11/2006 |
| CN | 101506868 A | 8/2009 |
| CN | 101520690 A | 9/2009 |
| CN | 101681455 A | 3/2010 |
| CN | 101687134 A | 3/2010 |
| CN | 101873824 A | 10/2010 |
| CN | 1780655 B | 12/2010 |
| CN | 101520690 B | 7/2011 |
| CN | 101141567 B | 12/2012 |
| CN | 103448727 A | 12/2013 |
| CN | 103534664 A | 1/2014 |
| CN | 101543047 B | 2/2014 |
| CN | 103764021 A | 4/2014 |
| CN | 103781405 A | 5/2014 |
| CN | 103781409 A | 5/2014 |
| CN | 104235038 A | 12/2014 |
| CN | 204226229 U | 3/2015 |
| CN | 104951225 A | 9/2015 |
| CN | 104969227 A | 10/2015 |
| CN | 105269352 A | 1/2016 |
| CN | 105351296 A | 2/2016 |
| CN | 205237581 U | 5/2016 |
| CN | 205302544 U | 6/2016 |
| CN | 205344448 U | 6/2016 |
| CN | 205578301 U | 9/2016 |
| CN | 205578306 U | 9/2016 |
| CN | 205644217 U | 10/2016 |
| CN | 106075696 A | 11/2016 |
| CN | 106102571 A | 11/2016 |
| CN | 106455927 A | 2/2017 |
| CN | 103477340 B | 3/2017 |
| CN | 106574784 A | 4/2017 |
| CN | 106793238 A | 5/2017 |
| CN | 106887110 A | 6/2017 |
| CN | 106913326 A | 7/2017 |
| CN | 106931478 A | 7/2017 |
| CN | 206459246 U | 9/2017 |
| CN | 206655848 U | 11/2017 |
| CN | 108348148 A | 7/2018 |
| CN | 105373219 B | 9/2018 |
| CN | 109171755 A | 1/2019 |
| CN | 110292696 A | 10/2019 |
| CN | 110431509 A | 11/2019 |
| CN | 110604580 A | 12/2019 |
| CN | 107430497 B | 3/2020 |
| CN | 111792030 A | 10/2020 |
| DE | 573822 C | 4/1933 |
| DE | 3723019 A1 | 1/1989 |
| DE | 29605889 U1 | 6/1996 |
| DE | 19936893 A1 | 2/2001 |
| DE | 10037227 A1 | 2/2002 |
| DE | 19936893 C2 | 8/2002 |
| DE | 102005042268 A1 | 5/2006 |
| DE | 102007021564 A1 | 11/2008 |
| DE | 202006020670 U1 | 7/2009 |
| DE | 102008016768 A1 | 10/2009 |
| DE | 102008030790 A1 | 12/2009 |
| DE | 102014103377 A1 | 9/2014 |
| DE | 102014103397 A1 | 9/2014 |
| DE | 102016116761 A1 | 3/2017 |
| DE | 102017204049 B3 | 5/2018 |
| DE | 102018115858 A1 | 1/2020 |
| EP | 0420620 A2 | 4/1991 |
| EP | 0885645 A2 | 12/1998 |

(56) References Cited

FOREIGN PATENT DOCUMENTS

| | | | |
|---|---|---|---|
| EP | 1032906 A1 | 9/2000 |
| EP | 1157731 A1 | 11/2001 |
| EP | 0885645 B1 | 1/2005 |
| EP | 1661596 B1 | 5/2006 |
| EP | 1707928 A1 | 10/2006 |
| EP | 1895892 A1 | 3/2008 |
| EP | 1340071 B1 | 3/2009 |
| EP | 2136682 A1 | 12/2009 |
| EP | 2138060 A2 | 12/2009 |
| EP | 2197530 A2 | 6/2010 |
| EP | 2266093 A2 | 12/2010 |
| EP | 2058787 B1 | 12/2013 |
| EP | 2729052 A1 | 5/2014 |
| EP | 2729054 A1 | 5/2014 |
| EP | 2729056 A1 | 5/2014 |
| EP | 2751751 A1 | 7/2014 |
| EP | 2773410 A1 | 9/2014 |
| EP | 2861139 A1 | 4/2015 |
| EP | 2895224 A1 | 7/2015 |
| EP | 0936362 A2 | 10/2015 |
| EP | 1636076 B1 | 12/2015 |
| EP | 2613838 B1 | 3/2016 |
| EP | 2138060 B1 | 6/2016 |
| EP | 3069279 A1 | 9/2016 |
| EP | 3082977 A2 | 10/2016 |
| EP | 3117355 A1 | 1/2017 |
| EP | 3129949 A2 | 2/2017 |
| EP | 1850917 B1 | 6/2017 |
| EP | 3282382 A1 | 2/2018 |
| EP | 3283165 A1 | 2/2018 |
| EP | 3286910 A1 | 2/2018 |
| EP | 3294120 A1 | 3/2018 |
| EP | 3316769 A1 | 5/2018 |
| EP | 3316770 A1 | 5/2018 |
| EP | 2729051 B1 | 6/2018 |
| EP | 3372910 A1 | 9/2018 |
| EP | 2058162 B1 | 1/2019 |
| EP | 2936362 B1 | 3/2019 |
| EP | 3578220 A1 | 12/2019 |
| EP | 3614946 A1 | 3/2020 |
| EP | 3616040 A1 | 3/2020 |
| EP | 3627261 A1 | 3/2020 |
| EP | 3634538 A1 | 4/2020 |
| EP | 3638557 A1 | 4/2020 |
| FR | 2865655 A1 | 8/2005 |
| FR | 2865655 B1 | 4/2006 |
| GB | 1270296 A | 4/1972 |
| GB | 1375908 A | 12/1974 |
| IN | 201202311 P4 | 5/2013 |
| IN | 201504225 P4 | 7/2016 |
| IN | 201647029095 A | 10/2016 |
| IN | 201721043516 A | 12/2017 |
| IN | 201947043607 A | 11/2019 |
| JP | 63-134026 | 6/1988 |
| JP | 2-58091 A | 2/1990 |
| JP | 6-93850 | 4/1994 |
| JP | 10-66820 | 3/1998 |
| JP | 10104190 A | 4/1998 |
| JP | 2001095920 A | 4/2001 |
| JP | 3348956 B2 | 11/2002 |
| JP | 2003-024269 | 1/2003 |
| JP | 2004258828 A | 9/2004 |
| JP | 2005098571 A | 4/2005 |
| JP | 2005-245735 | 9/2005 |
| JP | 2006153337 A | 6/2006 |
| JP | 2007508572 A | 4/2007 |
| JP | 2007170410 | 7/2007 |
| JP | 2008011933 | 1/2008 |
| JP | 4088313 B2 | 5/2008 |
| JP | 2008113861 A | 5/2008 |
| JP | 2008531218 A | 8/2008 |
| JP | 2008209094 A | 9/2008 |
| JP | 2008-276275 A | 11/2008 |
| JP | 2010502423 A | 1/2010 |
| JP | 4469972 B2 | 6/2010 |
| JP | 2010119762 A | 6/2010 |
| JP | 2010287576 A | 12/2010 |
| JP | 2011075223 A | 4/2011 |
| JP | 2011106373 A | 6/2011 |
| JP | 2011520170 A | 7/2011 |
| JP | 2012-157812 | 8/2012 |
| JP | 5020358 B2 | 9/2012 |
| JP | 5250037 B2 | 7/2013 |
| JP | 5275955 B2 | 8/2013 |
| JP | 2013218725 A | 10/2013 |
| JP | 2014064771 | 4/2014 |
| JP | 2014523038 A | 9/2014 |
| JP | 2014523039 A | 9/2014 |
| JP | 2014524797 A | 9/2014 |
| JP | 2014225236 A | 12/2014 |
| JP | 2015007083 A | 1/2015 |
| JP | 5711389 B2 | 4/2015 |
| JP | 2015-531310 | 11/2015 |
| JP | 2015-217211 | 12/2015 |
| JP | 2016033154 A | 3/2016 |
| JP | 2016509284 A | 3/2016 |
| JP | 2016197422 A | 11/2016 |
| JP | 2017503571 A | 2/2017 |
| JP | 2017508532 A | 3/2017 |
| JP | 6144238 B2 | 6/2017 |
| JP | 2017105839 A | 6/2017 |
| JP | 2017130833 A | 7/2017 |
| JP | 2017138567 A | 8/2017 |
| JP | 2017143589 A | 8/2017 |
| JP | 2017146065 A | 8/2017 |
| JP | 06203634 B2 | 9/2017 |
| JP | 6252607 B2 | 12/2017 |
| JP | 06299785 B2 | 3/2018 |
| JP | 6307238 | 4/2018 |
| JP | 6310507 B2 | 4/2018 |
| JP | 2018511440 A | 4/2018 |
| JP | 2018122119 A | 8/2018 |
| JP | 2018-531152 | 10/2018 |
| JP | 2019500927 A | 1/2019 |
| JP | 6465155 B2 | 2/2019 |
| JP | 6483594 B2 | 3/2019 |
| JP | 2019082290 A | 5/2019 |
| JP | 6581667 B2 | 9/2019 |
| JP | 2019207684 A | 12/2019 |
| JP | 2020011074 A | 1/2020 |
| JP | 6709479 | 6/2020 |
| JP | 2002-297087 | 10/2022 |
| JP | 7580153 B2 | 11/2024 |
| KR | 2009069335 A | 6/2009 |
| KR | 2014070553 A | 6/2014 |
| KR | 2014114422 A | 9/2014 |
| KR | 2015117092 A | 10/2015 |
| KR | 20150117092 A | 10/2015 |
| KR | 101816443 B1 | 1/2018 |
| KR | 2018009326 A | 1/2018 |
| KR | 101942785 B1 | 1/2019 |
| KR | 2019019180 A | 2/2019 |
| KR | 2019089405 A | 7/2019 |
| KR | 2019093380 A | 8/2019 |
| KR | 2019112507 A | 10/2019 |
| KR | 102072394 B1 | 2/2020 |
| KR | 2020031433 A | 3/2020 |
| KR | 102103631 B1 | 4/2020 |
| KR | 2020054445 A | 5/2020 |
| MX | 2010005090 A | 5/2010 |
| MX | 2014007304 A | 7/2014 |
| MX | 2015004842 A | 7/2015 |
| MX | 355476 B | 4/2018 |
| NO | 178100 | 10/1995 |
| RU | 2015143725 A | 4/2017 |
| WO | 1997007439 A1 | 2/1997 |
| WO | 1998007930 A1 | 2/1998 |
| WO | 1998056488 A1 | 12/1998 |
| WO | 1998057165 A1 | 12/1998 |
| WO | 1999027483 A1 | 6/1999 |
| WO | 2001008752 A1 | 2/2001 |
| WO | 2004009161 A1 | 1/2004 |
| WO | 2005029452 A2 | 3/2005 |
| WO | 2005071372 A1 | 8/2005 |

(56) References Cited

FOREIGN PATENT DOCUMENTS

| | | | |
|---|---|---|---|
| WO | 2006086415 | A2 | 8/2006 |
| WO | 2006086472 | A2 | 8/2006 |
| WO | 2006086522 | A2 | 8/2006 |
| WO | 2006092635 | A1 | 9/2006 |
| WO | 2006118654 | A1 | 11/2006 |
| WO | 2007072385 | A2 | 6/2007 |
| WO | 2013006627 | A2 | 6/2007 |
| WO | 2007095266 | A2 | 8/2007 |
| WO | 2008036159 | A1 | 3/2008 |
| WO | 2008128250 | A1 | 10/2008 |
| WO | 2008131338 | A1 | 10/2008 |
| WO | 2009022320 | A2 | 2/2009 |
| WO | 2009032540 | A1 | 3/2009 |
| WO | 2009052704 | A1 | 4/2009 |
| WO | 2009/105541 | A1 | 8/2009 |
| WO | 2009114249 | A2 | 9/2009 |
| WO | 2009148646 | A2 | 12/2009 |
| WO | 2010082322 | A1 | 7/2010 |
| WO | 2011088539 | A1 | 7/2011 |
| WO | 2011017778 | A9 | 11/2012 |
| WO | 2012174420 | A2 | 12/2012 |
| WO | 2013006615 | A1 | 1/2013 |
| WO | 2013006632 | A1 | 1/2013 |
| WO | 2013067223 | A1 | 5/2013 |
| WO | 2013134645 | A1 | 9/2013 |
| WO | 2013188013 | A1 | 12/2013 |
| WO | 2014005106 | A1 | 1/2014 |
| WO | 2014041104 | A1 | 3/2014 |
| WO | 2014060726 | A1 | 4/2014 |
| WO | 2014071145 | A1 | 5/2014 |
| WO | 2014100687 | A2 | 6/2014 |
| WO | 2014101824 | A1 | 7/2014 |
| WO | 2015073459 | A1 | 5/2015 |
| WO | 2015095532 | A2 | 6/2015 |
| WO | 2015136502 | A1 | 9/2015 |
| WO | 2015157575 | A2 | 10/2015 |
| WO | 2016105552 | A1 | 6/2016 |
| WO | 2016168119 | A1 | 10/2016 |
| WO | 2016172469 | A1 | 10/2016 |
| WO | 2016182853 | A1 | 11/2016 |
| WO | 2017004068 | A1 | 1/2017 |
| WO | 2017004069 | A1 | 1/2017 |
| WO | 2017029396 | A1 | 2/2017 |
| WO | 2017101747 | A1 | 6/2017 |
| WO | 2017106636 | A1 | 6/2017 |
| WO | 2017106644 | A1 | 6/2017 |
| WO | 2017126392 | A1 | 7/2017 |
| WO | 2017141774 | A1 | 8/2017 |
| WO | 2017218295 | A1 | 12/2017 |
| WO | 2018016852 | A1 | 1/2018 |
| WO | 2018044959 | A1 | 3/2018 |
| WO | 2018200865 | A1 | 11/2018 |
| WO | 2018201067 | A1 | 11/2018 |
| WO | 2018209112 | A1 | 11/2018 |
| WO | 2019008529 | A1 | 1/2019 |
| WO | 2019202390 | A1 | 10/2019 |
| WO | 2019236759 | A1 | 12/2019 |
| WO | 2020023186 | A1 | 1/2020 |
| WO | 2020037375 | A1 | 2/2020 |
| WO | 2020041785 | A1 | 2/2020 |
| WO | 2020042639 | A1 | 3/2020 |
| WO | 2020086528 | A1 | 4/2020 |
| WO | 2021056065 | A1 | 4/2021 |
| WO | 2021194416 | A1 | 9/2021 |
| WO | 2021194426 | A1 | 9/2021 |
| WO | 2022005388 | A1 | 1/2022 |

OTHER PUBLICATIONS

Chinh et al. "Simulation and Experimental Study of a Single Fixed-Bed Model of Nitrogen Gas Generator Working by Pressure Swing Adsorption", MDPI, Processes 2019, retrieved on Sep. 22, 2021, retrieved from <URL: https://www.mdpi.com/2227-9717/7/10/654.

Ridl, "Audible Alerts and Visible Signals for the Inogen One GS", Inogen One GS blog, Oct. 30, 2019. (12 pages).
International Search Report and Written Opinion from PCT/US21/41717 dated Oct. 21, 2021.
International Search Report and Written Opinion from PCT/US2021/041718 dated Nov. 4, 2021.
International Search Report and Written Opinion from PCT/US2021/041719 dated Oct. 27, 2021.
International Search Report and Written Opinion from PCT/US2021/041712 dated Dec. 16, 2021.
Invitation to Pay Additional Fees from PCT/US21/41712 dated Oct. 6, 2021 (2 pages).
Notice of Allowance from U.S. Appl. No. 17/376,278 dated Oct. 23, 2023.
Office Action from U.S. Appl. No. 17/376,266 dated Oct. 12, 2023.
Office Action for Japanese Patent Application No. 2023-502667 mailed Aug. 28, 2023, with English translation attached.
Office Action from U.S. Appl. No. 17/376,202 dated Jun. 7, 2023.
Office Action from U.S. Appl. No. 17/376,278 dated Aug. 23, 2023.
Notice of Allowance from U.S. Appl. No. 17/376,253 dated Nov. 24, 2023.
Office Action from U.S. Appl. No. 17/376,202 dated Jan. 3, 2024.
Invacare XPO2 Portable TM Portable Oxygen Concentrator Brochure, 2010, 4 pages.
Invacare Platinum Mobile POC1-100B, POC1-100C en Oxygen Concentrator User Manual, 2018, 160 pages.
Invacare SOLO2 TM Transportable Oxygen Concentrator User Manual, 2010, 52 pages.
Invacare Perfecto2 TM V Oxygen Concentrator Brochure, 2009, 2 pages.
Invacare Platinum™ 10L Oxygen ConcentratorIRC10LXO2 en HomeFill® System Compatible User Manual, 2016, 36 pages.
Invacare Platinum 10 Oxygen Concentrator Brochure, 2019, 2 pages.
International Search Report and Written Opinion from PCT/US21/41714 dated Nov. 15, 2021 (13 pages).
International Search Report and Written Opinion from PCT/US21/41710 dated Nov. 15, 2021 (16 pages).
International Search Report and Written Opinion from PCT/US21/41711 dated Oct. 21, 2021 (13 pages).
Office action from U.S. Appl. No. 17/376,197 dated May 8, 2024.
Office action from U.S. Appl. No. 17/376,266 dated Apr. 5, 2024.
Allowance from U.S. Appl. No. 17/376,266 dated Jul. 25, 2024.
Office action from Canadian Application No. 3,189,534 dated May 24, 2024.
Office action from Candian Application No. 3189568 dated Jun. 4, 2024.
Search Report from European Application No. 21842676.5 dated Jul. 8, 2024.
Search Report from European Application No. 21843492.6, Jul. 10, 2024.
Office action from Japanese Application No. 2023-502665 dated Mar. 11, 2024.
Office action from Japanese Application No. 2023-502570 dated Mar. 29, 2024.
Office action from Japanese Application No. 2023-502666 dated May 23, 2024.
Office action from Japanese Application No. 2023-502671 dated Mar. 13, 2024.
Britannica, The Editors of Encyclopaedia, "Newton's laws of motion", Encyclopedia Britannica, Mar. 28, 2024, 2 pgs., https://www.britannica.com/science/Newtons-laws-of-motion (Year 2024).
Search Report from European Application No. 21843561.8 dated Jun. 27, 2024.
Canadian Office action from 3,189,535 dated Apr. 29, 2024.
Canadian Office action from 3,189,573 dated May 24, 2024.
Canadian Office action from 3,189,540 dated Apr. 30, 2024.
Allowance from U.S. Appl. No. 17/736,202 dated Apr. 24, 2024.
Office action from Japanese Application No. 2023-502670 dated Aug. 7, 2024.
Office action from Canadian Application No. 3,189,542 dated Aug. 2, 2024.
Office action from U.S. Appl. No. 17/376,205 dated Aug. 9, 2024.

(56) References Cited

OTHER PUBLICATIONS

Office action from Japanese Application No. 2023-502671 dated Jul. 31, 2024.
Notice of Allowance from U.S. Appl. No. 17/376,266 dated Aug. 14, 2024, 8 pages.
Notice of Allowance from U.S. Appl. No. 17/376,202 dated Apr. 24, 2024, 9 pages.
Notice of Allowance from U.S. Appl. No. 17/376,202 dated Aug. 9, 2024, 5 pages.
Office Action for Canadian Patent Application No. 3,189,544 dated Jun. 4, 2024, 4 pages.
Office Action for European Patent Application No. 21842977.7 dated Oct. 25, 2024, 11 pages.
Office Action for Japanese Patent Application No. 2023-502670 dated Apr. 2, 2024, 10 pages.
Office Action for Japanese Patent Application No. 2023-502663 dated Dec. 25, 2023, 11 pages.
Office Action for Japanese Patent Application No. 2023-502664 dated Sep. 5, 2023, 5 pages.
Office Action for Japanese Patent Application No. 2024-007939 dated Sep. 19, 2024, 7 pages.
Office Action for Japanese Patent Application No. 2023-502671 dated Jul. 29, 2024, 11 pages.
Office Action from U.S. Appl. No. 17/376,197 dated Nov. 1, 2024, 75 pages.
Office Action from U.S. Appl. No. 17/376,205 dated Jan. 24, 2025, 31 pages.
Restriction Requirement from U.S. Appl. No. 17/376,205 dated Mar. 7, 2024, 8 pages.
Restriction Requirement from U.S. Appl. No. 17/376,205 dated May 23, 2024, 6 pages.
Office action from Japanese Application No. 2023-502671 dated Jan. 17, 2025, 10 pages.
Office Action from U.S. Appl. No. 17/376,205 dated May 1, 2025, 20 pages.
Office Action from U.S. Appl. No. 18/418,447 dated May 6, 2025, 12 pages.
Search Report from European Application No. 21842403.4 dated Apr. 7, 2025.

* cited by examiner

SYSTEM AND METHOD FOR CONCENTRATING GAS

CROSS-REFERENCES TO RELATED APPLICATIONS

This application claims priority to U.S. Prov. Pat. App. Ser. No. 63/052,694 titled "System and Method for Concentrating Gas" and filed on Jul. 16, 2020 and Ser. No. 63/212,920 filed on Jun. 21, 2021.

This application incorporates by reference the following patent applications: U.S. Prov. Pat. App. Ser. No. 63/052,694 titled "System and Method for Concentrating Gas"; U.S. Prov. Pat. App. Ser. No. 63/052,700 titled "System and Method for Concentrating Gas"; U.S. Prov. Pat. App. Ser. No. 63/052,869 titled "System and Method for Concentrating Gas"; U.S. Prov. Pat. App. Ser. No. 63/052,533 titled "System and Method for Concentrating Gas"; and U.S. Prov. Pat. App. Ser. No. 63/052,647 titled "System and Method for Managing Medical Devices", all filed on Jul. 16, 2020; and U.S. Prov. Pat. App. Ser. No. 63/212,920 titled "System and Method for Concentrating Gas" filed on Jun. 21, 2021.

BACKGROUND

Various applications exist for the separation of gaseous mixtures. For example, the separation of nitrogen from atmospheric air can provide a highly concentrated source of oxygen. These various applications include the provision of elevated concentrations of oxygen for medical patients and flight personnel. Hence, it is desirable to provide systems that separate gaseous mixtures to provide a concentrated product gas, such as a breathing gas with a concentration of oxygen.

Several existing product gas or oxygen concentrating systems and methods, for example, are disclosed in U.S. Pat. Nos. 4,449,990, 5,906,672, 5,917,135, 5,988,165, 7,294,170, 7,455,717, 7,722,700, 7,875,105, 8,062,003, 8,070,853, 8,668,767, 9,132,377, 9,266,053, and 10,010,696 which are commonly assigned to Invacare Corporation of Elyria, Ohio and fully incorporated herein by reference.

Such systems are known to be either stationary, transportable, or portable. Stationary systems are intended to remain in one location such as, for example, a user's bedroom or living room. Transportable systems are intended to be moved from location to location and often include wheels or other mechanisms to facilitate movement. Portable systems are intended to be carried with the user such as, for example, via a shoulder strap or similar accessory.

Gas concentrating systems typically generate dynamic flows and pressures within their working components as part of the separation and concentrating process. These flows and pressures while necessary, also impact the mechanical wear and life of system components. Generally, the higher the necessary flows and pressures are within the system, the greater their impact on the mechanical wear and life of system components. Also, the higher the necessary flows and pressures are within the system, the higher the amount of energy that needs to be consumed in order to create the required flows and pressures. What is desired is a system that addresses these and other aspects of gas separating or concentrating systems.

In another aspect, gas concentrating systems require service during their life. Various gas separation components need to be either replaced, repaired or serviced. Manufacturers have a need to know when such components have been serviced outside of the manufacturer's domain. What is desired is a system that addresses this aspect of gas separating or concentrating systems as well.

SUMMARY

Gas concentrating systems and methods are provided. In one embodiment, systems and methods are provided that obtain the same or better level of performance by using lower operating flow rates and pressures within the system. This extends the life of system components and lower energy consumption. In one embodiment, gas separation (or sieve) beds that are used to separate gaseous components are provided that have lower flow and pressure requirements compared to conventional beds. The sieve beds include, for example, a diffuser having low solid area in cross-section and maximum open area for flow while providing adequate mechanical properties to contain sieve material and support filter media. This allows for efficient flow of gas into and out of the sieve beds, which reduces pressure loss and energy consumption, lowers dynamic and static pressure on sieve bed material, and improves the longevity of the sieve bed material and lessens the rate at which the sieve bed material fails mechanically. Other embodiments are also disclosed.

In another embodiment, systems and methods are provided having an indicator when a component has been serviced or repaired. This provides an indication whether the component has been tampered with in any manner. This allows the manufacturer to determine if the component was serviced, repaired, or tampered with outside the manufacturer's domain. Unauthorized service or repair could result in premature component wear and failure.

In yet another embodiment, systems and methods are disclosed having more uniform or optimized flow distributions and/or low velocities of gas entering the sieve bed material. Sieve bed caps and/or gas input interfaces are provided with flow modifying structures, partitions, or projections within a flow chamber to distribute the flow more evenly and to lower the velocity of the gas flow entering the sieve bed material. These structures, partitions and/or projections channel the incoming gas flow into adjacent spaces within the inner chamber of the cap/interface to provide a more uniform flow distribution of the gas entering the sieve material. More uniform flow distribution increases sieve bed efficiency by more uniformly introducing the gas into the sieve bed material to thereby limit or eliminate pockets of sieve material that the gas may not otherwise reach when the gas is non-uniformly distributed as it enters the sieve bed material. Also, reduced gas flow velocities reduce the mechanical wear and tear on the sieve bed material that causes dusting and fluidization of the material.

It is one object to provide a more efficient gas separation system and method.

It is another object to provide a gas separation system and method having lower flow rates and pressures.

It is another object to provide a gas separation system and method having a diffuser component with low solid area in cross-section thereby providing a large open area for flow.

It is another object to provide a gas separation system and method having a diffuser component with low solid area in cross-section thereby providing a large open area for flow while also providing adequate mechanical properties to contain sieve material and support filter media.

It is another object to provide a gas separation system and method having a component(s) to provide at least one tamper indication.

It is another object to provide a gas separation system and method having at least one sieve bed with a tamper indicator.

It is another object to provide a gas separation system and method having at least one anti-tamper component.

It is another object to provide a gas separation system and method having at least one anti-tamper sieve bed.

It is another object to provide a gas separation system and method that distributes flow into a desired profile for more even distribution of the gas entering a sieve bed.

It is another object to provide a gas separation system and method having an input device (e.g., a cap or insert) for deflecting and/or regulating flow into a desired profile as gas enters a sieve bed.

It is also another to provide a gas separation system and method that reduces the flow rate of gas entering the sieve bed material to reduce wear and tear (e.g., dusting, fluidization, etc.) of the sieve material.

These and other objects, features and advantages will become evident after a review of the following descriptions, drawings, and claims.

BRIEF DESCRIPTION OF THE DRAWINGS

In the accompanying drawings which are incorporated in and constitute a part of the specification, embodiments of the inventions are illustrated, which, together with a general description of the inventions given above, and the detailed descriptions given below, serve to example the principles of the inventions.

Unless otherwise indicated, each mechanical drawing is presented relative to scale. That is, the size, position, and location of the components illustrated in each drawing are shown to scale relative to each other, which may also include being shown magnified to scale.

DESCRIPTION

As described herein, when one or more components are described or shown as being connected, joined, affixed, coupled, attached, or otherwise interconnected, such interconnection may be direct as between the components or may be indirect such as through the use of one or more intermediary components. Also, as described herein, reference to a member, component, or portion shall not be limited to a single structural member, component, element, or portion but can include an assembly of components, members, elements, or portions.

Embodiments of the present inventions provide, for example, gas separation systems and methods having efficient flow of working gas into and out of sieve beds, reduced pressure loss and energy consumption, lower dynamic and static pressure on sieve bed material, and improved longevity of the sieve material by lessening the rate at which the sieve material fails mechanically and/or structurally. Efficient flow of working gas also lowers noise created by gas flow within the system. In one embodiment, the gas separation system includes at least one sieve bed having a diffuser arranged to subdivide the flow in its cross-section into smaller channels of flow thereby reducing turbulence and energy loss. The gas flow is substantially straightened by the diffuser and more energy is transferred into the intended direction of gas flow. The diffuser also has a low solid area (e.g., low solidity) in cross-section and high, and/or maximum, open area for flow while also providing adequate mechanical properties to contain sieve material and support filter media within the sieve bed.

Figure 1:
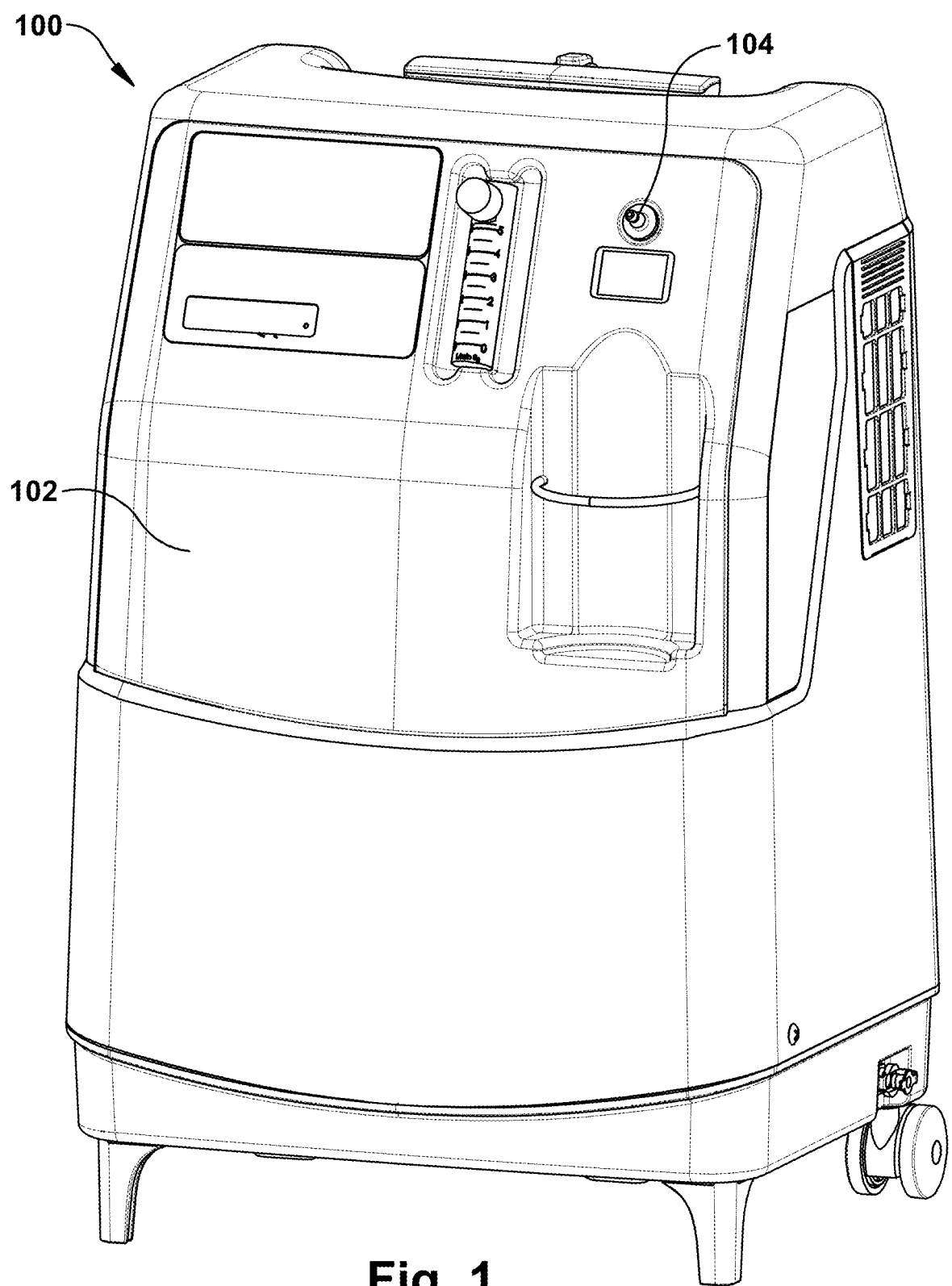
FIG. 1 shows one embodiment of the gas concentrating system.

Illustrated in FIG. 1 is one embodiment of a gas separation system 100, which can be an oxygen concentrating system. The system may be stationary such as, for example, for use in a hospital or a patient's home. The system can also be ambulatory or mobile such as, for example, for use by a patient when they are away from home. The system can be configured in a manner to allow the patient to carry the system such as, for example, through an over the shoulder strap or through an arrangement whereby the system includes a handle and wheels. Other mobility configurations are also included.

Oxygen system 100 includes a housing 102, which can be in one or more sections. Housing 102 includes a plurality of openings for the intake and discharge of various gases such as, for example, the intake of room air and the discharge of nitrogen and other gases. Oxygen system 100 generally intakes room air, which is mostly comprised of oxygen and nitrogen, and separates the nitrogen from the oxygen. The oxygen is stored in one or more internal or external storage or product tanks and the nitrogen is discharged back into the room air. For example, the oxygen gas may be discharged through port 104 to a patient through tubing and nasal cannula. Alternatively, the oxygen gas may be discharged through a supplemental port to an oxygen cylinder filling device, such as HOMEFILL® that is manufactured by Invacare Corp. of Elyria, Ohio, USA and one example of which is described in U.S. Pat. No. 5,988,165, which is incorporated by reference.

Figure 2:
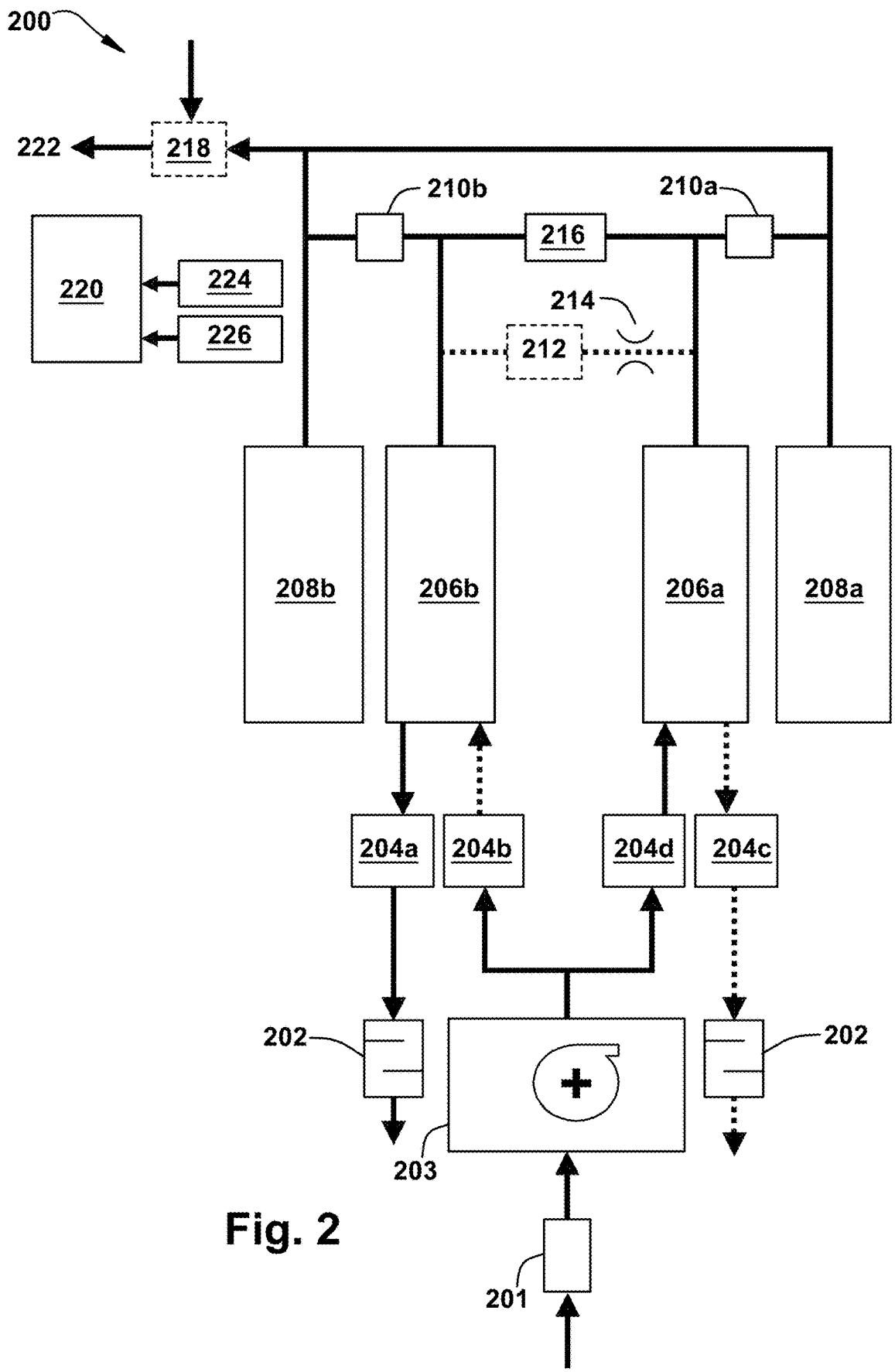
FIG. 2 is one embodiment of a pneumatic block diagram of a gas concentrating system.

FIG. 2 illustrates one embodiment of an exemplary pneumatic block diagram for a gas concentrating system using pressure swing adsorption (PSA). The system can include multiple gas separation sieve beds 206a and 206b, multiple valves 204a, 204b, 204c, and 204d, one or more product tanks 208a, 208b and a conserver valve/device 218. In this embodiment, product tanks 208a, 208b are shown connected so they act as one product tank but may also be arranged to act as two product tanks. The system also includes compressor/pump 203 and one or more filters 201 and mufflers 202.

Sieve beds 206a and 206b are filled with a physical separation medium or material. The separation material selectively adsorbs one or more adsorbable components and passes one or more nonadsorbable components of a gaseous mixture. Generally, the physical separation material is a molecular sieve with pores of uniform size and essentially the same molecular dimensions. These pores selectively adsorb molecules in accordance with molecular shape, polarity, degree of saturation, and the like. In one embodiment, the physical separation medium is an alum inasilicate composition with 4 to 5 ANG. (Angstrom) pores. More specifically, the molecular sieve is a sodium or calcium form of aluminasilicate, such as type 5A zeolite. Alternately, the aluminasilicate may have a higher silicon-to-aluminum ratio, larger pores, and an affinity for polar molecules, e.g., type 13x zeolite. The zeolite adsorbs nitrogen, carbon monoxide, carbon dioxide, water vapor, and other significant components of air. Other types of separation media may also be used to adsorb nitrogen from ambient or room air. Also, more than two sieve beds can be used. In other embodiments, the sieve beds 206a and 206b can be structurally integrated with one or more product tanks 208a and 208b, such as described in U.S. Pat. No. 8,668,767, which is hereby fully incorporated by reference for this and other features.

In operation, as shown by the solid lines in FIG. 2, during an exemplary fill cycle of separation bed 206a, pump/compressor 203 draws room air through filter 201 and to valve 204d and separation bed 206a, which produces oxygen at its output and into product tanks 208a, 208b through valve 210a. Pump/compressor 203 supplies air up to about 32 pounds per square inch during the fill phase to a sieve bed. Other working pressure ranges include about 15-32 pounds per square inch. Valves 210a and 210b may be check valves or any other similarly functioning valve that allows one-way flow.

While separation bed 206a is undergoing the fill cycle, separation bed 206b may be undergoing a purge cycle to expel any nitrogen gas from a previous fill cycle. During the purge cycle, previously pressurized separation bed 206b expels nitrogen gas through valve 204a and out to atmosphere through muffler 202. Separation bed 206a is being pressurized from its fill cycle. During the purge cycle, an amount of oxygen from separation bed 206a or product tanks 208a, 208b can be fed into separation bed 206b to preload or pre-charge the separation bed 206b with oxygen, as controlled by optional bleed valve 212 and fixed orifice 214, shown in FIG. 2 with dashed lines.

As shown by the dotted lines in FIG. 2, once separation bed 206a has been filled and/or separation bed 206b has been purged, control system 220 switches valves 204a, 204b, 204c, and 204d so that separation bed 206b enters the fill cycle while separation bed 206a enters the purge cycle. In this state, pump 203 directs room air into separation bed 206b, which produces oxygen at its output and into product tanks 208a, 208b through valve 210b. During the purge cycle, an amount of oxygen from separation bed 206b or product tanks 208a, 208b can be fed into separation bed 206a to preload or pre-charge separation bed 206a with oxygen, now flowing in the opposite direction as compared to the previous cycle. The illustrated system also includes an exemplary pressure equalization valve 216, which equalizes the pressure in the two separation beds prior to a purge/fill cycle change. Notably, not all embodiments of a PSA system require a pressure equalization valve.

The pressure equalization valve 216 can allow for a more efficient generation of oxygen by equalizing the pressure between the outputs of a separation bed (e.g., 206a) nearing the end of its fill cycle and a separation bed (e.g., 206b) nearing the end of its purge cycle. For example, pressure equalization valve 216 may be activated to equalize the pressure between the outputs of separation bed 206a and separation bed 206b near the end of each purge/fill cycle. U.S. Pat. Nos. 4,449,990 and 5,906,672, which are fully incorporated herein by reference, further describe the operation of pressure equalization valves. In this manner, each separation bed 206a, 206b cyclically undergoes alternating fill and purge cycles as controlled by control system 220 to generate oxygen.

As shown in FIG. 2, optional conserver valve/device 218 may be used to control the delivery of product gas to a user 222. Conserver valve 218 may switch between providing concentrated product gas from the product tanks 208a, 208b or venting to the room air. For example, the conserver valve 218 may be used to selectively provide various continuous or pulsed flows of oxygen concentrated product gas in an amount and at a time determined by the control system 220. This time is typically based on sensing an inhalation by the user, which is typically determined by sensing a drop in pressure or (increase in flow) proximate the user's nose or mouth.

In this embodiment, control system 220 may utilize various control schemes to optimize the production and delivery of concentrated product gas by controlling the activation, levels, and relative timing of pressure source 203 and valves 204a, 204b, 204c, 204d, 216, and 212, for example. This is accomplished by use of one or more pressure sensor(s) 224 and/or oxygen concentration sensor (s) 226. In one embodiment, pressure and oxygen sensors 224 and 226 monitor the pressure and oxygen concentration entering product tank(s) 208A and 208(b). In other embodiments, use of timed cycles can be employed wherein the cycle times are set at the factory or determined or optimized using a diagnostic process at system startup. In other embodiments, the cycle times can be determined from flow settings and/or sensed patient flow demands.

While FIG. 2 illustrates a pressure swing adsorption (PSA) cycle, other gas concentrating cycles may also be used including vacuum swing adsorption (VSA), vacuum—pressure swing adsorption (VPSA) or other similar modes. The particular gas concentrating mode is not critical to the embodiments of the invention described herein so long as they are capable of producing a concentrated gas such as oxygen to the user. Examples of the above modes of operation are disclosed in, for example, U.S. Pat. Nos. 9,266,053 and 9,120,050 which have been fully incorporated by reference.

Figures 3, 4A, 4B:
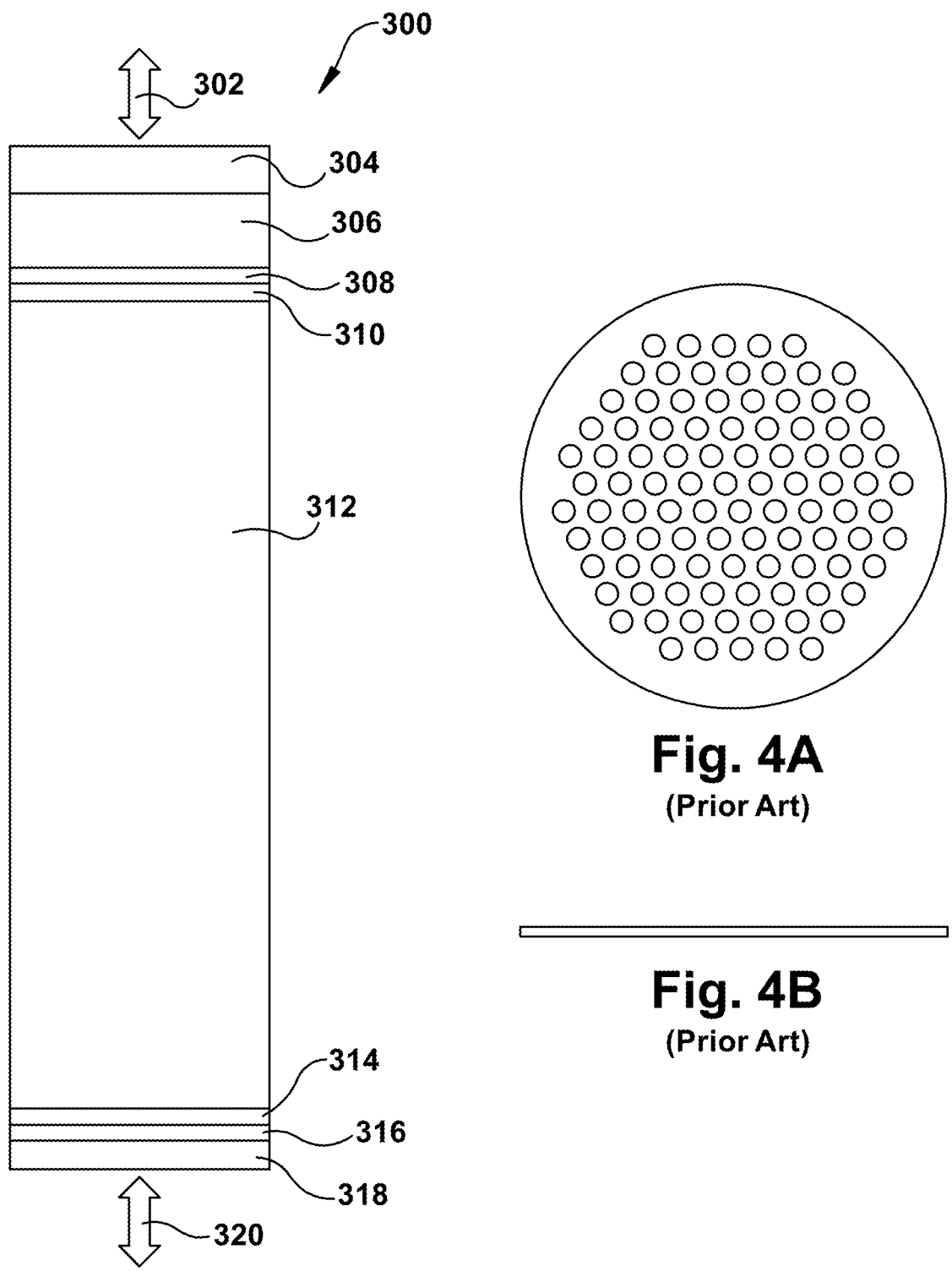
FIG. 3 is a block diagram of one embodiment of a gas separation or sieve bed.
FIGS. 4A-4B illustrate a prior art filter disc used with gas separation beds.

Referring now to FIG. 3, one embodiment of a sieve bed arrangement 300 is shown. Sieve bed 300 includes, for example, a first gas input/output 302 for receiving air and exhausting adsorbed nitrogen gas. An optional headspace 304 can be provided. Sieve bed 300 further includes spring 306, a perforated disc or diffuser 308, and one or more filter media 310. Spring 306 biases perforated disc or diffuser 308 against a sieve material 312 (e.g., granular separation or zeolite material as previously described) in order to keep the sieve material 312 pack together and to resist mechanical movement of the sieve material 312 during the dynamic pressures that are used to fill and purge sieve bed 300 during the gas separation process. The other end of the sieve material 312 is biased against one or more filter media 314 and a second perforated disc or diffuser 316. The second headspace 318 allows the non-adsorbed gas (e.g., oxygen) to enter and leave the sieve bed via input/output port 320. While this embodiment has been described with particularity, one or more components may be omitted, or several components may be integrated. For example, the one or more head spaces 304 and 318 can be substantially reduced or eliminated. Furthermore, more than one diffuser 308 can be used. For example, two or more diffusers 308 can be used back-to-back or two or more diffusers 308 can be used with one or more filter media 310 therebetween.

Figure 5A:
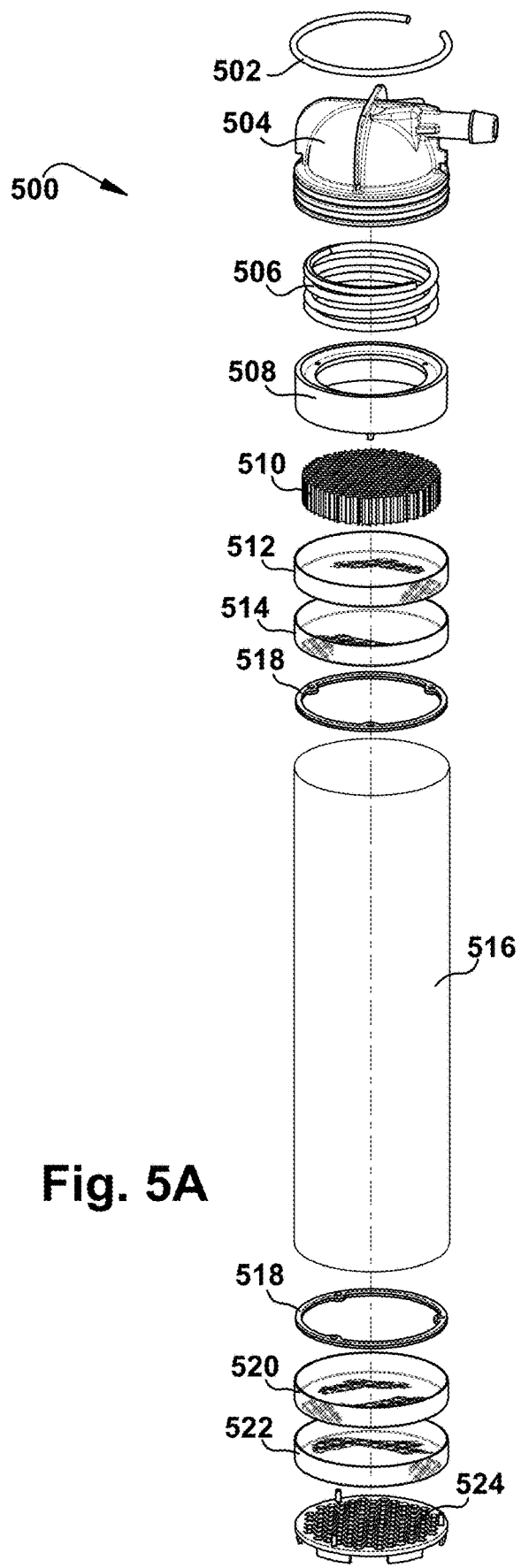
FIGS. 5A-5B illustrate perspective exploded views of one embodiment of a gas separation bed.
Figure 5B:
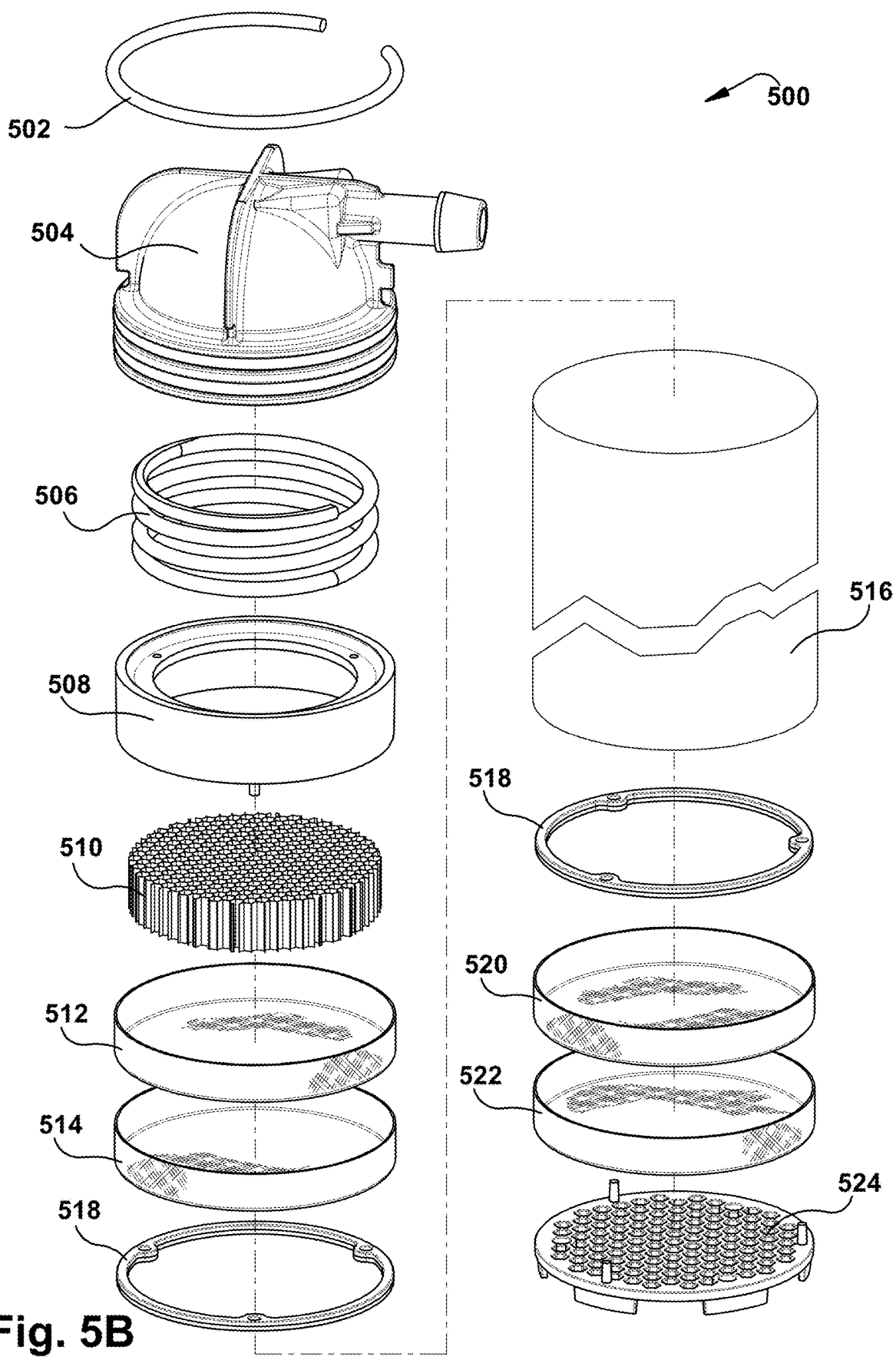
Figure 6A:
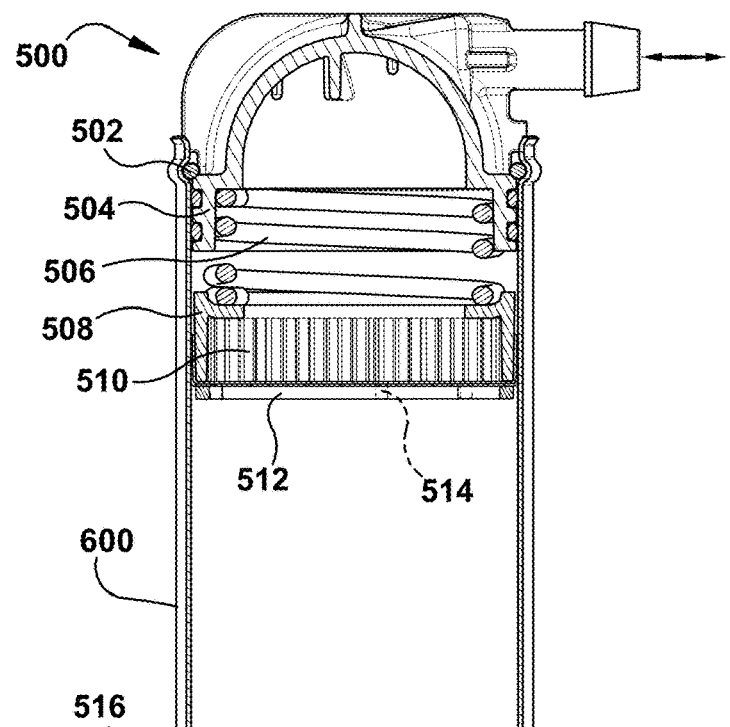
FIG. 6A-6B are various cross-sectional views of the gas separation bed embodiment of FIGS. 5A-5B.
Figure 6A:
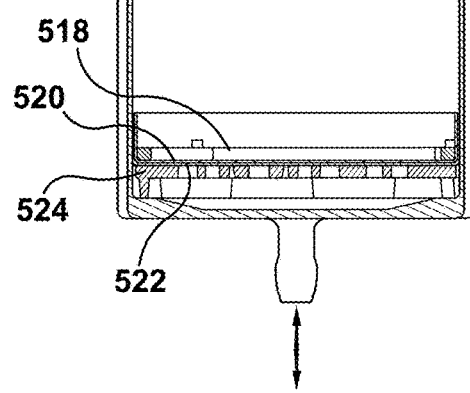
Figure 6B:
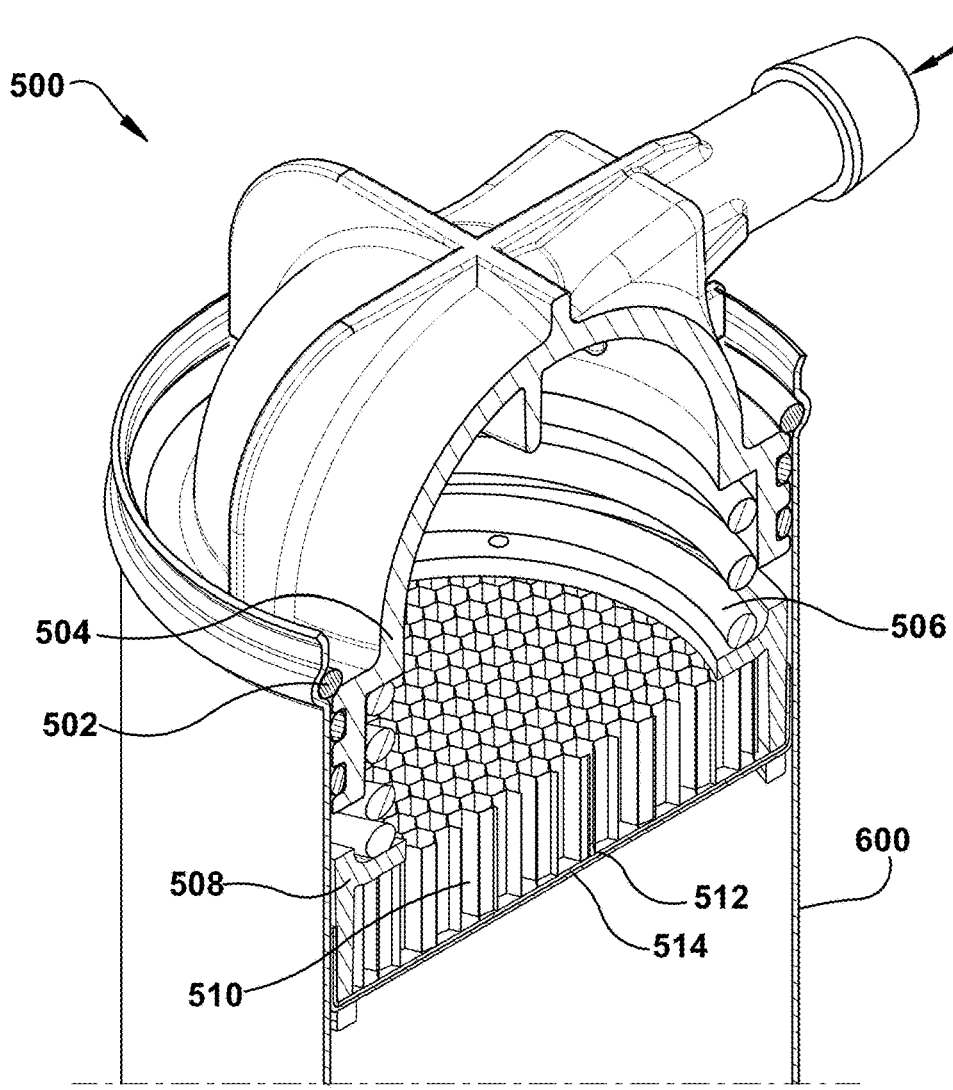
Figure 6B:
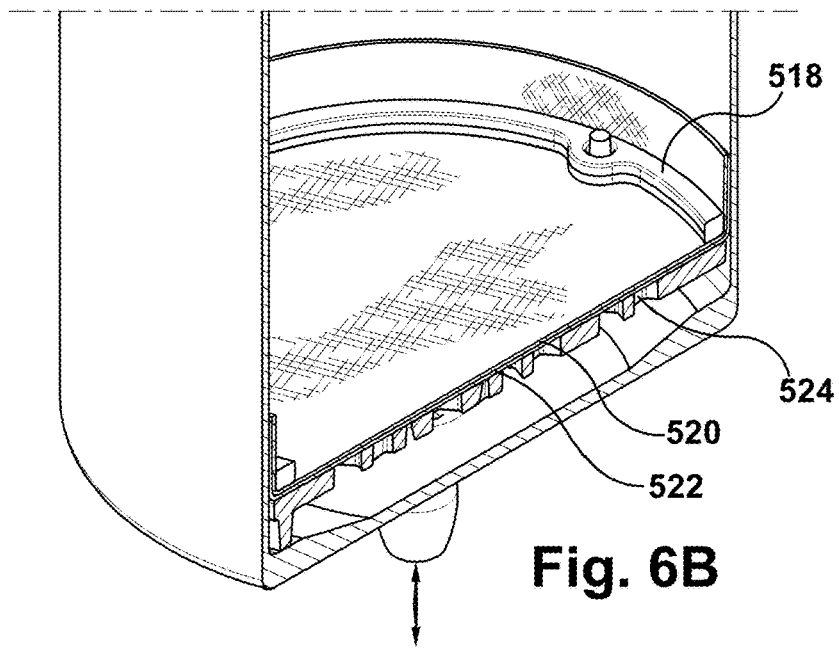

FIGS. 5A-5B illustrate another embodiment of a sieve bed 500. Sieve bed 500 includes, for example, many of the same functional components described in connection with sieve bed 300 of FIG. 3. Sieve bed 500 includes a retaining ring or clip 502 that is used to retain an input/output gas cap 504. A spring 506, retainer 508, diffuser 510, and filter media 512 and 514 further provided. Spring 506 biases retainer 508, diffuser 510, and filter media 512 and 514 against a granular sieve material 516 to keep it packed together within the sieve bed vessel walls to prevent or minimize mechanical movement of the sieve bed material during the dynamic pressures used in the fill and purge cycles of the separation process. A retaining ring 518 and second diffuser 524, along with one or more filter media 520 and 522, are located at the other end of sieve material 516. As described in connection with FIG. 3, more than one diffuser 510 can be used in any embodiment described herein. FIGS. 6A-6B illustrate various sectional prospective views of sieve bed 500 with its components assembled within a sieve bed vessel wall 600.

As noted above in connection with FIG. 2, the system draws ambient air through a compressor and moves it through a volume of material in the sieve bed(s), which has a propensity to retain nitrogen, thus leaving a surplus of oxygen in the system's output. The sieve material used to adsorb nitrogen is typically granular in form and must be retained within the sieve bed permitting air to flow in, oxygen flow out, and a periodic flushing of the sieve bed to exhaust the adsorbed nitrogen. As the gases flow in and out of the sieve bed, the granular sieve material must be retained and held to minimize its relative motion. For example, introduction of air under pressure to the sieve bed creates a hammering effect on the sieve material, which can damage the granules and reduce them to dust, and whose escape from the system must be minimized. Excessive loss of sieve material is a failure mode itself and as more material is lost, the remaining material is freer to move within the sieve bed thereby accelerating relative motion and degradation to dusting.

A semi-permeable membrane, or filter-type media (e.g., 512, 514, 520, and 522) may be used to hold the sieve material in place while permitting the flow of gas through it. These membranes or filters can be of flexible construction and in that case, in need of mechanical support in order to retain pressurized granular media from motion and to a confined volume. In order to sufficiently support the filter media, some of the filter area must be occluded from flow by a supporting mechanical structure such as the prior art disc shown in FIGS. 4A and 4B. Often this structure has holes to permit gas flow while also providing mechanical support through the sold portions of the structure. The solid portions, however, do not permit gas flow.

With regard to a diffusor structure, there is a limit to the open area of individual holes and the total open area of the sum of the area of all holes. Individual hole area is limited by the mechanical properties of the filter media, which may cause the filter media to sag if the hole geometry (diameter in a round hole) is too great a span. The total open area is further limited by the stresses and mechanical properties of the sieve material and the ability of the sieve bed vessel walls to withstand static and cyclic loads. The geometry of the individual holes and the pattern of holes also significantly contributes to the energy losses and noise of the system by contributing to the pressure losses of the flowing gas. As will be further discussed herein, appropriate diffuser geometry can reduce energy losses if appropriate features of hole size, length of holes in the direction of flow, patterns of holes and solid area, orientation of holes and other hole features that affect flow are provided. This can include use of multiple diffusers as described above in connection with FIG. 3. In the case of multiple diffusers, each diffuser can have the same or different geometry in order to obtain the desired flow and structural properties. And, to the extent flow into the sieve bed, or out of the sieve bed during the exhaust cycle, is not uniform, there are other losses, which can be corrected or improved by the influence of flow-altering features or geometries at the face of the sieve bed by one or more diffusers and/or sieve caps/interfaces having flow modifying structures.

FIGS. 7A-7F illustrate various views of multiple embodiments of a diffuser 510 for a sieve bed. Diffuser 510 has low solidity thereby providing a substantially large open area for flow. Diffuser 510 also has structural strength to support a filter media and to transfer the force or bias of a spring to maintain the sieve material packed and resistant to mechanical movement within the sieve bed vessel walls. Diffuser 510 includes a body 700 having, in one embodiment, a honeycomb wall structure. Body 700 can have any appropriate size and shape including, for example, the disc shape shown in the Figures. In one example, the disc has a diameter of 2.44 inches and a height D2 of 0.5 inches. Other dimensions and shapes are also possible for the open areas including, for example, triangular, square, rectangular, other polygonal, circular (e.g., see body 800 in FIG. 8 having circular shaped walls 802 defining circular open areas 704), elliptical, etc.

Figure 7A:
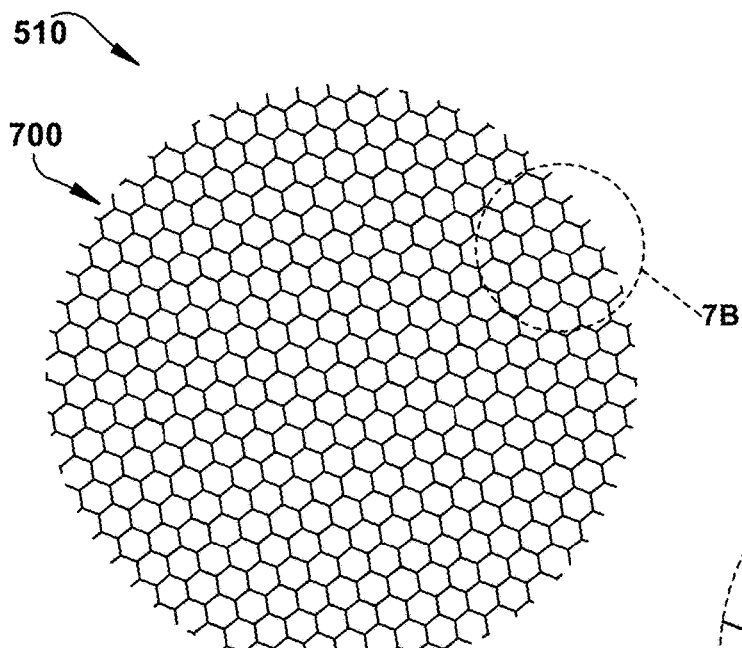
FIG. 7A-7F illustrate various views of multiple embodiments of a diffuser having a honeycomb structure.
Figure 7B:
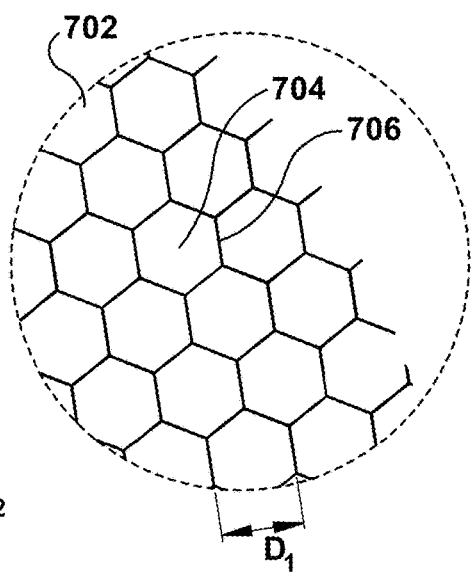
Figure 7C:
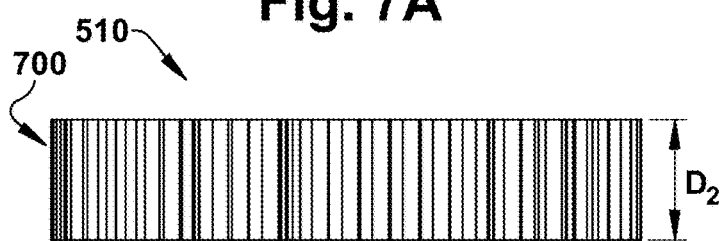
Figure 7D:
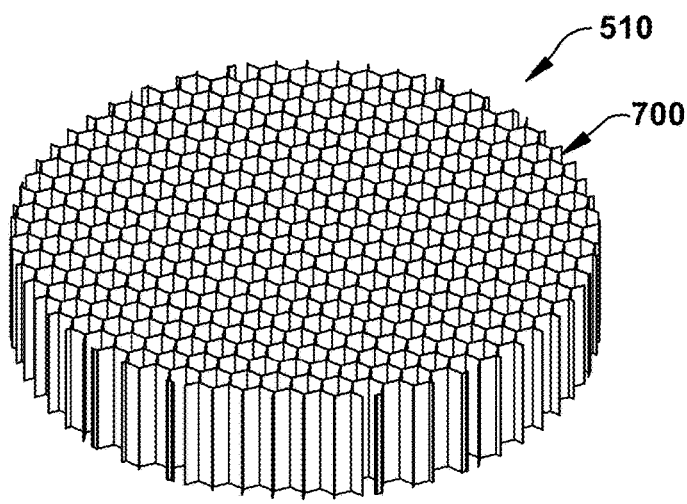
Figure 7E:
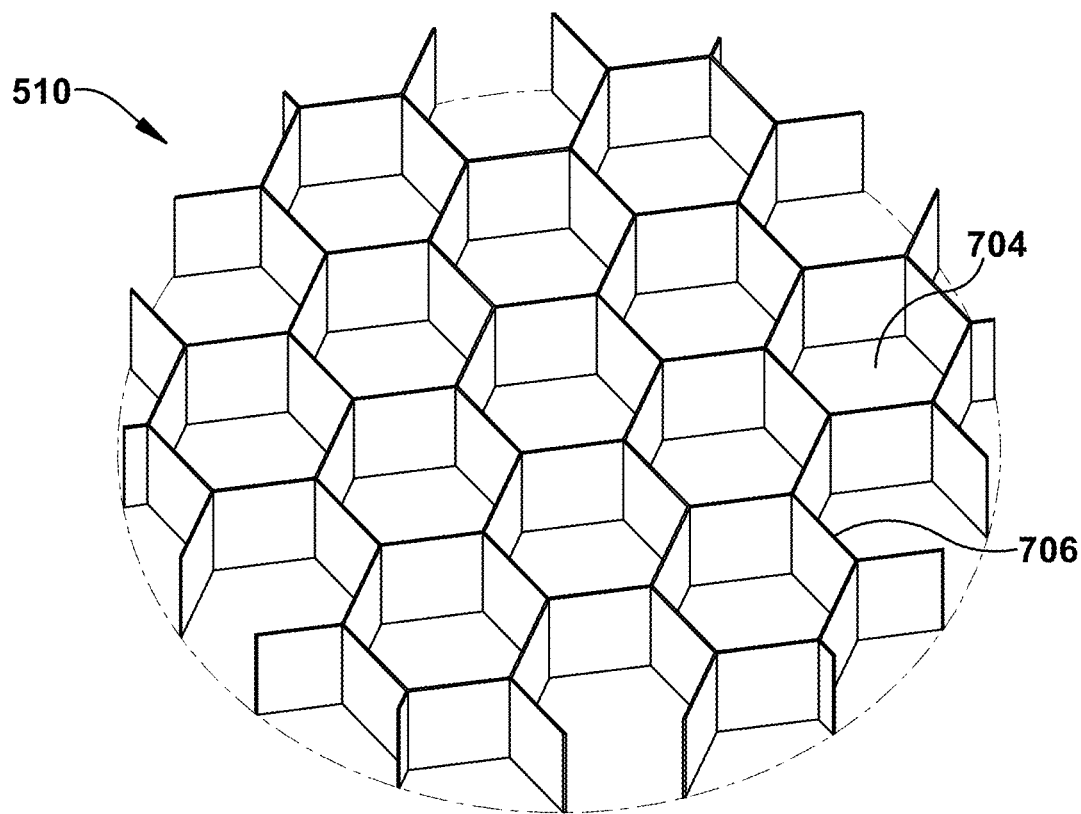
Figure 7F:
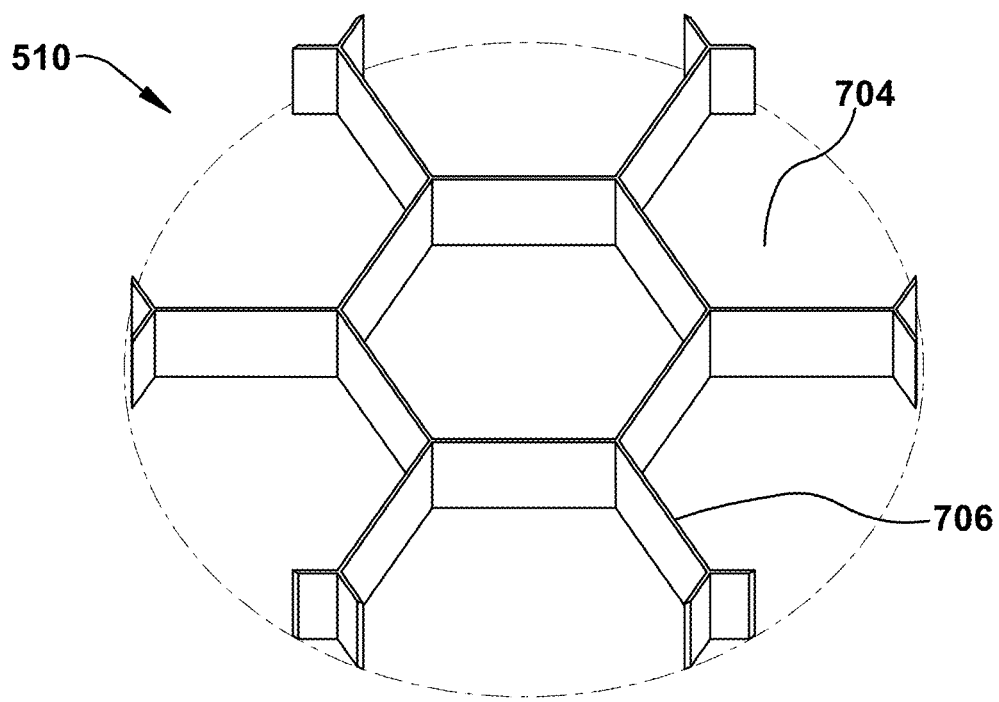
Figure 8:
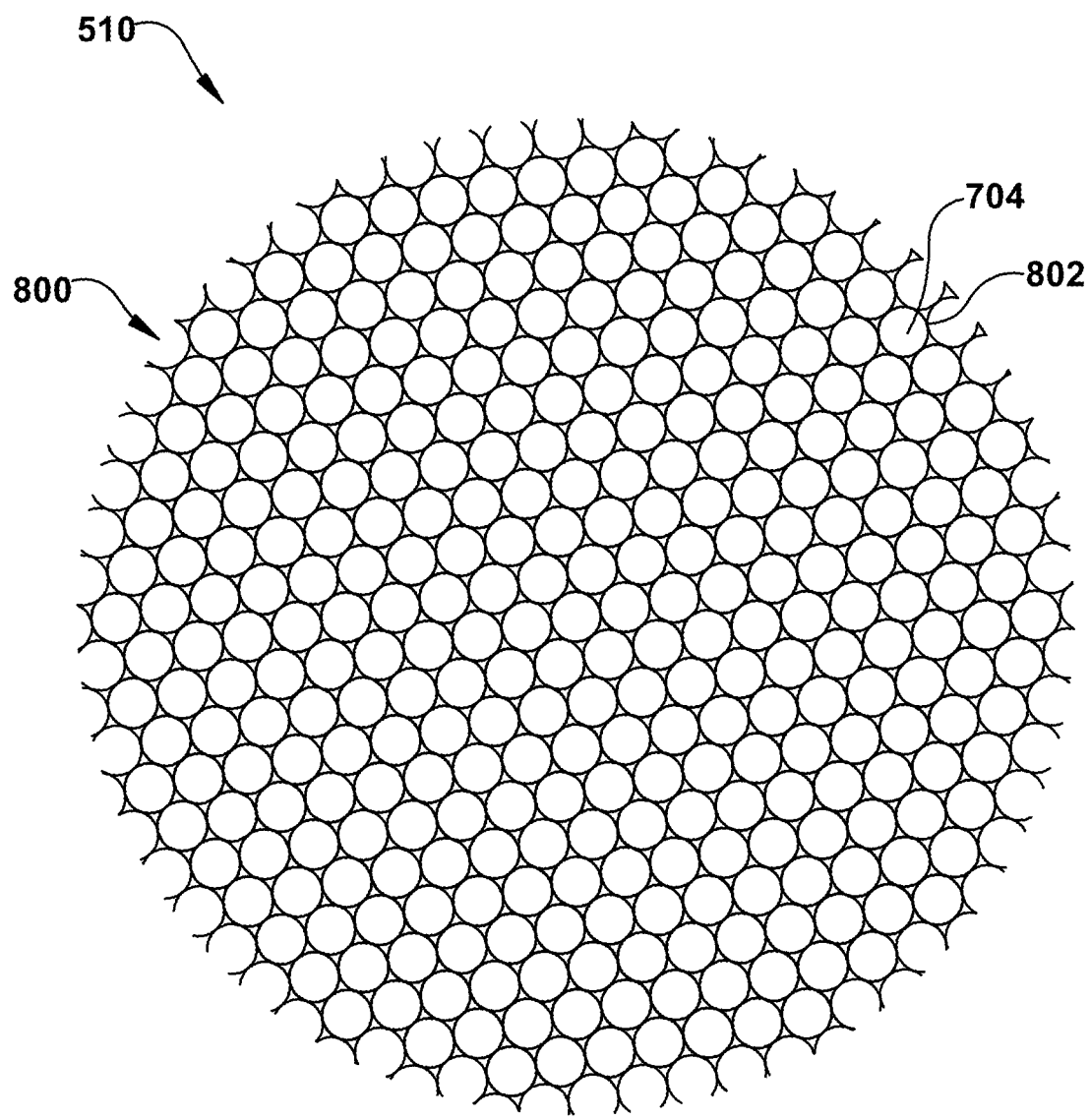
FIG. 8 illustrates a top view of a second embodiment of a diffuser having a cylindrical or straw-like structure.

As shown in the magnified view of FIG. 7B, walls 706 have a honeycomb (or hexagonal) arrangement that encloses an open space 704. The solidity (ratio of solid to open area) of diffuser 510 can be between more or less 0.10% to 50%. For example, in the one embodiment shown in FIGS. 7A-D, with a honeycomb cell size D1 equal to 0.125 inches and a wall 706 thickness equal to 0.001 inches, and a diffuser body diameter equal to 2.44 inches, a solidity of 2.46% is obtained. In another embodiment shown in FIG. 7E, with a honeycomb cell size D1 equal to 0.5 inches and a wall 706 thickness equal to 0.001 inches, and a diffuser body diameter equal to 2.44 inches, a solidity of 0.41% is obtained. In yet another embodiment shown in FIG. 7F, with a honeycomb cell size D1 equal to 1.0 inches and a wall 706 thickness equal to 0.001 inches, and a diffuser body diameter equal to 2.44 inches, a solidity of 0.17% is obtained. Ideally, while maximizing the open area of the diffuser is highly desirable, arrangements that improve/increase the open area over the prior art are also desirable and provide efficiencies. That is, maximizing the open area is not necessary for efficiencies to realized.

By varying the size of the subdivided channels and/or independently changing the length of the channels in the direction of flow, the characteristics of the diffuser flow stream can be modified with benefits of lower energy loss, more uniform flow entering the sieve bed, lower peak velocity at or near the face of the sieve material, lower bulk flow velocity in any part of the sieve bed, lower flow acceleration into the sieve bed, lower flow acceleration out of the sieve bed during exhaust cycle, lower force on the sieve material, less impact on sieve material from dynamic pressure or from lower peak-to-peak acceleration of bi-directional flow. Uniform flow or uniform pressure of flow entering sieve bed will reduce or eliminate flow within the sieve bed that is not parallel to the gross direction of flow through the sieve bed, which increases the distance air must travel to progress through the sieve material lowering the efficiency in time and oxygen production of the sieve. Similarly, on exit, non-uniform restrictions on exit pressure will cause flow to converge or diverge and be non-parallel to the gross direction of flow out of the sieve bed and therefore extending the duration of the exhaust/purge cycle and lowering the efficiency of the exhaust/purge cycle and the overall bi-directional (fill/purge) cycle.

Figure 9:
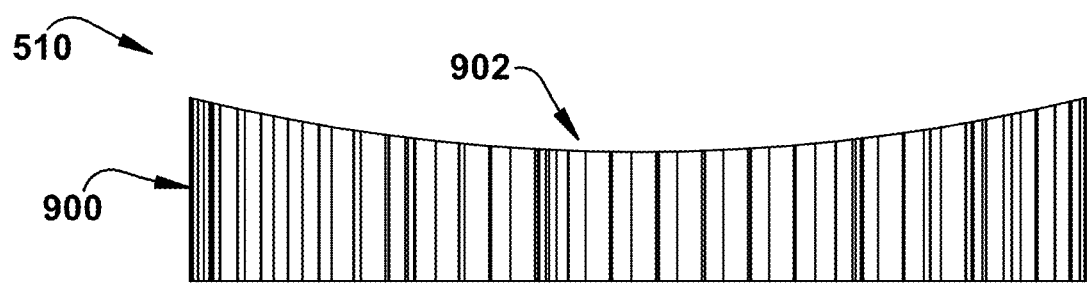
FIGS. 9-12 illustrates side elevational views of various embodiments of diffusers having different cross-sectional geometries and profiles.
Figure 10:
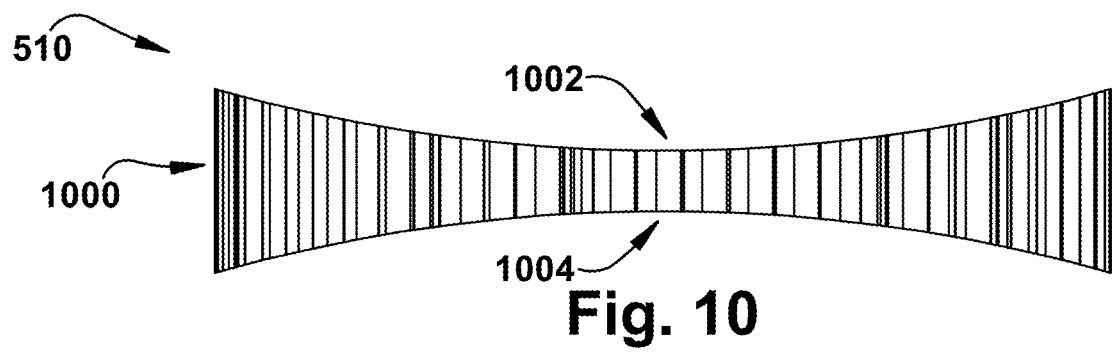
Figure 11:
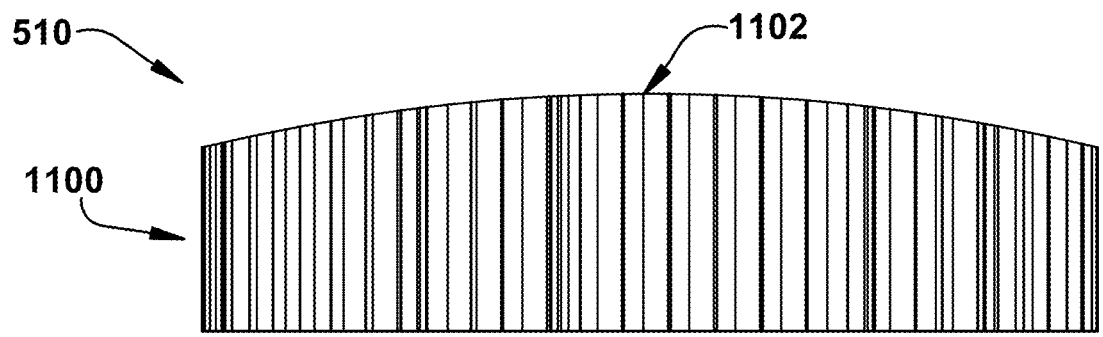
Figure 12:
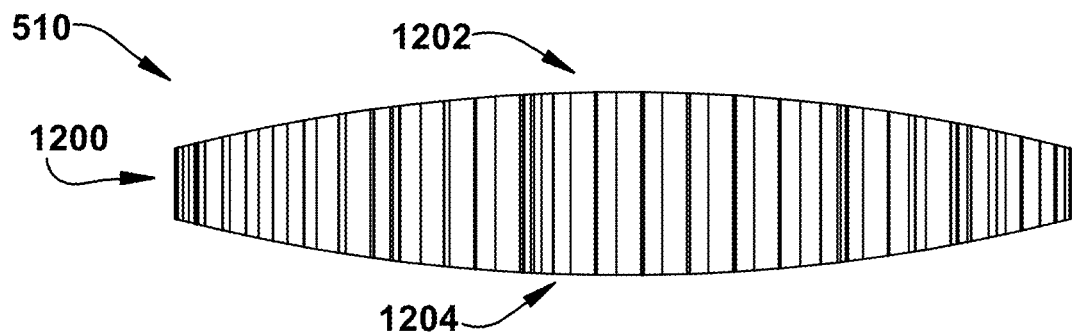

FIGS. 9-12 illustrate various embodiments of diffuser 510 cross-sectional body profiles. For example, FIG. 9 illustrates a body 900 having a first concave surface profile 902. FIG. 10 illustrates a body 1000 having first and second concave surface profiles 1002 and 1004. FIG. 11 illustrates a body 1100 having a first convex surface profile 1102. FIG. 12 illustrates a body 1200 having first and second convex surface profiles 1202 and 1204. The embodiments of FIGS. 11 and 12 provide the particular advantage of additional structural strength in their center sections due to the longer height of the diffuser walls and those portions. This resists bending and other undesired mechanical deformations. Other cross-sectional body profiles are also possible including, for example, wavy or undulating profiles, triangular, sawtooth, etc. Diffuser bodies can be made from any suitable material. This includes, for example, metals and plastics. Suitable metals include aluminum, and stainless steel. Diffuser bodies can also be formed via 3D printing techniques that allow for simple and complex space and wall arrangements including those disclosed herein.

The height (e.g., D2 in FIG. 7C) of the diffuser body or the various heights of the body cross-sectional profiles shown in FIGS. 9-12, reduce inefficiencies of flow by straightening the flow in and/or out of the sieve bed. They also reduce turbulence in the flow through the diffuser wall geometry (e.g., honeycomb, circular, etc.) and via the number of walls or channels. They also orient the inward and outward flows in the gross direction of the sieve bed to reduce the tangential or off-axis flows, which would direct the air molecules to travel a greater distance to progress into and/or traverse to exit the sieve bed. The height D2 or height of the cross-sectional profiles can be any height determined to improve the flow efficiency, including the varying heights shown and described in connection with FIGS. 9-12.

The height (e.g., D2 in FIG. 7C) of the diffuser body or the various heights of the body cross-sectional profiles shown in FIGS. 9-12, also provide a structural or retention component, as previously described. Namely, spring 506 applies a bias or force against the sieve material to keep it secured and free from movement through the diffuser (e.g., see FIGS. 6A-6B, for example). Ideally, the diffuser body is made from materials with adequate shear, tensile and cyclic fatigue properties to provide the mechanical support needed (e.g., to prevent sagging under load). Thus, optimized diffuser bodies that enlarge or maximize the cross-sectional area open to flow while still providing adequate mechanical strength for retention of sieve filter media and sieve material are possible in consideration of the properties of the diffuser body material and minimizing the interstitial volume of the diffuser body material.

Enlarging or maximizing the diffuser body open area can, in one embodiment, be linked with the mechanical properties needed for the retention function of the diffuser body. The diffuser body retention function relates to the diffuser body's ability to adequately support the filter media and sieve material in a packed state. In addition to potentially stronger body materials with higher shear, tensile and cyclic fatigue properties, a diffuser with very high percent of open area for flow compared to the total area available and therefore a low solidity ratio, could be created by using the optimal hole size based on the mechanical needs of the filter media (e.g. to avoid sagging under mechanical load), and packing the most number of holes by minimizing the interstitial volume of material by increasing the moment of inertia of the mechanical design in the direction of flow.

The use of diffuser 510 shown in FIGS. 7A-7D has shown that the separation process can be made more efficient by lowering the peak velocity of gas entering the sieve bed (i.e., near or at the face of the sieve material) while still obtaining conventional gas separation results. Conventional peak velocities of up to 168.6 inches/sec were reduced to 70.1 inches/sec, which is a reduction of approximately 60%. A lowering of the peak velocity of gas entering the sieve bed translates into many practical advantages. For example, less energy is needed to operate the gas separation process due to the lower peak flow rates. Lower peak flow rates also mean that compressors do not have to work as hard thereby reducing component wear and extending compressor life. Furthermore, reduced peak velocities decrease the pressure or mechanical forces within the sieve material and therefore reduce dusting and mechanical failure of the sieve material by reducing relative movement of the sieve bed materials. It also reduces the dynamic force on the face of the sieve bed, on the sieve filter(s) and/or on the sieve material thereby reducing sieve bed material mechanical degradation. Further yet, reduced peak velocities lower the noise caused by airflow within the system.

Efficiencies are also obtained by the diffuser spaces/channels having a height/length (e.g., D2 in FIG. 7C), which straightens flow into and out of the sieve material. Straightening the flow also reduces inefficiencies by reducing turbulent flow within the diffuser and/or caused by the diffuser at the face of the sieve material. Straightening the flow also orients the inward and outward flows in the gross direction of the bed, to reduce the tangential or off-axis flows, which would direct the air molecules to travel a greater distance to progress into or traverse to exit the sieve bed. The disclosed diffuser arrangements also provide mechanical support for any retaining mechanism for sieve material that must be in the flow path. The overall result is a gas separation system having lower energy consumption, greater oxygen output, or specific output (oxygen produced per unit of energy input), higher reliability defined by the life of the sieve bed against dusting, and lower noise. While all of the benefits and advantage can be obtained, any one or more is sufficient to provide an improved gas separation process.

In another embodiment, systems and methods are provided having an indicator when a component has been serviced or repaired. In one embodiment, the indicator provides a visual indication if the component has been tampered with in any manner. This allows the manufacturer to determine if the component was serviced, repaired, or tampered with outside the manufacturer's domain. Unauthorized service or repair could result in premature component wear and failure.

Figure 13:
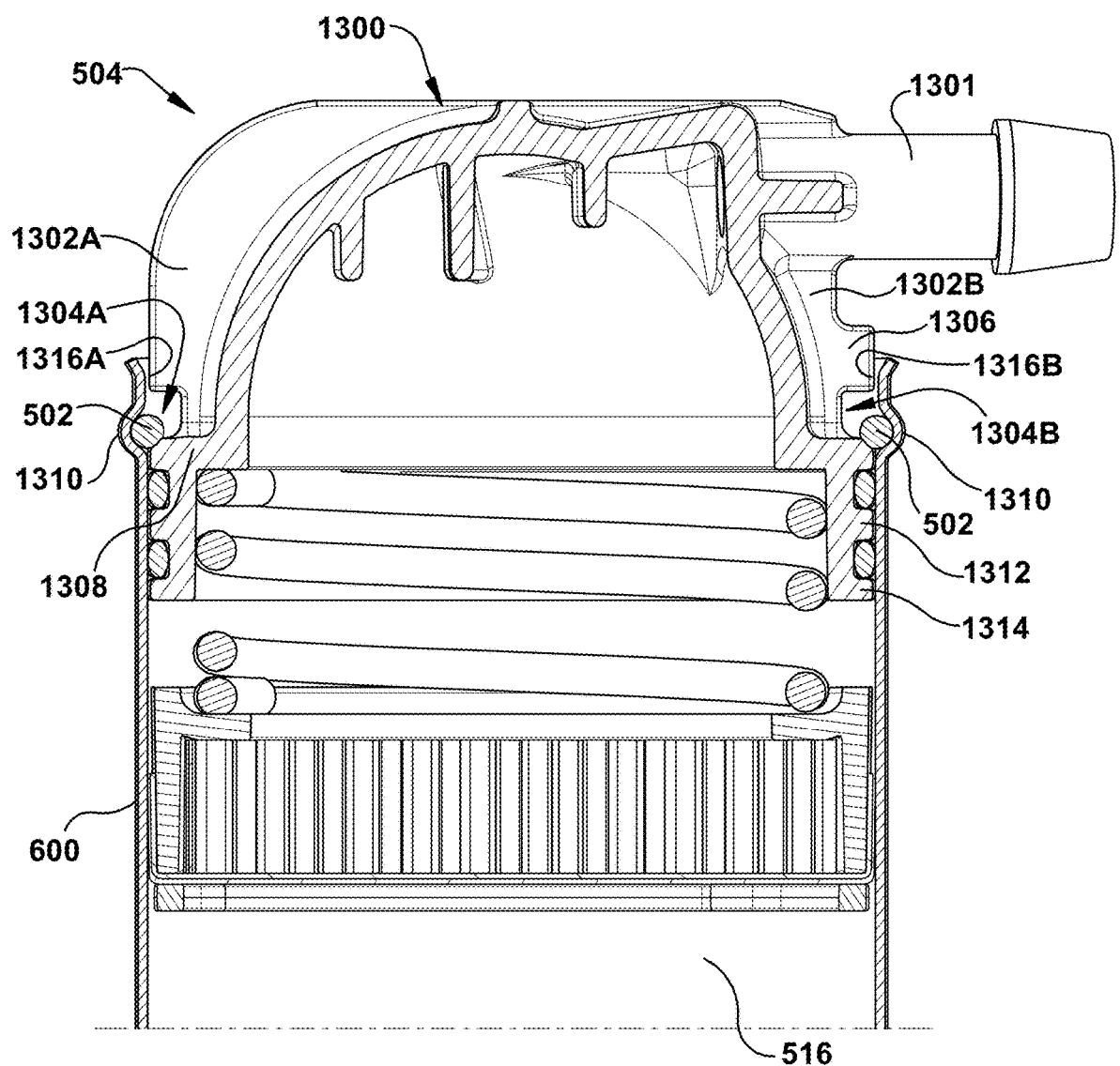
FIG. 13 illustrates the partial cross-sectional view of one embodiment showing an anti-tamper feature.

Illustrated in FIG. 13 is one embodiment of a system having an anti-tamper feature or arrangement. FIG. 13 shows a magnified, partial, cross-sectional view of the top portion of the sieve bed from FIGS. 6A-6B. The sieve bed includes an anti-tamper feature or arrangement that provides a visual indication if the sieve bed has been opened to, for example, replace the sieve material. The sieve material 516 is a component which needs to be replaced over time. This is because the sieve material 516 degrades over time due to, for example, dusting or mechanical degradation, moisture, saturation wear, etc. Typically, sieve material 516 needs to be replaced approximately every 18 months. The unauthorized replacement of the sieve material 516 with material not authorized by the manufacturer could cause dusting and premature failure of other gas separation components. The arrangement shown in FIG. 13 provides a visual indication if the sieve bed has been opened.

While FIG. 13 illustrates an example where one anti-tamper cap 504 is associated with a single sieve bed vessel 600, in other embodiments a common anti-tamper cap 504 (acting akin to a manifold) may be used a sieve bed vessel assembly having more than one sieve bed vessel. In yet other embodiments, a sieve bed vessel 600 may use more than one anti-tamper cap 504.

Still referring to FIG. 13, the anti-tamper cap 504 of the sieve bed includes a body 1300. Body 1300 includes one or more ribs 1302A-D (see also FIG. 14A). The ribs include recesses or spaces 1304A-D. The recesses, along with rim 1308, are arranged to receive and secure retaining ring or clip 502, which is designed to retain cap 504 to the sieve bed vessel wall 600. Sieve bed vessel wall 600 also includes an annular recess 1310 for receiving and securing a portion of retaining ring 502. Ribs 1302A-D also include outer surfaces or walls having a portions 1316A-D arranged to contact or nearly contact vessel wall 600. In this manner, retaining ring 502 cannot be removed unless one or more rib portions 1316A-D are tampered with (e.g., cut, damaged, destroyed or otherwise modified) to allow retaining clip 502 to be removed. Tampering with rib portions 1316A-D provides a visual indication through visible damage thereto that the sieve bed has likely been opened. Furthermore, tampering with rib portions 1316A-D will also likely result in visual damage to the sieve vessel wall 600 in those locations. Further yet, damage to rib portions 1316A-D and/or the sieve vessel wall 600 and those locations will likely result in irreparable damage to cap 504 and/or sieve bed vessel wall 600. The net result is to discourage tampering or unauthorized servicing of the sieve bed because it will likely be irreparably damaged.

Figure 14A:
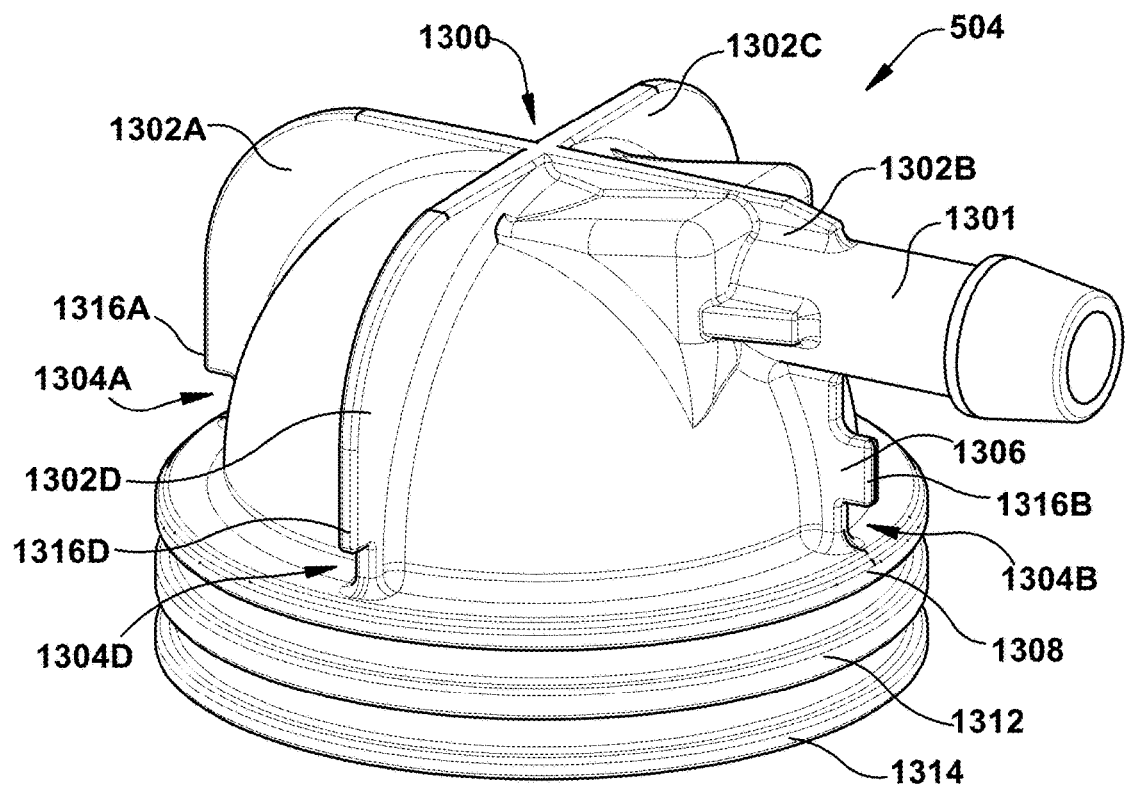
FIGS. 14A-B illustrate perspective and elevational views of one embodiment of a sieve bed cap including an anti-tamper feature.
Figure 14B:
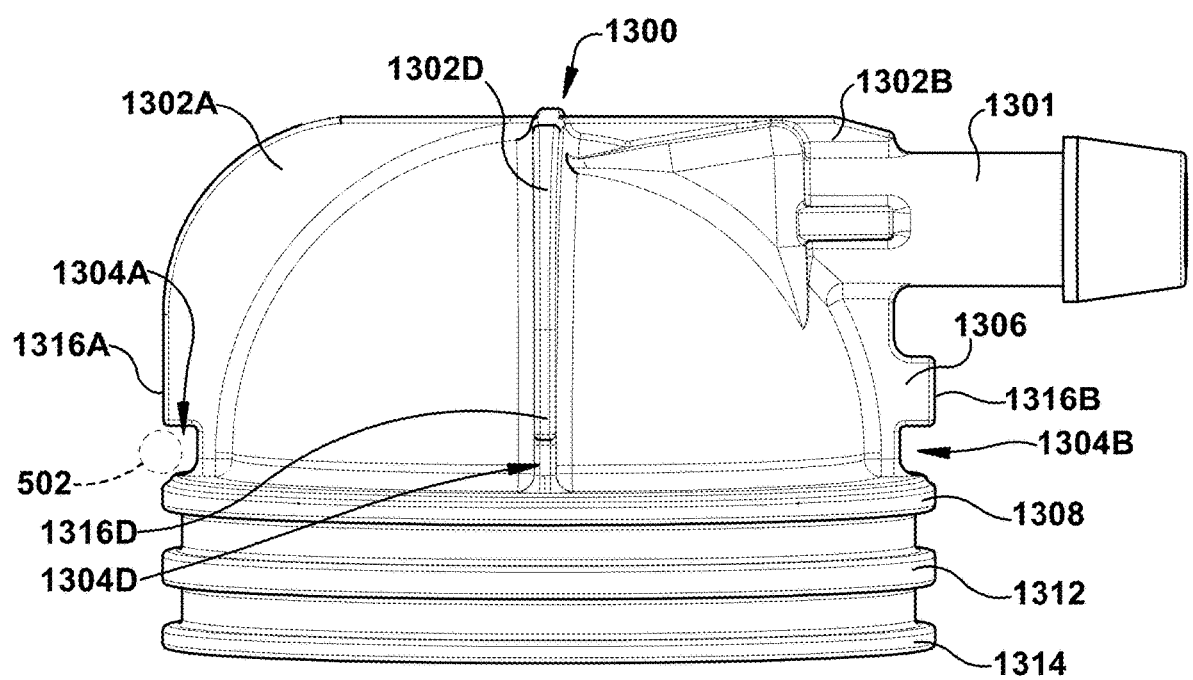

FIGS. 14A-B illustrate perspective and side elevational views of the embodiment of the cap 504 shown in FIG. 13. As described above, the cap body 1300 includes four ribs 1302A-D and each rib includes recesses or spaces (e.g., 1304A-D) for receiving and securing a portion of retaining ring 502. Each rib 1302A-D also includes one or more wall portions or surfaces (e.g., 1316A-D) arranged to contact or nearly contact a portion of the sieve bed vessel wall 600 in those locations. Contact with the sieve bed vessel wall 600 in those locations is not necessary so long as any gap created is small enough to restrict removal of retaining ring 502. Body 1300 further includes spaced apart rims 516 and 1314 (along with rim 1308) for retaining gaskets or O-rings and creating an interference fit that retains cap body 1300 to sieve bed vessel wall 600. Rims 1308, 1312, 1314 are not a necessary part of the anti-tamper feature but can be modified to be included as well.

It should be noted that in other embodiments, cap body 1300 can include less than four ribs 1302A-D and that each rib need not have walls and recesses for securing retaining ring 502. It is sufficient that at least one rib contains these features. Further, the geometry of the ribs, walls, and recesses can be modified from that shown in the embodiments herein so long as portions are provided in the cap body 1300 to secure retaining ring 502 from easy removal (e.g., removal without creating a visual indicator such as, for example, physical damage or modification to the cap body 1300 and/or sieve bed vessel wall 600). For example, cap body 1300 can include a projecting member or tab 1306 which is adjacent recess 1304B. Projecting tab 1306 can be a component of rib 1302B or a separate component thereon on its own. While one projecting tab 1306 is shown, more than one can be provided as a component of ribs 1302A-D. In yet other embodiments, ribs 1302A-D can be eliminated and in their place a plurality of projecting tabs, such as tab 1306, used in the same locations as ribs 1302A-D, or in more locations, to accomplish the same results. In yet other embodiments, multiple tabs, such as tab 1306, can be used with one or more ribs. The number, geometry and shape are not critical so long as the projecting member (e.g., ribs, tabs, and combinations thereof) at least partially enclose the retaining ring in the manner described herein to discourage tampering and/or provide a tamper indicator.

Figure 15A:
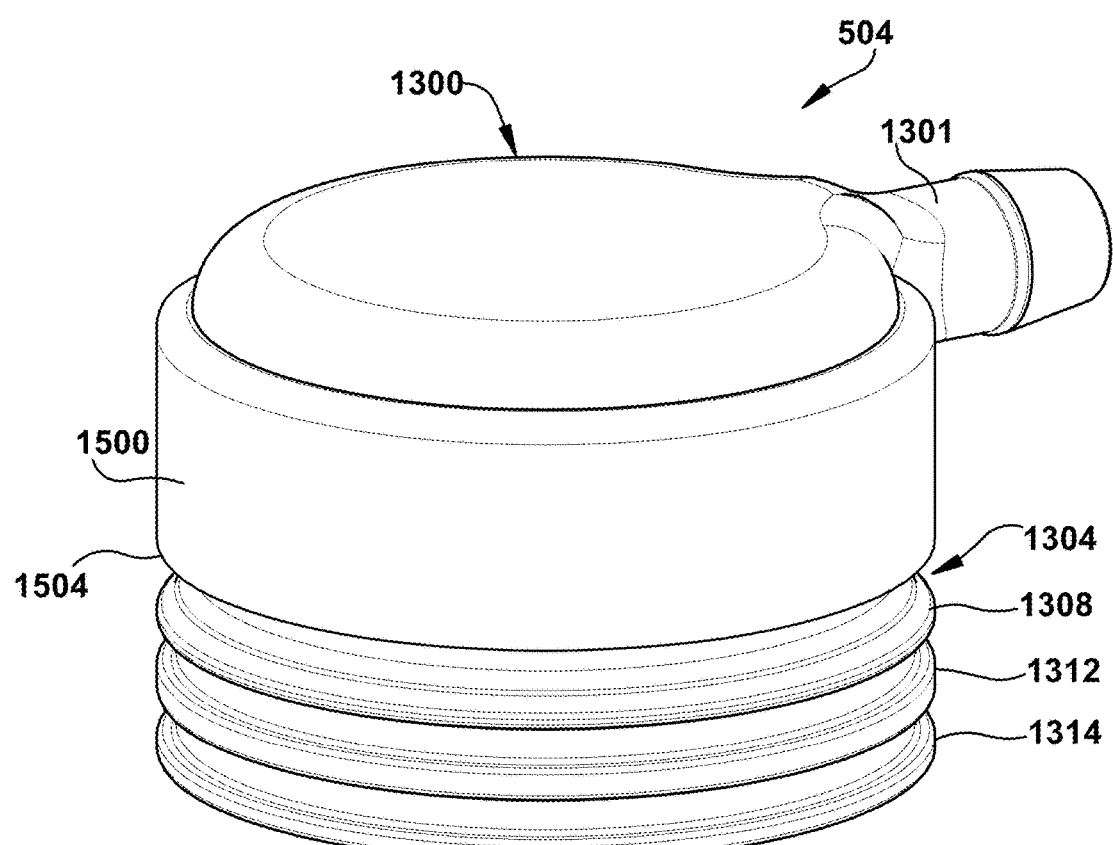
FIGS. 15A-B illustrate further embodiments of sieve bed caps having an anti-tamper feature.
Figure 15B:
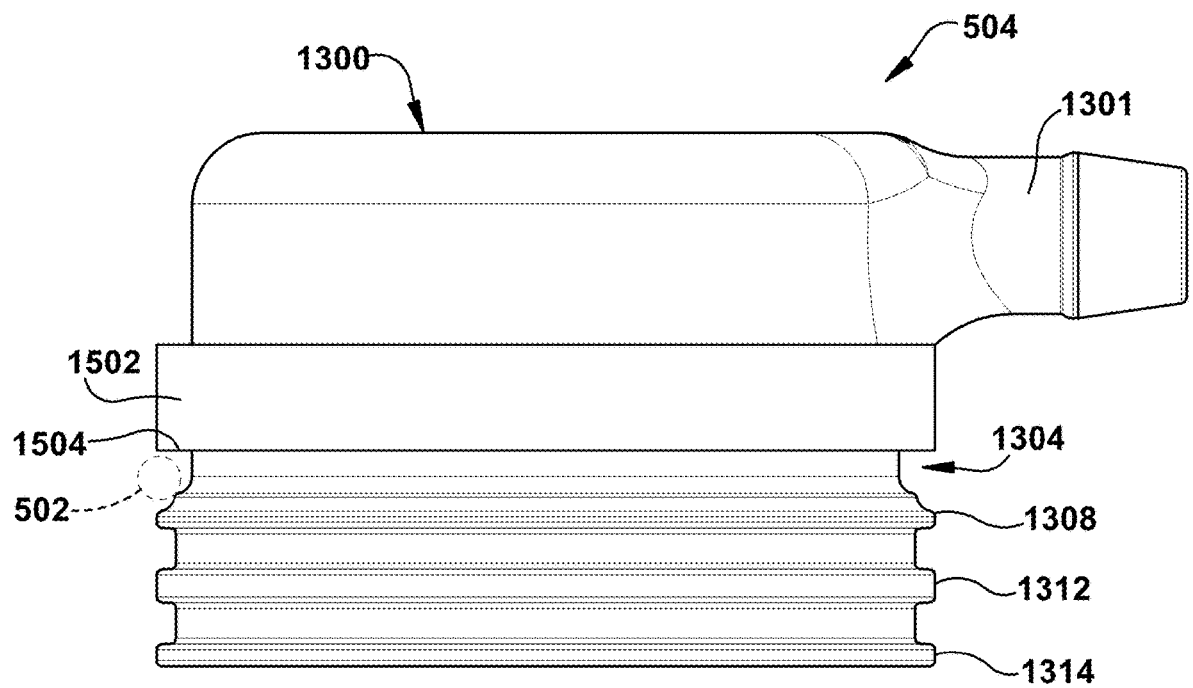

FIGS. 15A-B illustrate other embodiments of sieve caps having anti-tamper features. This includes rib-less sieve cap designs. In one embodiment, the sieve cap body can include a revolved dome of various configurations. FIG. 15A illustrates one embodiment of a rib-less sieve cap body 1300. The body includes cylindrical surface 1500 that is horizontally revolved (e.g., versus having individual vertically disposed ribs), projects or extends from the body 1300, and is arranged having edge portion 1504 in a similar manner to wall portions 1316A-D of FIGS. 13-14B contacting or very nearly contacting sieve vessel wall 600 to secure retaining ring or clip 502. FIG. 15B shows another embodiment of rib-less sieve cap body 1300 having a lesser or smaller cylindrical surface 1502 compared to that of FIG. 15A. Cylindrical surface 1502 is also arranged having edge region 1504 to contact or nearly contact sieve vessel wall 600 in a similar manner to wall portions 1316A-D of FIGS. 13-14B to secure retaining ring or clip 502. The remaining features of the sieve cap bodies are similar to those already described in FIGS. 13-14B. Thus, rib-less walls/surface 1500 and 1502 secure retaining ring/clip 502 in the same manner as wall portions 1316A-D, but along a greater perimeter than by using individual ribs 1302A-D. Attempted removal of retaining ring or clip 502 from the embodiments of FIGS. 15A and 15B will result in damage to edge or perimeter portion 1504 that secures the retaining ring or clip 502 to thereby provide a tamper indication. Thus, the sieve cap bodies disclosed herein are not limited to ribbed anti-tamper features and include both ribbed and/or rib-less arrangements.

FIGS. 16A-D illustrate another embodiment of a sieve bed cap 504 having an anti-tamper feature. In this embodiment, the cap 504 includes one or more structural portions that rupture or break upon attempted removal of the retaining ring or clip 502 thereby rendering cap 504 no longer re-usable. This is accomplished by creating one or more weakened portion(s) in body 1300.

Figure 16A:
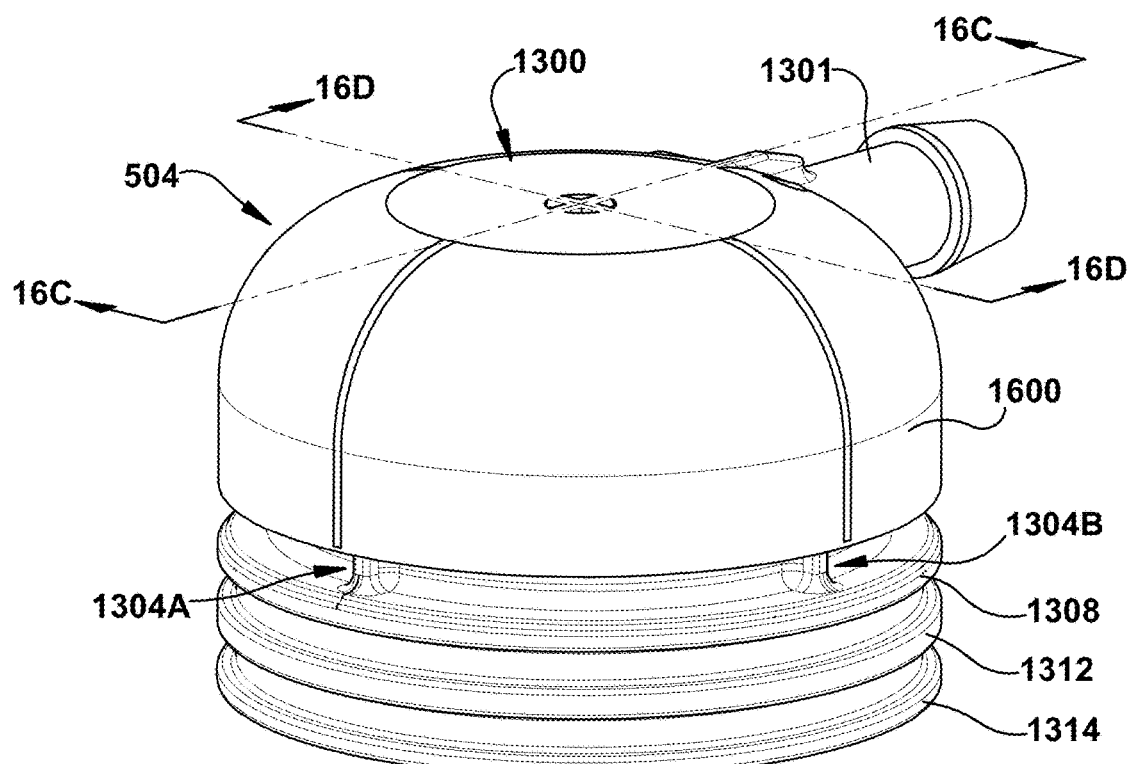
FIGS. 16A-16D illustrate yet another embodiment of a sieve bed cap having an anti-tamper feature.
Figure 16B:
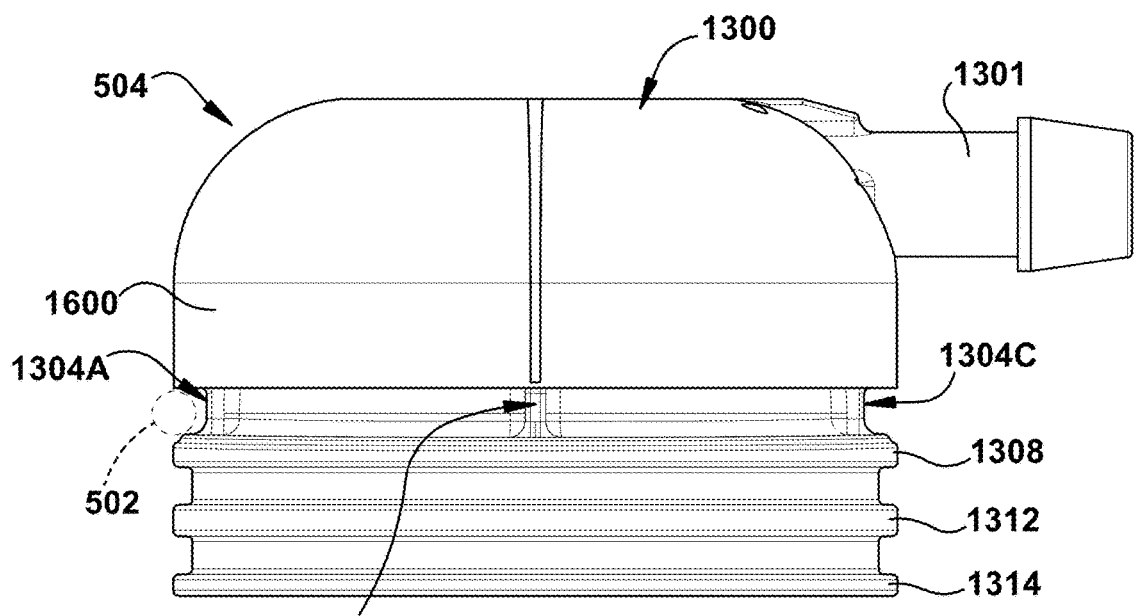
Figure 16C:
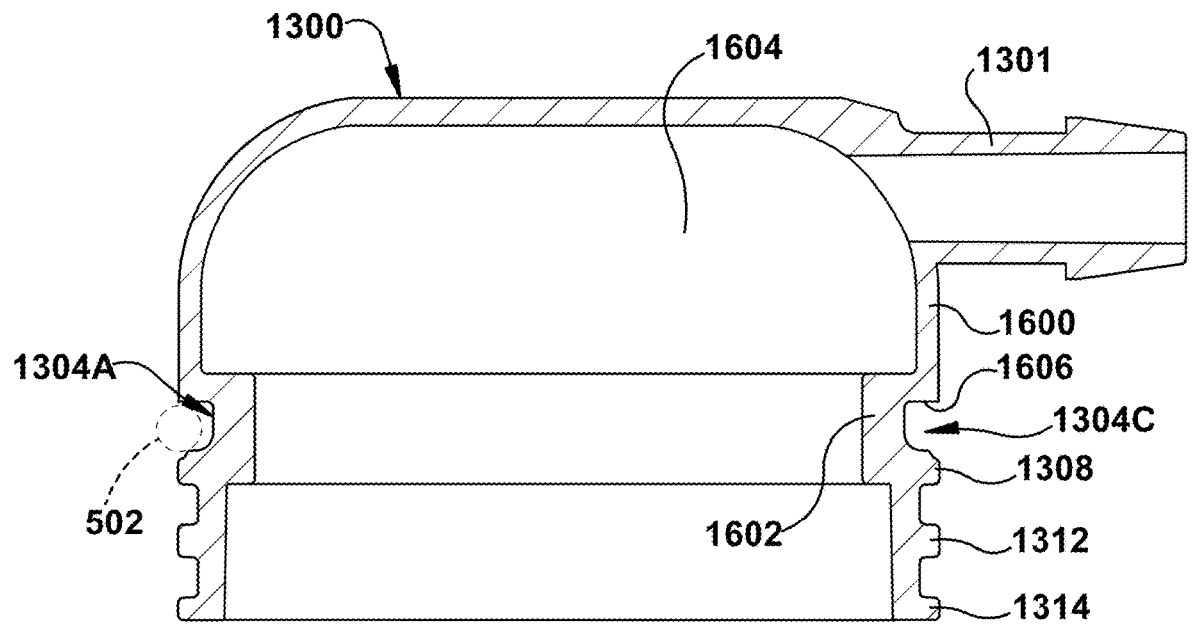
Figure 16D:
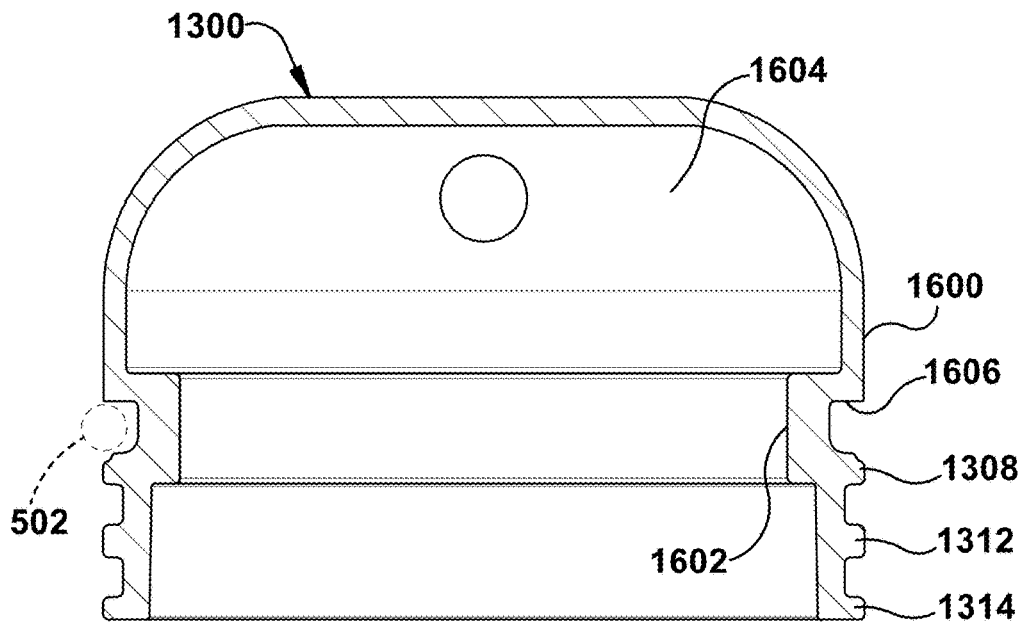

In the embodiment shown, body 1300 includes a dome portion 1600 that is arranged to partially or completely break off upon attempted removal of retaining ring or clip 502. A partial or complete break or rupture defeats, among other things, the ability of interior space 1604 to properly function with the required operational sieve bed pressures, which effectively disables the gas separation system. Referring to FIGS. 16C and 16D, body 1300 includes recesses or spaces 1304A-D for at least partially securing retaining ring or clip 502. Recesses or spaces 1304A-D are bound on one side by perimeter wall 1602 of body 1300. As shown in FIG. 16C, wall 1602 has a first wall thickness where it bounds recesses or spaces 1304A-D. As shown in FIG. 16D, where perimeter wall 1602 does not bound recesses or spaces 1304A-D, wall 1602 has a second thickness that is less than the first thickness shown in FIG. 16C. The difference in thickness can be any difference that makes wall 1602 more susceptible to rupturing or breaking upon attempted removal of retaining ring or clip 502. In one embodiment, the thickness difference can be more or less than 25% to 90%. The precise thickness difference is not critical so long as a portion(s) of the sieve bed cap ruptures or breaks upon attempted removal of retaining ring or clip 502.

In another embodiment, lower dome perimeter wall 1606, which is adjacent wall 1602, can have different thickness portions in the same manner as described for wall 1602 to accomplish the same rupturing or breaking result. That is, the portion of wall 1606 shown in FIG. 16C can have a first thickness that is larger than the portion of wall 1606 shown in FIG. 16D. In this manner, the smaller thickness of the portion of wall 1606 shown in FIG. 16D is arranged to rupture or break upon attempted removal of retaining ring or clip 502. Other arrangements of cap 504 having portions arranged to breach, rupture or break can also be used to prevent unauthorized access to the sieve bed and/or re-use of tampered sieve beds and caps.

The caps 504 can, in one embodiment, be made of polycarbonate or other plastics and/or thermoplastics. The material composition can be any composition that allows for structural portions that rupture or break upon attempted removal of the retaining ring or clip 502 thereby rendering cap 504 no longer re-usable. This can further include metals, alloys, ceramics, and other moldable, printable and/or machinable materials.

Another factor that can contribute to sieve bed wear and tear, including dusting and fluidization of the sieve bed material, is non-uniform flow distribution and velocity of the gas (e.g., air) entering the sieve bed material. Air is typically input into a sieve bed via a cap or other input interface. The internal chamber geometry of the cap/interface may result in non-uniform flow distributions and/or concentrated regions of high flow velocity for the gas entering the sieve bed material. These undesirable effects can be addressed by using flow modifying structures, partitions, and/or projections to obtain more uniform and/or optimized flow distributions and flow velocities of the gas entering the sieve bed material. Various embodiments of sieve bed caps/interfaces for modifying the flow distribution and/or flow velocities of gas entering the sieve bed material are shown in FIGS. 17A-27B.

Figure 17A:
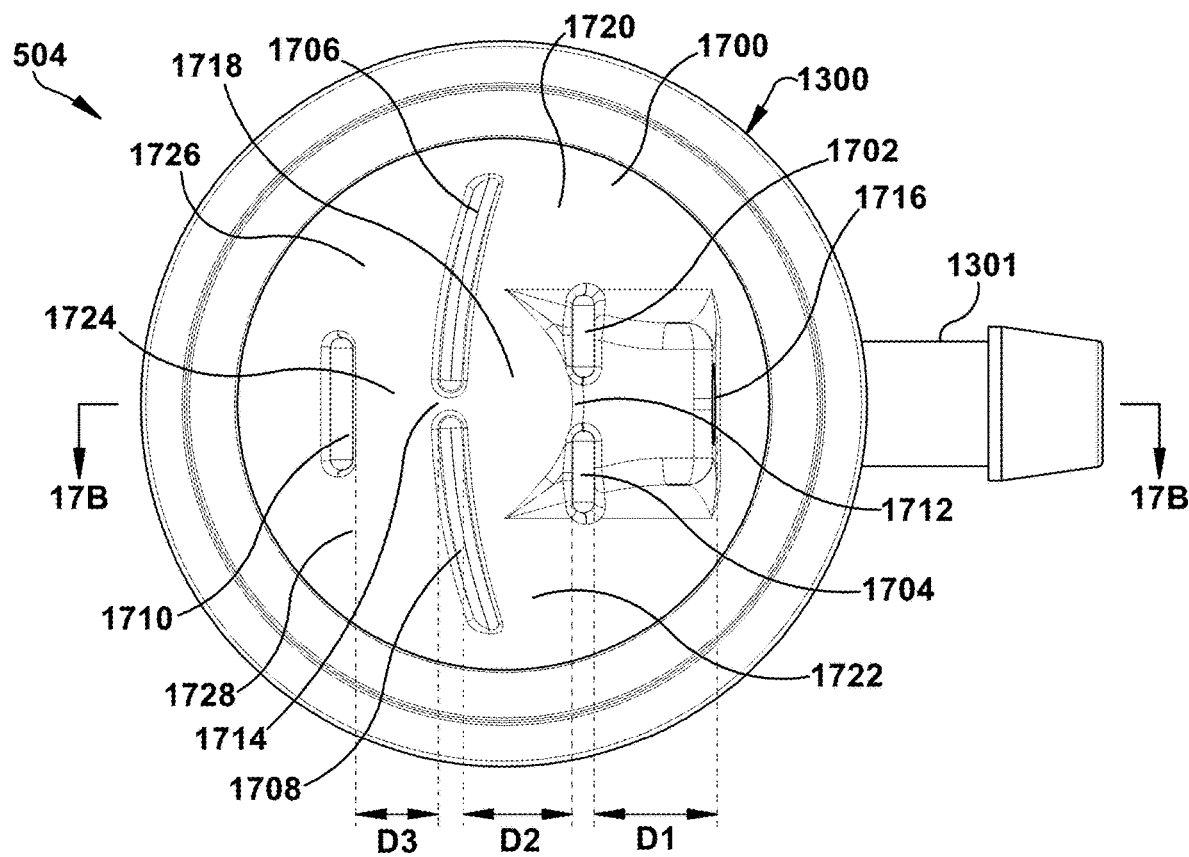
FIGS. 17A-17I illustrate one embodiment of a sieve bed cap for generating a desired flow profile.

Referring now to FIGS. 14A, 14B, and 17A-17B, one embodiment of a sieve bed cap/interface 504 having flow modifying structures, partitions, and/or projections is shown. Referring now to the bottom view of FIG. 17A, body 1300 includes an inner chamber geometry having a hemi-spherical or dome shaped wall or surface 1700 and first flow modifying structures 1702 and 1704, second flow modifying structures 1706 and 1708, and third flow modifying structure 1710. A first gap 1712 is located between the first flow modifying structures 1702 and 1704. A second gap 1714 is located between second flow modifying structures 1706 and 1708. In the present embodiment, the flow modifying structures are generally arranged in three spaced apart rows from gas port 1716, which feeds gas into the chamber. First flow modifying structures 1702 and 1704 are appositioned in proximity to gas port 1716 by a first distance D1, which can be approximately 0.45 inches (FIG. 17A is shown magnified to scale). Second flow modifying structures 1706 and 1708 are spaced apart from first flow modifying structures 1702 and 1704 by a distance D2, which can be approximately 0.42 inches. Third flow modifying structure 1710 is spaced apart from second flow modifying structures 1706 and 1708 by a distance D3, which can be approximately 0.33 inches. In other embodiments, these distances can be changed without substantially altering the flow modifying results.

The flow modifying structures 1702-1710 are, in one embodiment, baffles or ribs that deflect incoming gas from port 1716. As shown in FIG. 17A, first flow modifying structures 1702 and 1704 and third flow modifying structure 1710 have substantially flat bodies with rounded or curved end faces. Second flow modifying structures 1706 and 1708 have curved bodies with curved end faces. The curved bodies of structures 1706 and 1708 are shown in this embodiment to curve in a general direction toward gas port 1716. In other embodiments, the amount of flatness and curvature of any of these structures can vary from that shown without substantially affecting the flow modifying results.

Figure 17B:
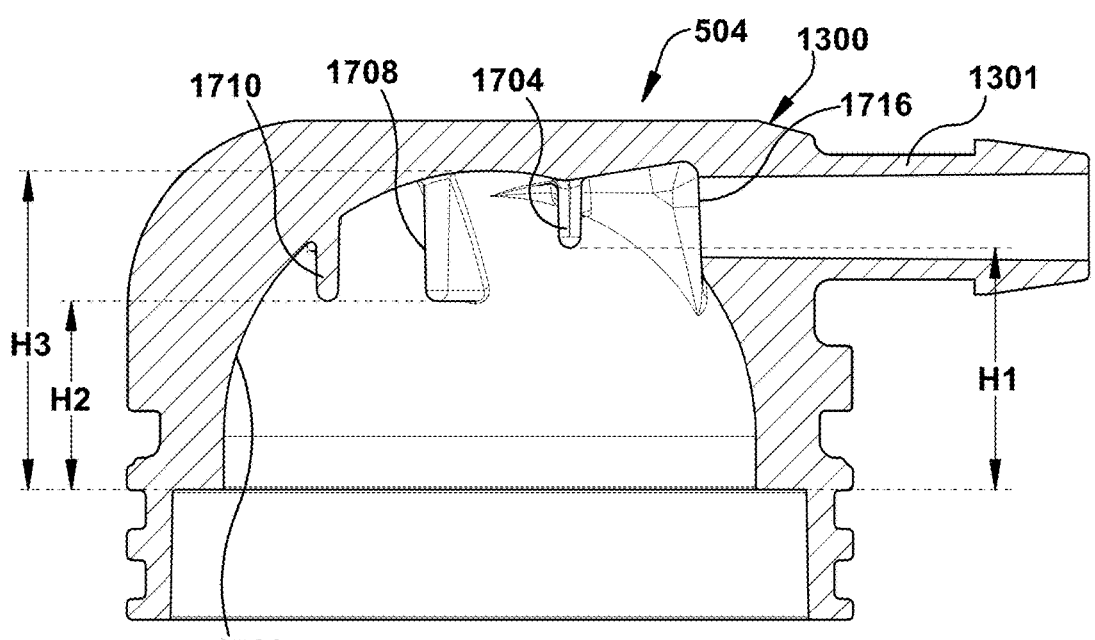
Figure 17C:
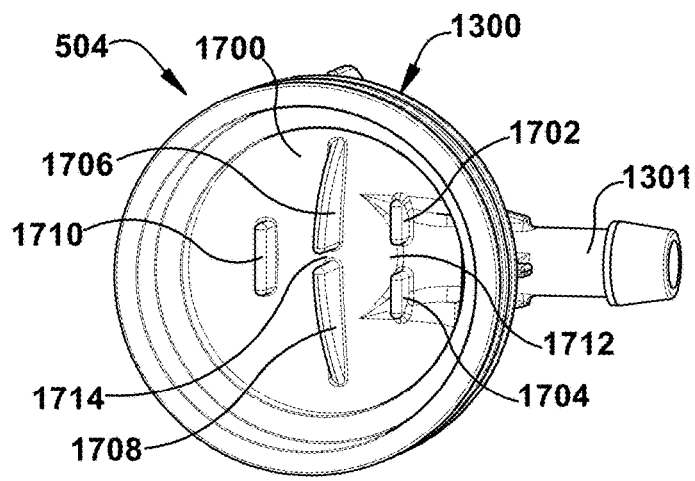
Figure 17D:
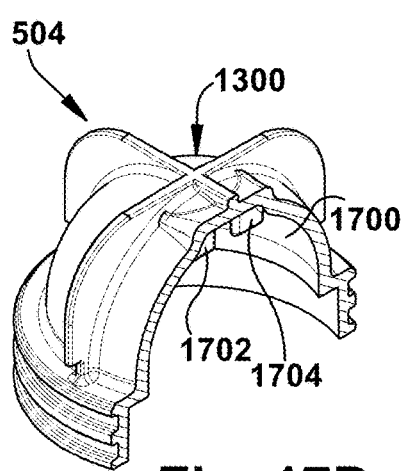
Figure 17F:
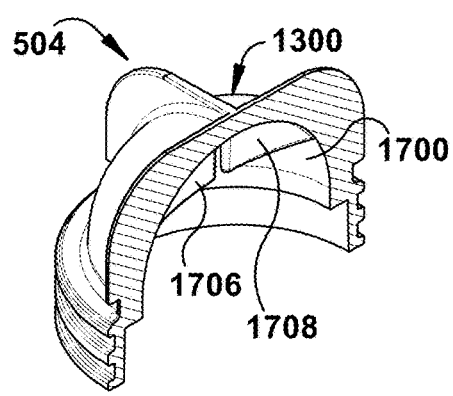
Figure 17H:
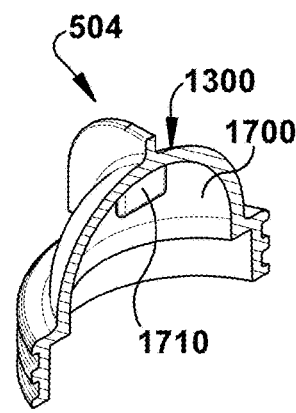
Figure 17E:
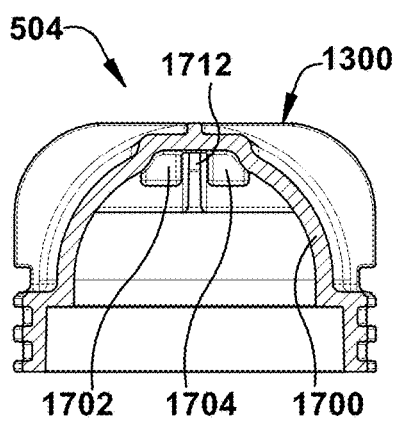
Figure 17G:
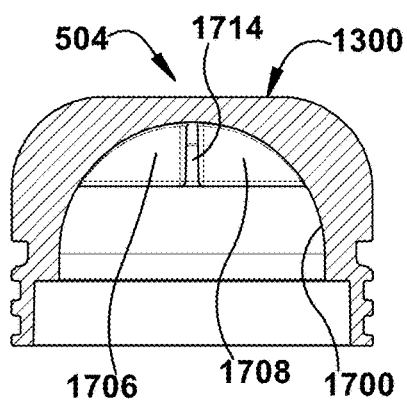
Figure 17I:
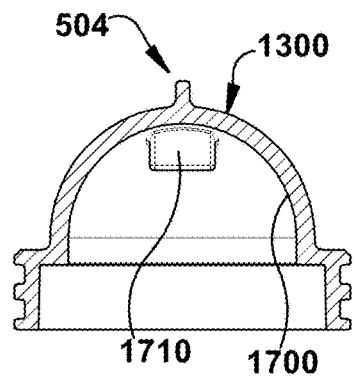

Referring now to FIG. 17B, a cross-sectional view of FIG. 17A is shown to relative scale. Each of the bodies of the flow modifying structures 1702-1710 extend a distance downward from wall 1700 and into the chamber. The internal chamber has a height H3 as shown, which can be approximately 1.2 inches. First flow modifying structures 1702 and 1704 extend downward to a height H1 as shown, which can be approximately 0.91 inches. Second and third flow modifying structures 1706, 1708 and 1710 extend downward to a height H2 as shown, which can be approximately 0.71 inches. In other embodiments, these dimensions can be varied without substantially affecting the flow modifying results. FIG. 17C is a bottom perspective further illustrating the size, location, and shape of the flow modifying structures 1702-1710 and gaps 1712 and 1714. FIG. 17D is a sectional perspective of the sieve bed cap and FIG. 17E is the associated cross-sectional view of FIG. 17D showing first flow modifying structures 1702 and 1704 and gap 1712. FIG. 17F is another sectional perspective and FIG. 17G is the associated cross-sectional view of FIG. 17F showing second flow modifying structures 1706 and 1708 and gap 1714. And, FIG. 17H is another sectional perspective and FIG. 17I is the associated cross-sectional view of FIG. 17H showing third flow modifying structure 1710.

Referring now back to FIG. 17A, gas is fed into the chamber from port 1716 and encounters first flow modifying structures 1702 and 1704 and gap 1712. This provides a first flow modification to the gas where a portion passes through gap 1712 and into space 1718 and other portions are deflected to spaces 1720 and 1722 where they encounter domed surface 1700. The gas flow then encounters second flow modifying structures 1706 and 1708 and gap 1714 where a smaller portion of the gas passes through gap 1714 and other portions are directed to spaces 1720 and 1722 and encounter domed surface 1700. In the embodiment shown, gap 1714 is smaller than gap 1712, thereby allowing less gas to pass therethrough compared to gap 1712. In other embodiments, gap 1714 can be about 0.1 to 1.0 times the size of gap 1712. In other embodiments, gap 1712 can be correspondingly smaller than gap 1714. Second flow modifying structures 1706 and 1708 by virtue of their shape deflect a portion of the gas inward to gap 1714 and a portion of the gas outward toward spaces 1720 and 1722. This provides a further, or second flow modification, to the gas flow. The gas flow then encounters the third flow modifying structure 1710. This causes the gas to deflect to spaces 1726 and 1728 where domed surface 1700 is encountered. FIG. 18B, discussed infra, illustrates these flow patterns through a computational fluid dynamics simulation.

Hence, the gas flow can be incrementally modified through each row of structures or baffles in order to obtain a desired flow distribution and/or velocities of the gas entering the sieve bed material. This provides for optimization of the flow to obtain more uniform distribution and flow velocity as the gas enters the sieve material to thereby reduce wear and tear (e.g., dusting, fluidization, etc.) of the sieve material.

Figure 18A:
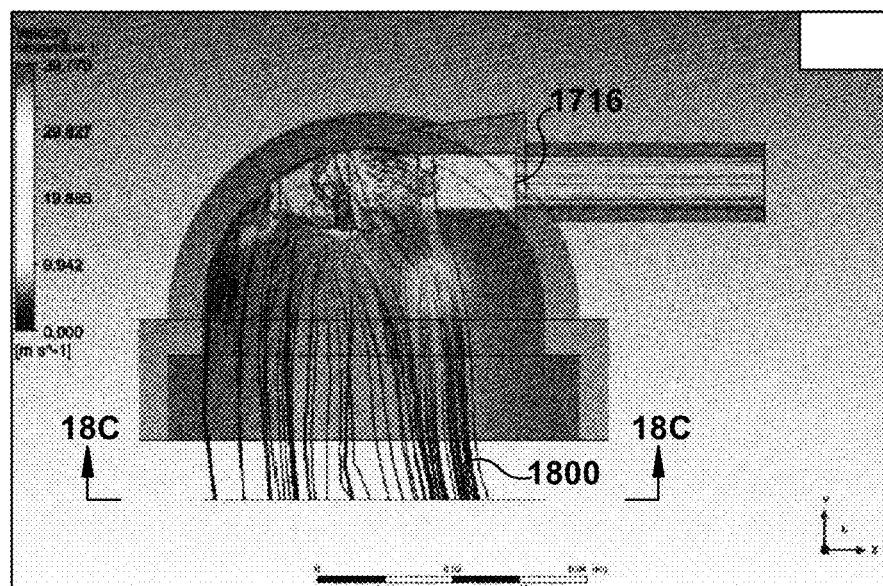
FIGS. 18A-18C illustrate various flow trajectories and distributions for the sieve bed cap embodiment of FIGS. 17A-17I.
Figure 18B:
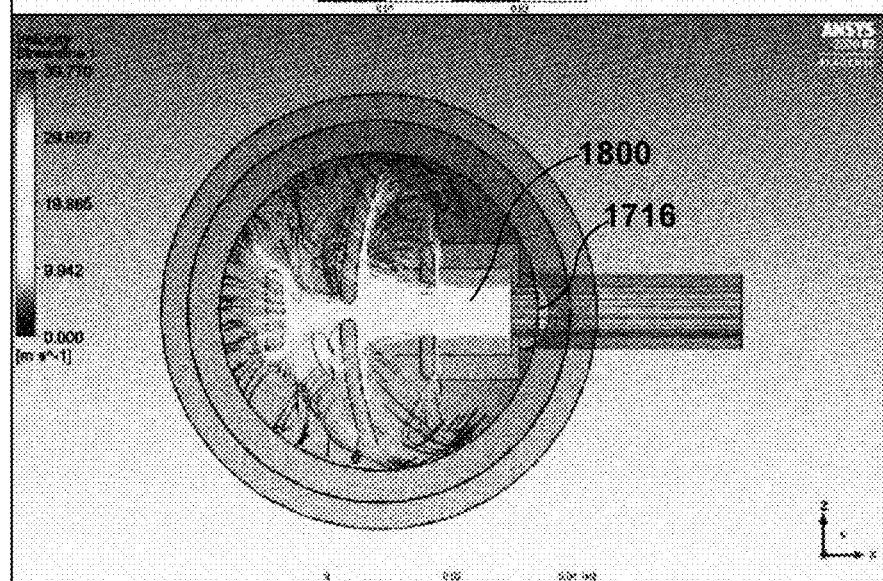
Figure 18C:
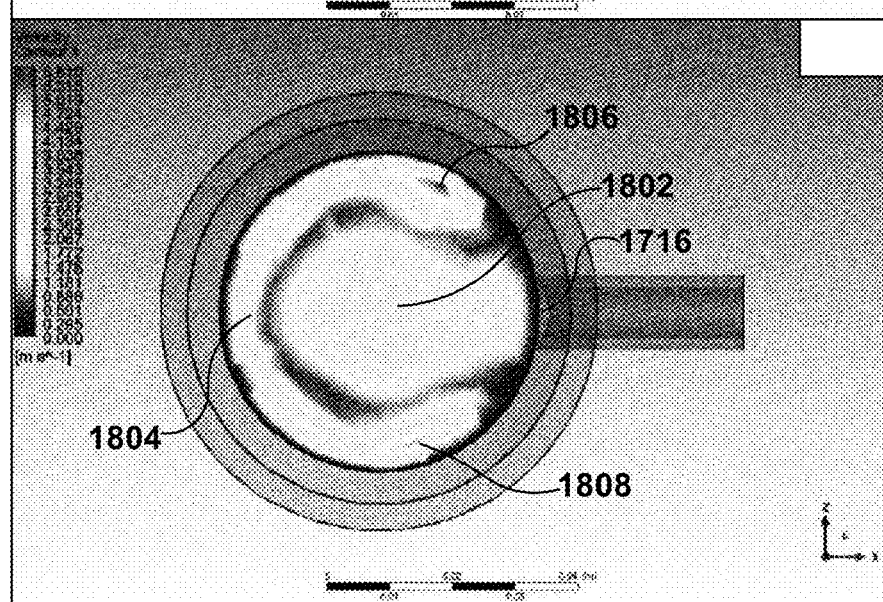

FIGS. 18A-18C illustrate the flow distribution and velocities generated by the structures, partitions, and/or projections of the cap/interface of FIGS. 17A-17I as modeled by computational fluid dynamics software by Ansys, Inc. FIG. 18A shows a cross-sectional view similar to FIG. 17B with the resulting computed flow streams 1800 channeled within the cap/interface and their velocities shown along the x and y axis direction. FIG. 18B shows a bottom view similar to FIG. 17A and with the resulting computed flow streams 1800 and their velocities shown along the x and z axis direction. In FIGS. 18A and 18B, the velocities are indicated as higher to lower as shading goes from light to dark for the flow streams 1800.

FIG. 18C illustrates the resulting computed flow and/or velocity distribution at the planar location indicated in FIG. 18A, which is proximate the face of the sieve bed material and/or diffuser (e.g., 510). Thus, FIG. 18C represents the computed flow distribution and velocities at or near the face of the sieve bed material. As shown, the flow distribution includes a relatively large substantially uniform distribution of flow region 1802 from the center and extending outwards. A second smaller region 1804 having an arc shape is also present having substantially uniform flow distribution. Similar to FIGS. 18A and 18B, the velocities are indicated as higher to lower as shading goes from light to dark. Two exceptions are small regions 1806 and 1808, where these dark regions represent higher than average flow velocities. With the exception of very small regions 1806 and 1808, an optimized and substantially uniform flow distribution of gas representing approximately 70-80% (or more) of the area proximate the face of the sieve bed material is obtained. This uniformity makes the sieve beds more efficient by more uniformly introducing the gas into the sieve bed material to thereby limit or eliminate pockets of sieve material that the gas may not otherwise reach when the gas is non-uniformly distributed as it enters the sieve bed material.

Figure 18D:
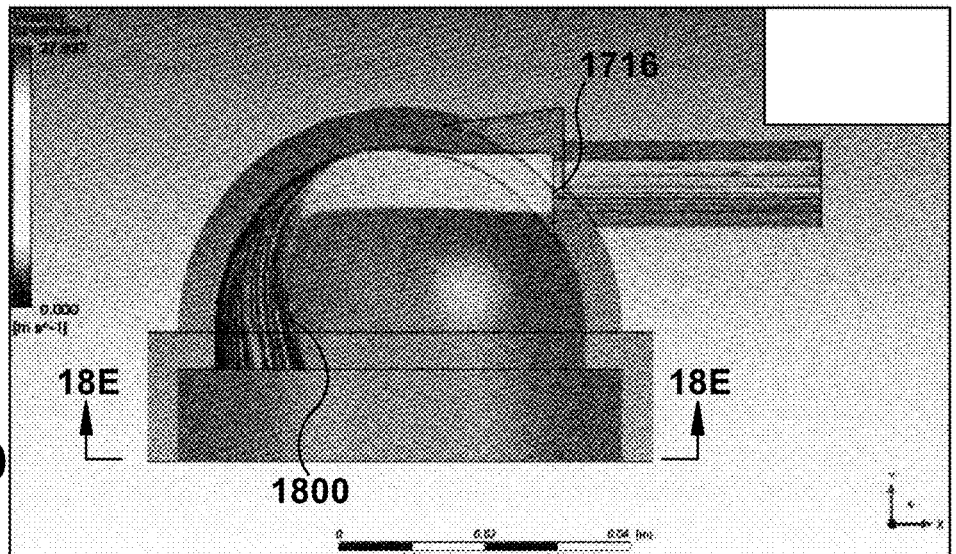
FIGS. 18D-18E illustrate various flow trajectories and distributions for the sieve bed cap embodiment of FIGS. 17A-17I, but absent any flow modifying structures.
Figure 18E:
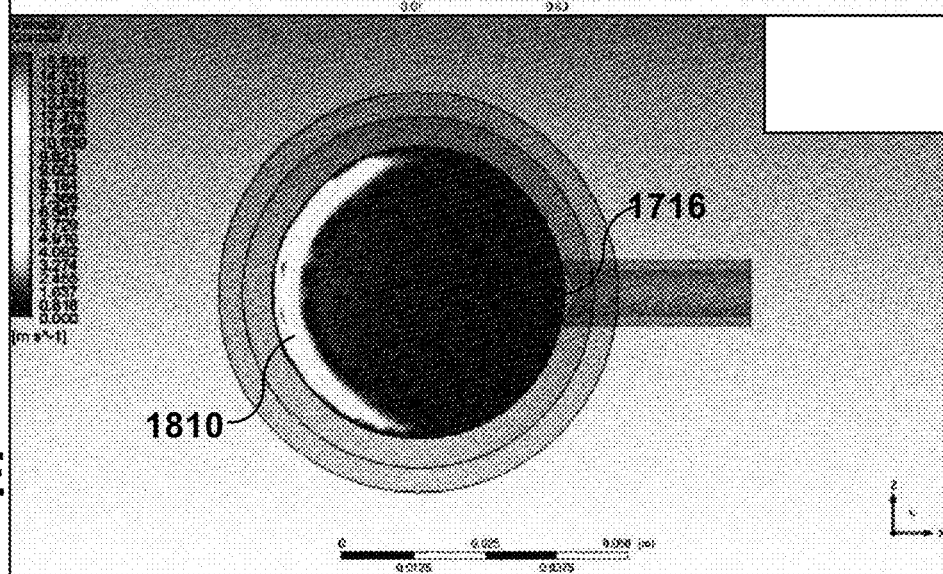

For reference, FIGS. 18D and 18E illustrate the flow distribution and velocities of the cap/interface of FIGS. 17A-17I but absent any flow modifying structures, partitions, and/or projections. As seen in FIG. 18D, the flow stream 1800 is not uniformly distributed within the cap's internal chamber. And, as seen in FIG. 18E, the resulting flow distribution is concentrated along a narrow arc 1810 along the internal chamber boundary wall opposite gas port 1716. This non-uniform flow distribution generates undesirable higher flow velocities and/or required pressures that contribute to sieve bed wear and tear including dusting and fluidization of the sieve material, wear of filter media, compressor wear (over time) etc.

Figure 19A:
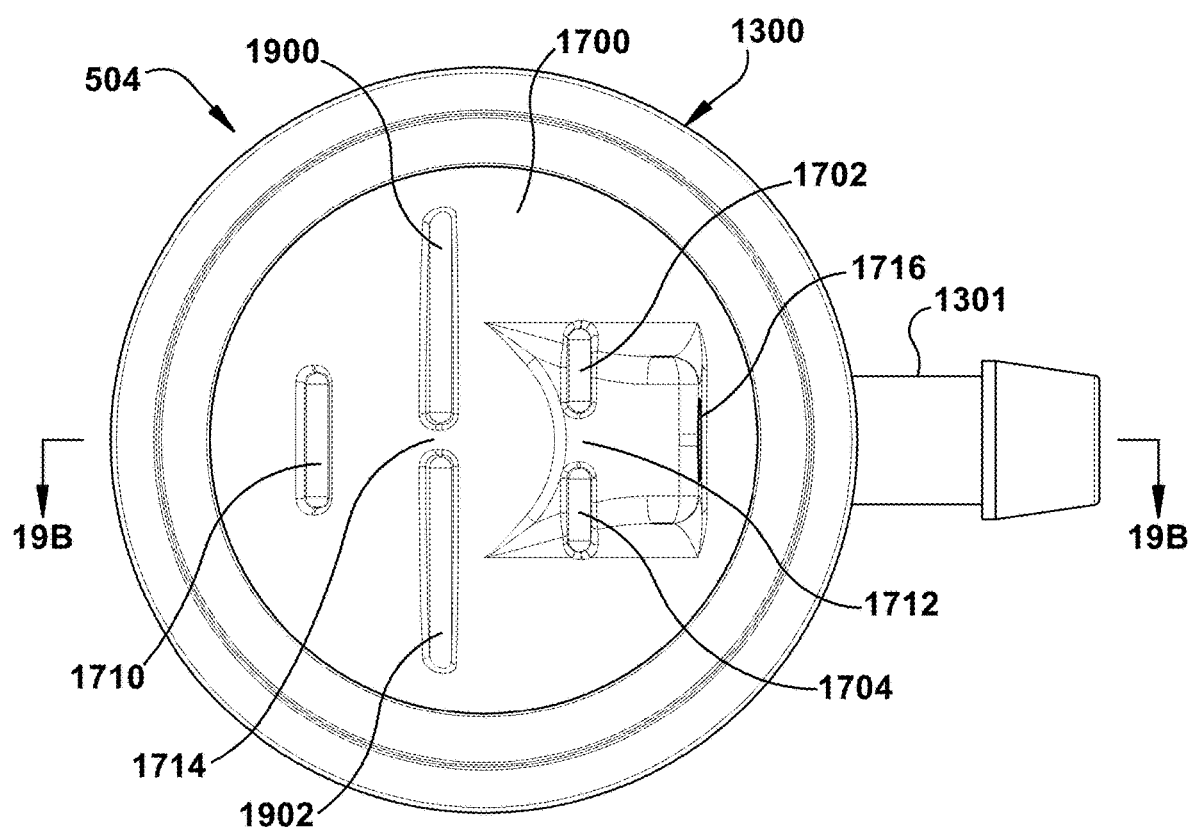
FIGS. 19A-19B illustrate another embodiment of a sieve bed cap for generating a desired flow profile.
Figure 19B:
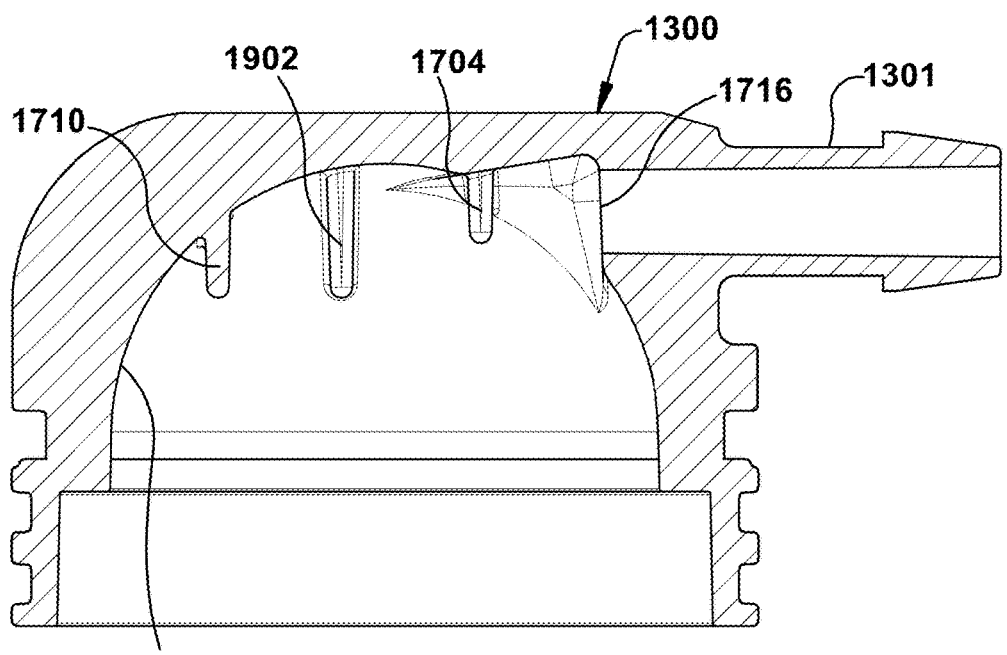

FIGS. 19A and 19B illustrate another embodiment of a sieve bed cap/interface 504 having flow modifying structures. The embodiment of FIGS. 19A and 19B is similar to that of FIGS. 17A-17I, except that second flow modifying structures 1900 and 1902 are not curved (vis-à-vis second flow modifying structures 1706 and 1708 of FIGS. 17A-17I, which are shown curved). As illustrated, second flow modifying structures 1900 and 1902 have substantially flat bodies with rounded or curved end faces. Other than this difference, the embodiments of FIGS. 17A-17I and FIGS. 19A-19B are similar (including the flow patterns; see FIG. 20B) and the corresponding descriptions are hereby incorporated by reference.

Figure 20A:
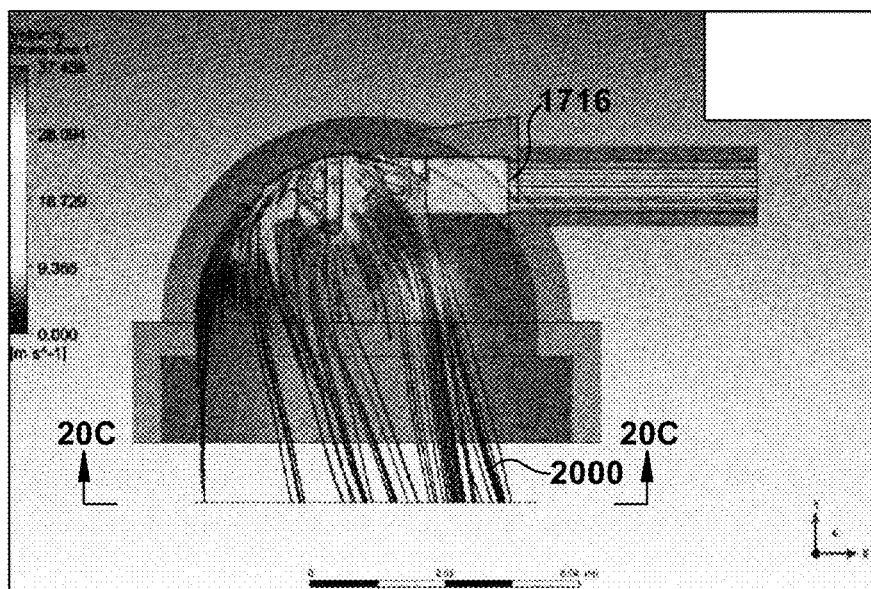
FIGS. 20A-20C illustrate various flow trajectories and distributions for the sieve bed cap embodiment of FIGS. 19A-19C.
Figure 20B:
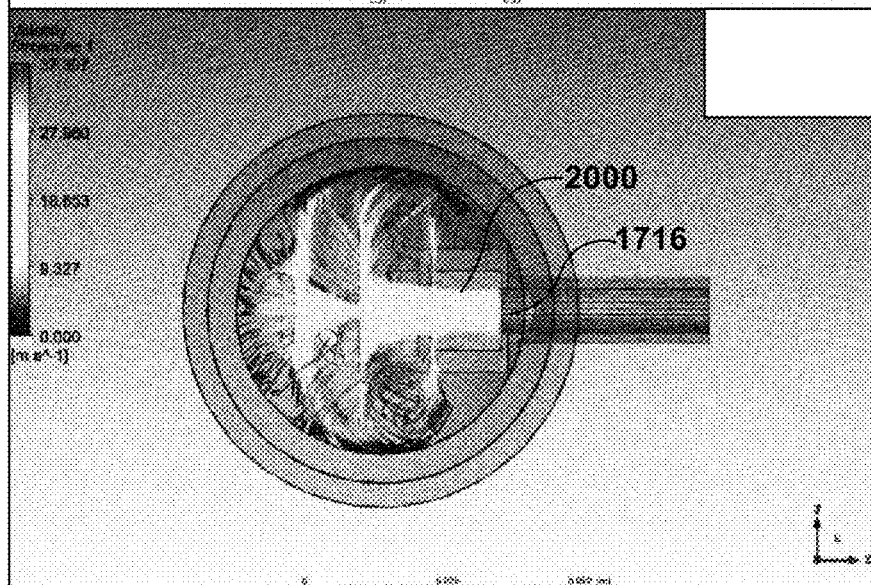
Figure 20C:
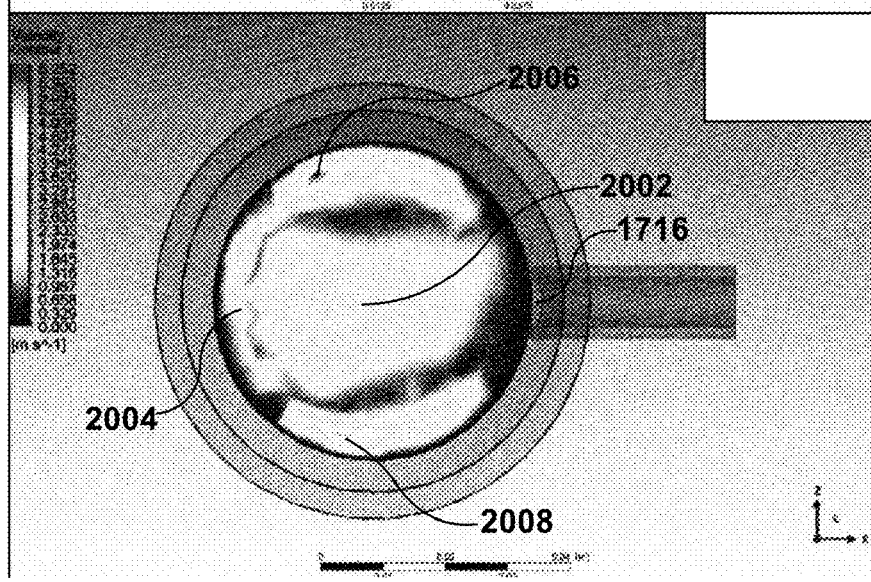
Figure 21A:
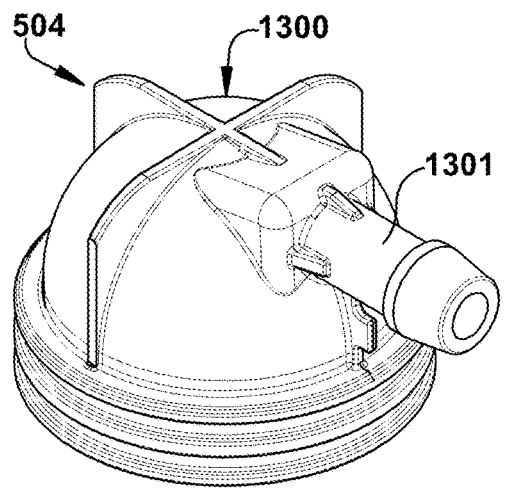
FIGS. 21A-21D illustrate various views of another embodiment of a sieve bed cap for generating a desired flow profile.
Figure 21B:
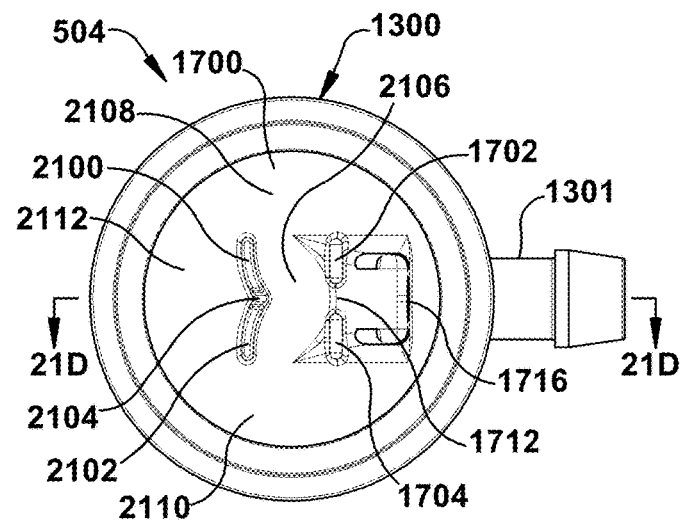
Figure 21C:
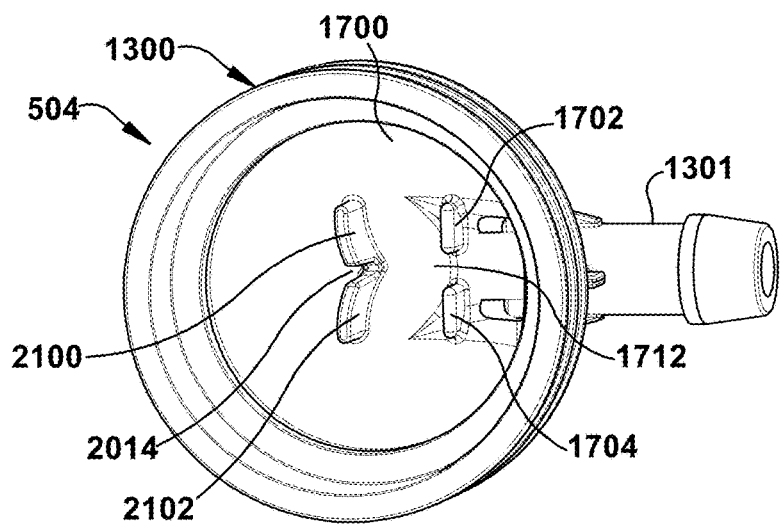
Figure 21D:
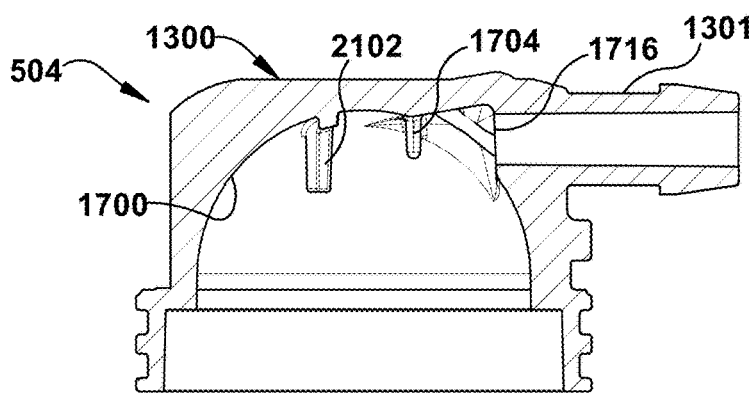
Figure 22A:
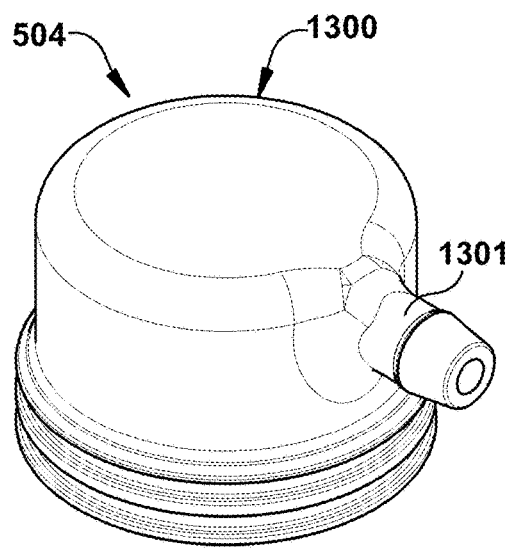
FIGS. 22A-22D illustrate various views of another embodiment of a sieve bed cap for generating a desired flow profile.
Figure 22B:
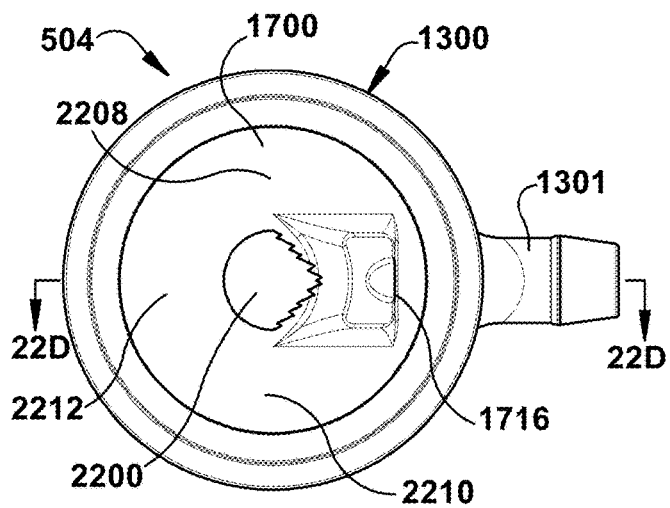
Figure 22C:
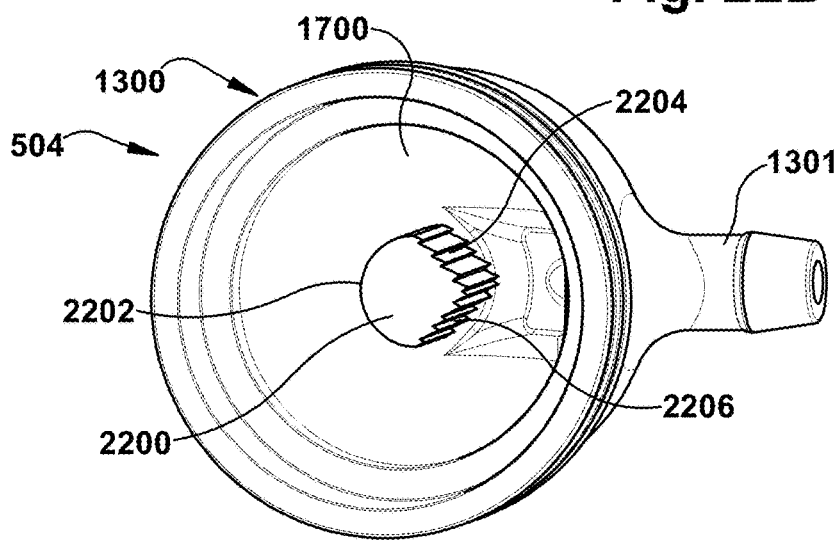
Figure 22D:
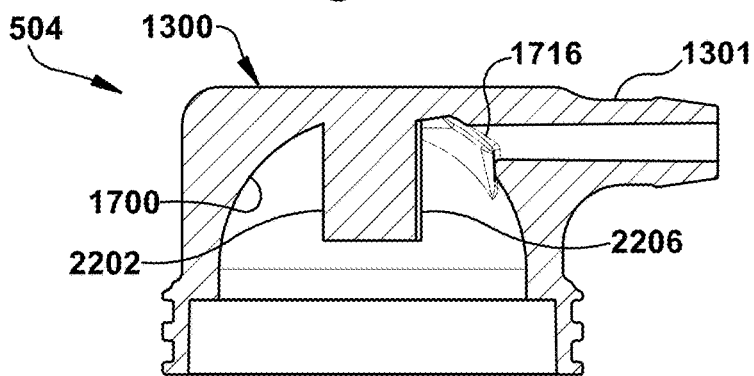
Figure 23A:
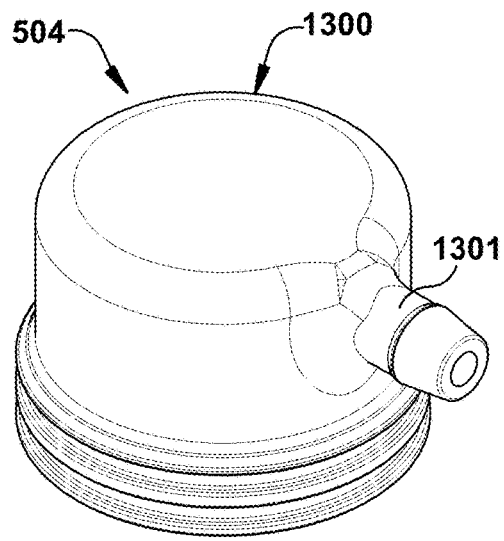
FIGS. 23A-23D illustrate various views of another embodiment of a sieve bed cap for generating a desired flow profile.
Figure 23B:
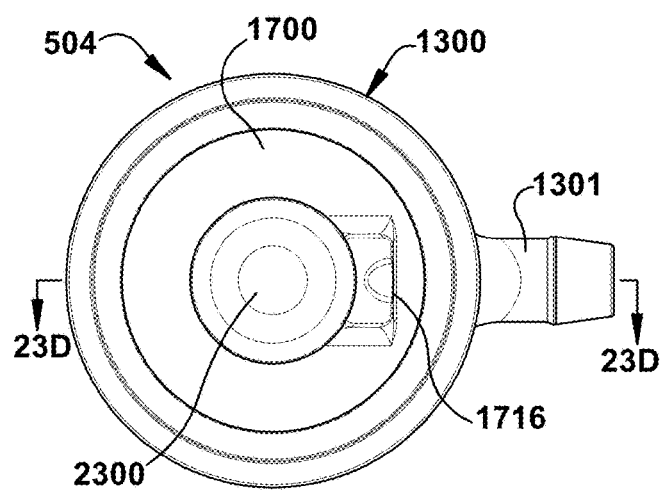
Figure 23C:
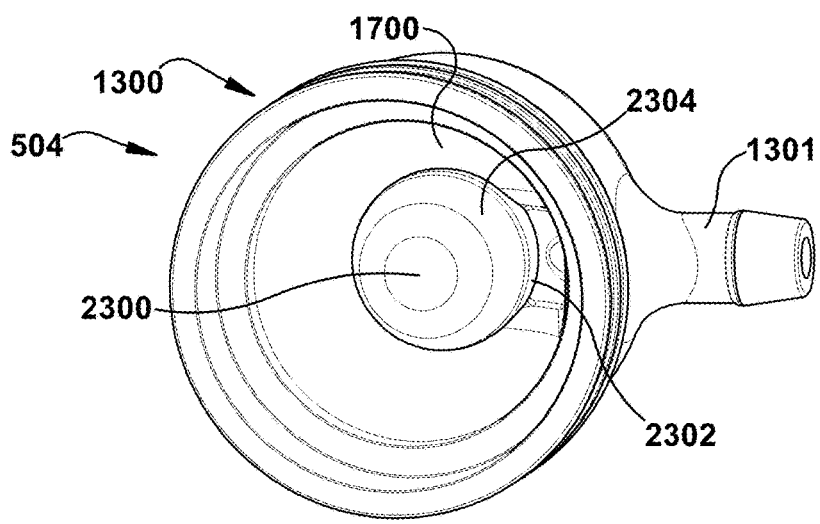
Figure 23D:
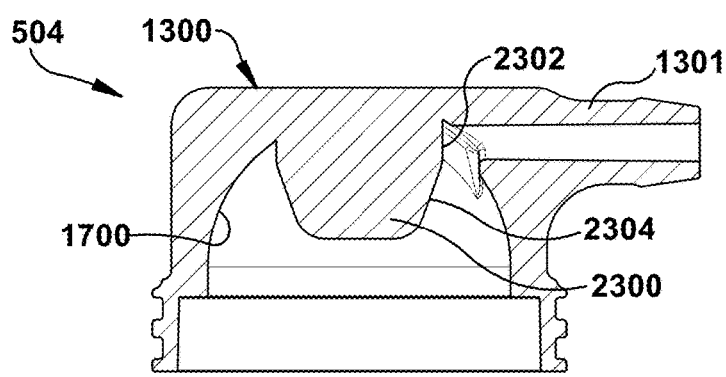
Figure 24A:
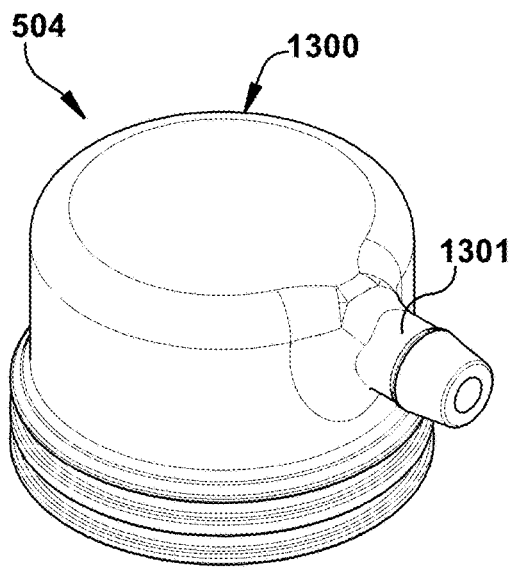
FIGS. 24A-24D illustrate various views of another embodiment of a sieve bed cap for generating a desired flow profile.
Figure 24B:
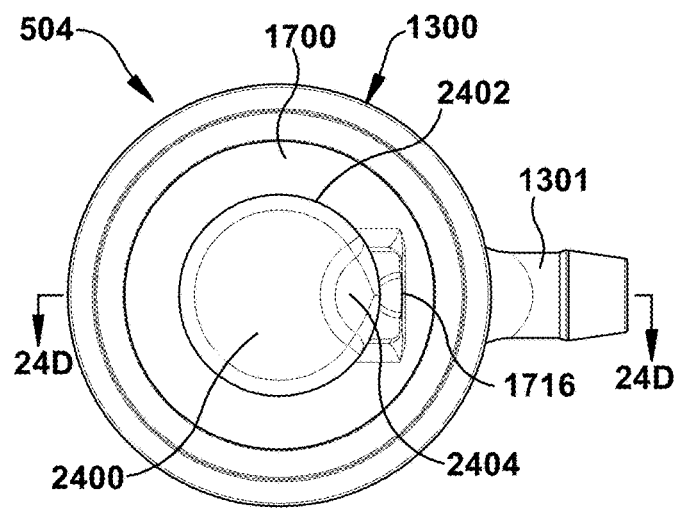
Figure 24C:
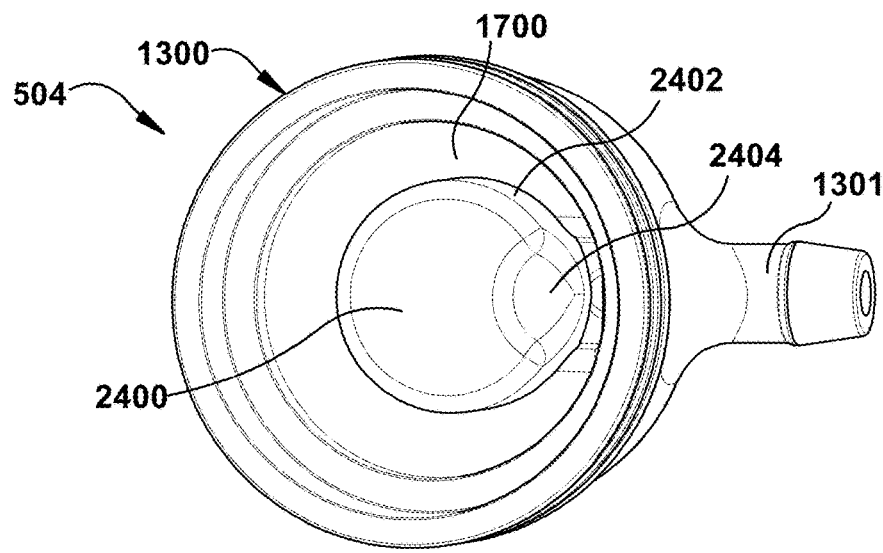
Figure 24D:
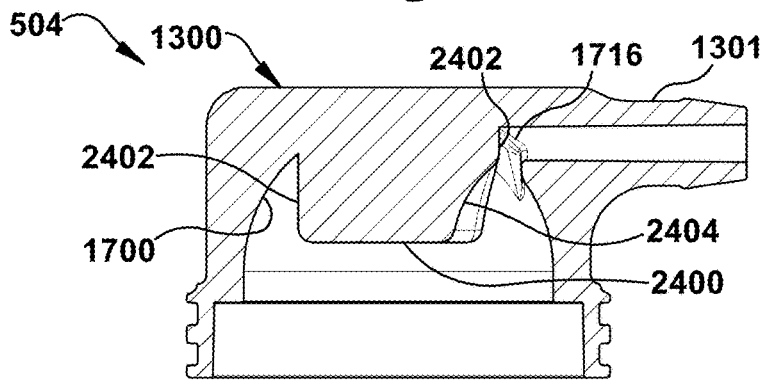

FIGS. 20A-20C illustrate the flow distribution and velocities generated by the structures, partitions, and/or projections of the cap/interface of FIGS. 19A-19B as modeled by computational fluid dynamics software by Ansys, Inc. Thus, the same analysis as shown and described in FIGS. 18A-18C was performed for the embodiment of FIGS. 19A-19B. FIG. 20A shows a cross-sectional view similar to FIG. 19B and with the resulting computed flow streams 2000 channeled within the cap/interface and their velocities shown along the x and y axis direction. FIG. 20B shows a bottom view similar to FIG. 19A and with the resulting computed flow streams 1800 and their velocities shown along the x and z axis direction. In FIGS. 20A and 20B, the velocities are indicated as higher to lower as shading goes from light to dark for the flow streams 2000.

FIG. 20C illustrates the resulting computed flow and/or velocity distribution at the planar location indicated in FIG. 20A, which is proximate the face of the sieve bed material and or diffuser (e.g., 510). Thus, FIG. 20C represents the computed flow distribution and velocities near the face of the sieve bed material. As shown, the flow distribution includes a relatively large substantially uniform distribution of flow region 2002 from the center and extending outwards. A second smaller region 2004 with a slightly disrupted arc shape is also present having substantially uniform flow distribution. Similar to FIGS. 20A and 20B, the velocities are indicated as higher to lower as shading goes from light to dark. Two exceptions are small regions 2006 and 2008, where these dark regions represent higher than average flow velocities. With the exception of very small regions 2006 and 2008, an optimized and substantially uniform flow distribution of gas representing approximately 70-80% (or more) of the area proximate the face of the sieve bed material is obtained. As previously described, this uniformity makes the sieve beds more efficient by more uniformly introducing the gas into the sieve bed material to thereby limit or eliminate pockets of sieve material that the gas may not otherwise reach when the gas is non-uniformly distributed as it enters the sieve bed material.

In addition to being more uniform in distribution, which assists in sieve bed efficiency, the flow velocities according to these embodiments are generally lower than otherwise provided. The lower flow velocities reduce dusting, fluidization, and other wear and tear on the sieve bed and the sieve bed material. This prolongs the life of the sieve beds and thereby the gas concentrating system.

FIGS. 21A-21D illustrate another embodiment of a sieve bed cap/interface 504 having flow modifying structures. This embodiment includes two rows of flow modifying structures. The first row is the same as that of the embodiment of FIGS. 17A-17I and includes first flow modifying structures 1702 and 1704 and gap 1712. The second flow modifying structures are different. These include flow modifying structures 2100 and 2102 and gap 2104, which form a V shape having curved legs (e.g., 2100 and 2102) and a small gap (e.g., 2104) at the apex of the V shape. As previously described, flow modifying structures 1702 and 1704 and gap 1712 provide a first gas flow modification. Gas passing through gap 1712 enters space 2106 and encounters second flow modifying structures 2100 and 2102 and gap 2104. A portion of the gas passes through gap 2104 and another portion is deflected by structures 2100 and 2102 into spaces 2108 and 2110 where they encounter domed surface 1700. Gas passing through gap 2104 enters space 2112 where it encounters domed surface 1700. In the embodiment shown, gap 2104 is smaller than gap 1712, thereby allowing less gas to pass therethrough compared to gap 1712. In other embodiments, gap 2104 can be about 0.1 to 1.0 times the size of gap 1712. In other embodiments, gap 1712 can be correspondingly smaller than gap 2104. Thus, second flow modifying structures 2100 and 2102 and gap 2104 provide a second flow modification.

FIGS. 22A-22D illustrate another embodiment of a sieve bed cap/interface 504 having flow modifying structures. This embodiment includes a flow modifying structure 2200 having a V shape portion with stepped or undulating legs 2204 and 2206. Gas entering the internal chamber encounters the V-shaped portion and is split and deflected to spaces 2208 and 2210. However, because legs 2204 and 2206 of the V-shaped portion have stepped or undulating surfaces as shown, small portions of the gas flow are deflected back against the oncoming flow. The net result is that a portion of the gas flow is not deflected to spaces 2208 and 2210, which assists in more uniformly distributing the flow since not all of the flow is deflected to side spaces 2208 and 2210. Portions of the flow deflected to spaces 2208 and 2210 also flow into space 2212 via domed surface 1700 and cylindrical portion 2202 of the flow modifying structure 2200.

FIGS. 23A-23D illustrate another embodiment of a sieve bed cap/interface 504 having flow modifying structures. This embodiment includes a flow modifying structure 2300 that is cylindrical in nature and includes a first portion 2302 that is cylindrical and a second portion 2304 that is tapering or conical. First portion 2302 provides a first gas flow modification by deflecting gas around structure 2300 to the spaces proximate domed surface 1700. Second portion 2304, by virtue of its tapering or conical geometry, provides a second flow modification by deflecting gas flow downward to the sieve bed material. In other embodiments, second portion 2304 can be more or less tapered or conical than that shown.

FIGS. 24A-24D illustrate another embodiment of a sieve bed cap/interface 504 having flow modifying structures. This embodiment includes a flow modifying structure 2400 that is cylindrical in nature and includes first portion 2402 that is generally cylindrical and a second portion 2404 that is beveled, and which may be curved (including concave as shown and/or convex). First portion 2402 provides a first gas flow modification by deflecting gas around structure 2400 to the spaces proximate domed surface 1700. Second portion 2404, by virtue of its beveling, provides a second flow modification by deflecting gas flow downward to the sieve bed material at a region that is proximate the gas entry port 1716. In other embodiments, second portion 2404 can be more or less beveled than that shown.

Figure 25A:
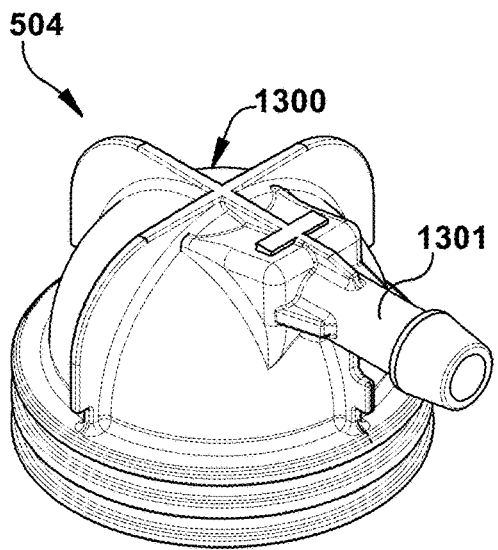
FIGS. 25A-25D illustrate various views of another embodiment of a sieve bed cap for generating a desired flow profile.
Figure 25B:
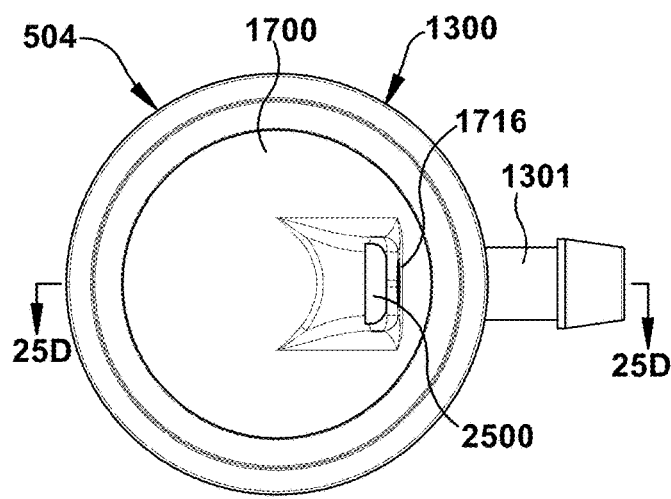
Figure 25C:
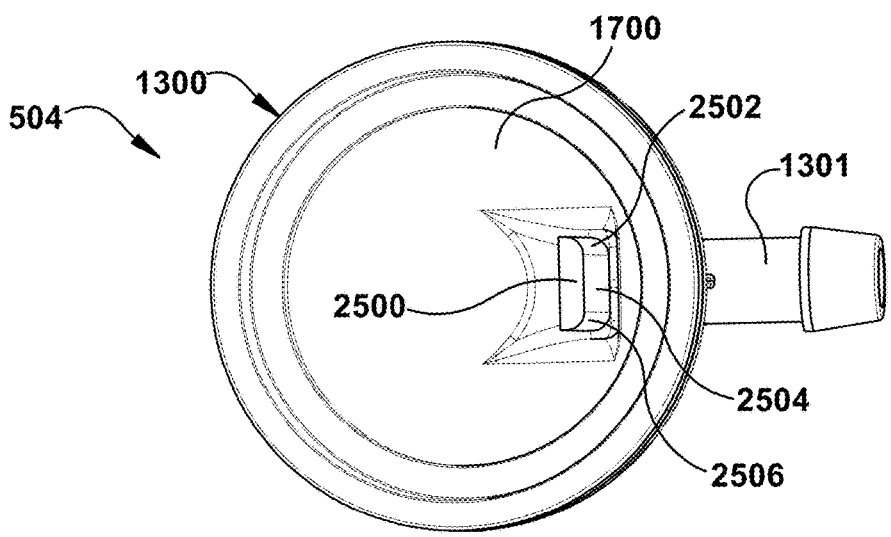
Figure 25D:
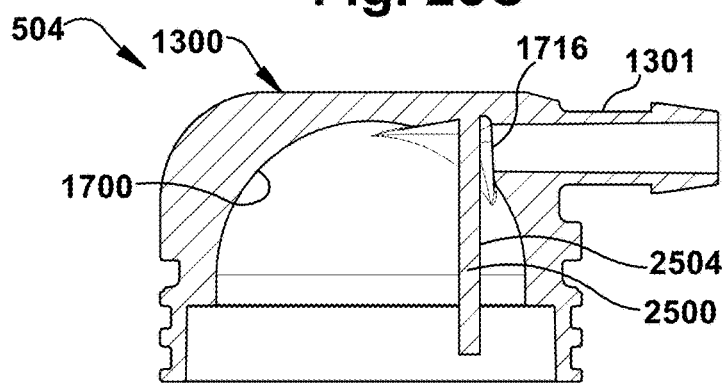

FIGS. 25A-25D illustrate another embodiment of a sieve bed cap/interface 504 having flow modifying structures. This embodiment includes a flow modifying structure 2500 that is located very near the gas entry port 1716. The reason for such close proximity to the gas entry port 1716 is to deflect the incoming gas flow stream into at least two smaller gas flow streams thereby allowing the domed surface 1700 to more uniformly distribute the flow compared to if only a single gas stream was encountering the domed surface 1700. Flow modifying structure 2500 includes a substantially flat surface 2504 with curved end surfaces 2502 and 2506, respectively, on the sides thereof. The curved end surfaces 2502 and 2506 provide a less turbulent and less noisy deflection of the gas flow stream to domed surface 1700. In other embodiments, end surfaces 2502 and 2506 do not have to be curved but can be substantially flat and angled relative to surface 2504. As shown in FIG. 25D, flow modifying structure 2500 can extend down significantly into the internal chamber of the sieve bed cap/interface. In other embodiments, it can extend less than that shown including, for example, only up to or just beyond the perimeter of the gas entry port 1716.

FIGS. 26A-26D illustrate another embodiment of a sieve bed cap/interface 504 having a cylindrical wall 2600 instead of, for example, a domed surface 1700. In this embodiment, the side and top portions of the cylindrical wall 2600 act as flow modifying structures and distribute the flow into two regions. Gas flow entering from port 1716 encounters side wall portion 2602, which divides the flow into upper and lower flow streams. The upper flow stream is then deflected by top surface 2604 and side surface portion 2606 back downward forming a second lower flow stream. The splitting of the main gas flow stream entering from gas entry port 1716 into two or more flow streams provides a more uniform flow distribution of the gas entering the sieve bed material. Surfaces 2608, 2610, 2612, and 2614 optionally expand in a stepwise manner the lower portion of the body 1300 to provide an attachment base to the sieve bed vessel wall 600 (see FIG. 6).

Figure 26A:
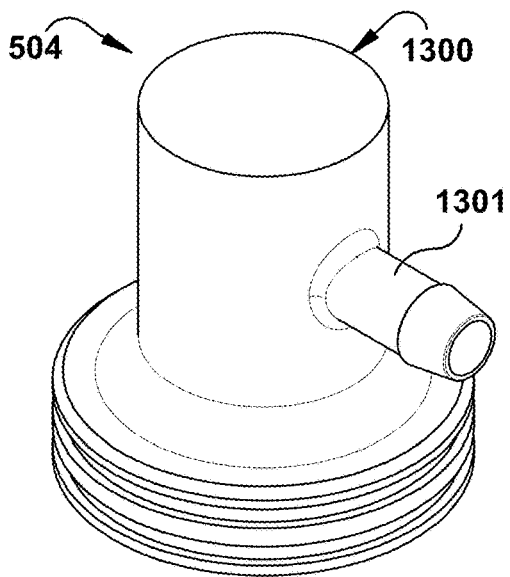
FIGS. 26A-26D illustrate various views of another embodiment of a sieve bed cap for generating a desired flow profile.
Figure 26B:
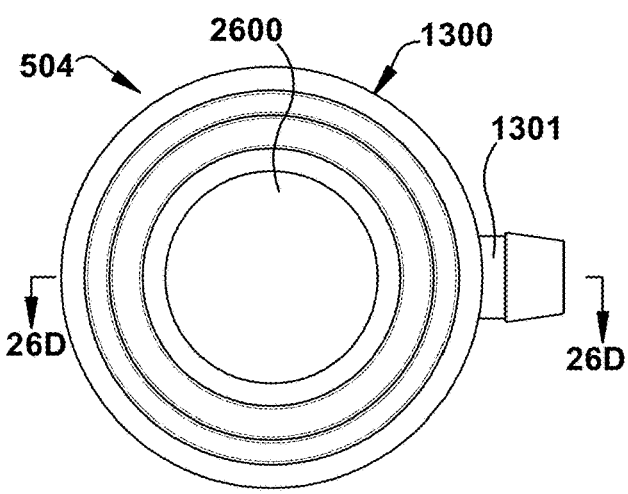
Figure 26C:
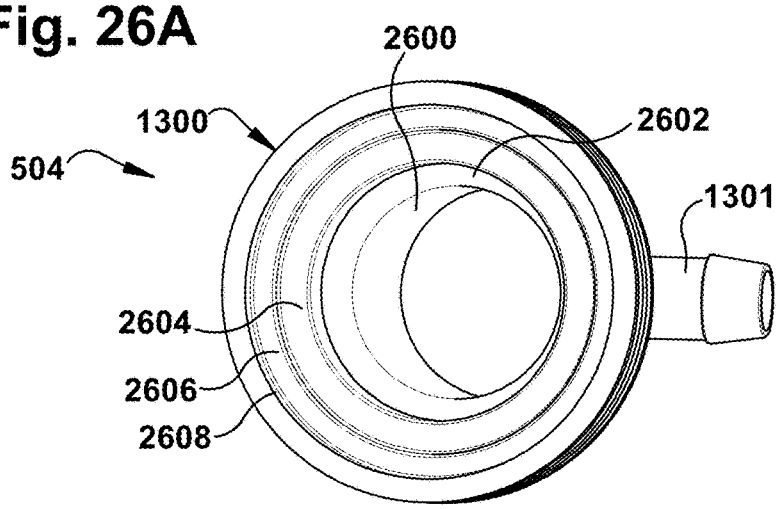
Figure 26D:
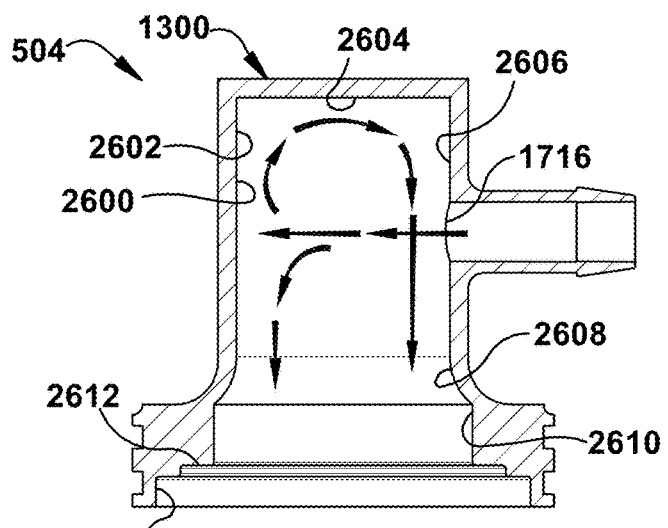
Figure 26E:
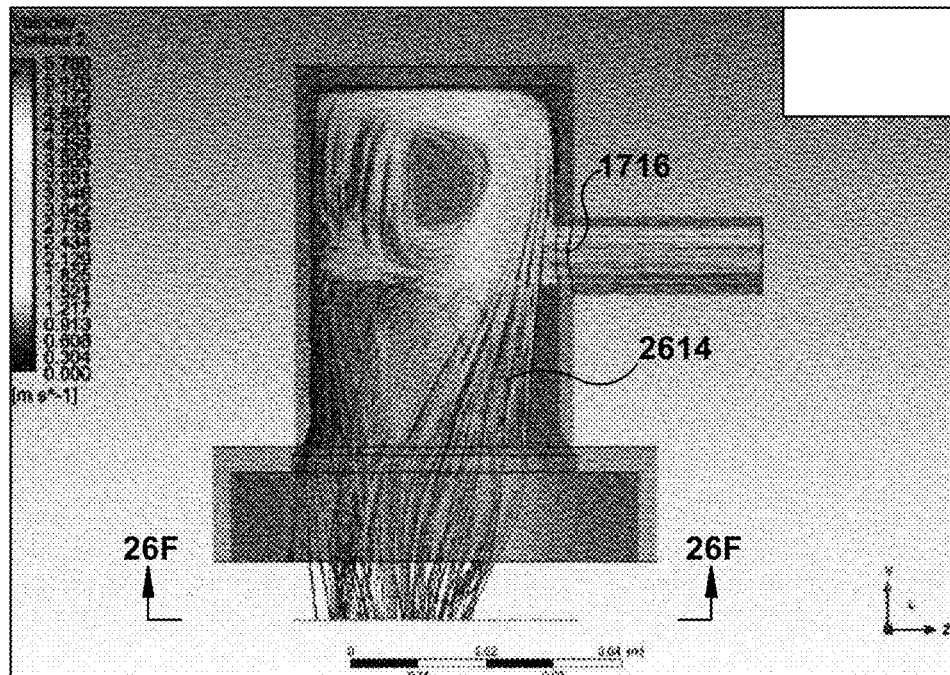
FIGS. 26E-26F illustrate various flow trajectories and distributions for the sieve bed cap embodiment of FIGS. 26A-26D.
Figure 26F:
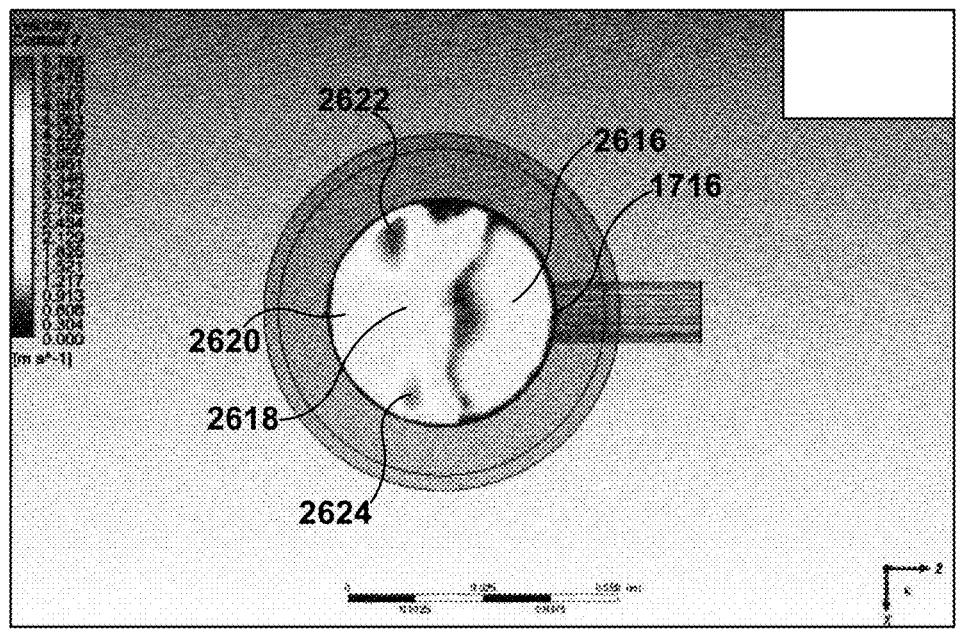

FIGS. 26E-26F illustrate the flow distribution and velocities generated by the cap/interface of FIGS. 26A-26D as modeled by computational fluid dynamics software by Ansys, Inc. Thus, the same analysis as shown and described in FIGS. 18A-18C, was performed for the embodiment of FIGS. 26A-26D. FIG. 26D shows a cross-sectional view similar to FIG. 19B and with the resulting computed flow streams 2614 channeled within the cap/interface and their velocities shown along the x and y axis direction. In FIG. 26D, the velocities are indicated as higher to lower as shading goes from light to dark for the flow streams 2000.

FIG. 26F illustrates the resulting computed flow and/or velocity distribution at the planar location indicated in FIG. 26E, which is proximate the face of the sieve bed material and/or diffuser (e.g., 510). Thus, FIG. 26E represents the computed flow distribution and velocities at the face of the sieve bed material. As shown, the flow distribution includes a substantially uniform distribution of flow region 2616. A second region 2618 of uniform flow distribution is also present. Similar to FIG. 26E the velocities are indicated as higher to lower as shading goes from light to dark. Two exceptions are small regions 2622 and 2624, where these dark regions represent higher than average flow velocities. With the exception of very small regions 2622 and 2624, an optimized and substantially uniform flow distribution of gas representing approximately 70-80% (or more) of the area proximate the face of the sieve bed material is obtained. As previously described, this uniformity makes the sieve beds more efficient by more uniformly introducing the gas into the sieve bed material to thereby limit or eliminate pockets of sieve material that the gas may not otherwise reach when the gas is non-uniformly distributed as it enters the sieve bed material.

Figure 27A:
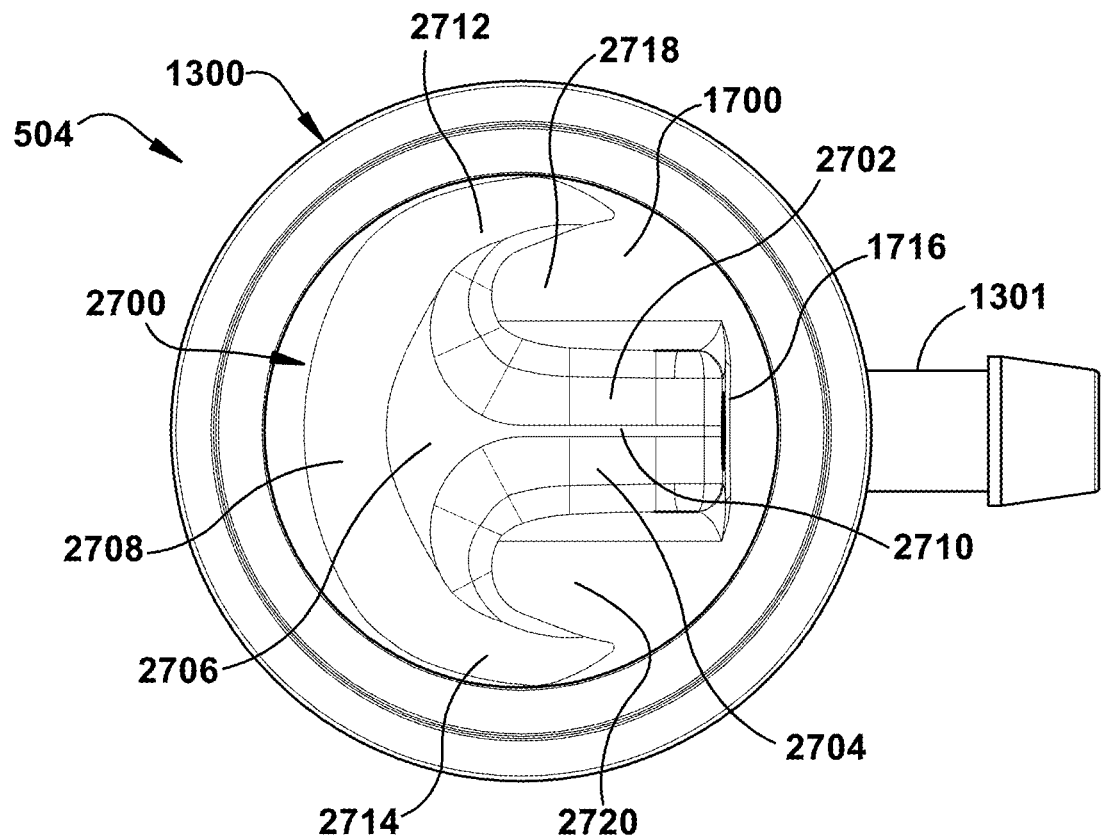
FIGS. 27A-27B illustrate various views of another embodiment of a sieve bed cap for generating a desired flow profile.
Figure 27B:
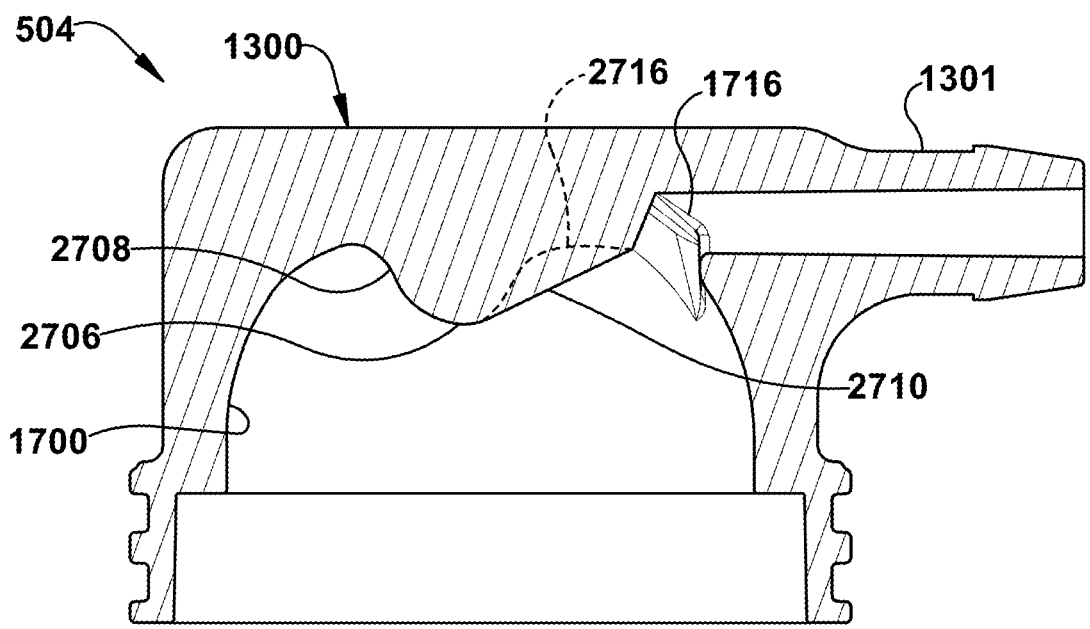

FIGS. 27A and 27B illustrate another embodiment of a sieve bed cap/interface 504 having continuous flow modifying structure 2700 instead of, for example, discrete rows or columns of structures. Structure 2700 includes several portions including curved side portions 2712 and 2714 and central portion 2706. Curved side portions 2712 and 2714 and central portion 2706 extend from dome surface 1700 and into the cap's internal chamber via curved surfaces 2702, 2704, and 2708 and surface 2710. Surface 2710 can be linear or curved (as shown via 2716) (including having multiple curves) and performs a first flow modification by splitting the incoming gas flow from port 1716 into at least two flow streams. The curved side portions 2712 and 2714 act similar to curved flow modifying structures 1706 and 1708 (e.g., FIG. 17A) by providing a second flow modification that directs a portion of the gas flow back towards spaces 2718 and 2720 where the gas flow encounters dome surface 1700 and is directed downwards toward the sieve material. This redirection provides a greater distribution of flow into the sieve bed from this region (e.g., spaces 2718 and 2720) than would have otherwise been provided thereby generating a more uniform overall flow distribution of gas entering the sieve material. While this embodiment shows a single central portion 2706 extending into the cap's internal chamber, in other embodiments central portion 2706 may be divided into several portions mimicking the low modifying structures of, for example, FIGS. 17A-21D whereby these structures can extend from dome surface 1700 by curved surfaces and are connected to each other by curved surfaces while still maintaining the same general configuration as shown in these embodiments.

The net result of the aforementioned embodiments is a more uniform flow distribution and lower flow velocities compared to a sieve bed cap 504 not having any flow modifying structures associated therewith. Additionally, the flow modifying structures of the various embodiments shown and described herein can be further combined to create additional combinations of flow modifying structures. Further, the embodiments of sieve bed caps/interfaces shown and described can be used with or without a flow diffuser, such as diffuser 510 disclosed herein. Still further, while the flow modifying structures have been shown by way of example as part of a sieve bed cap/interface, these same structures can also be implemented as a separate component, insert and/or adapter to be placed within an existing sieve bed cap/interface or mounted separately within a sieve bed assembly so as to work in conjunction with a sieve bed cap or interface. Yet further, a sieve bed cap/interface can include both anti-tamper features and flow modifying structures as disclosed herein.

While the present inventions have been illustrated by the description of embodiments thereof, and while the embodiments have been described in considerable detail, it is not the intention of the descriptions to restrict or in any way limit the scope of the disclosure to such detail. Additional advantages and modifications will readily appear to those skilled in the art. For example, the relative size, dimensions and shapes of the components can be changed without significantly affecting their functionality. Therefore, the inventions, in their broader aspects, are not limited to the specific details, the representative apparatus, and illustrative examples shown and described. Accordingly, departures can be made from such details without departing from the spirit or scope of the general inventive concepts.

What is claimed:

1. An anti-tamper cap for a sieve bed comprising:
   a body comprising:
   an interior surface and an exterior surface;
   the interior surface forming at least part of a gas receiving chamber; and
   the exterior surface including:
      at least first and second projecting members; and
      a space partially enclosed by the first and second projecting members; and
   wherein the second projecting member extends around the body and the first projecting member extends partially around the body.

2. The cap of claim 1, wherein the first projecting member comprises at least one vertically oriented rib.

3. The cap of claim 1, wherein the first projecting member comprises a plurality of vertically oriented ribs.

4. The cap of claim 1, wherein the cap body comprises a revolved dome having the at least one projecting member.

5. The cap of claim 1, wherein the cap body comprises a plurality of first projecting members and a plurality of spaces.

6. The cap of claim 1, wherein the first projecting member comprises a vertically oriented tab.

7. An anti-tamper cap for a sieve bed comprising:
   a body including an interior surface forming at least part of a gas receiving chamber and an exterior surface comprising at least first and second projecting members and a recess between the first and second projecting members;
   wherein the second projecting member extends around a perimeter of the body and the first projecting member extends partially around the perimeter of the body.

8. The cap of claim 7 wherein the at least first projecting member comprises a vertically oriented rib extending outwardly from the body.

9. The cap of claim 7 wherein the at least first projecting member provides a visual tamper indication when damaged.

10. An anti-tamper cap for a sieve bed comprising:
    a body including an interior surface forming at least part of a gas receiving chamber and an exterior surface comprising at least first and second projecting members and a recess formed by a space between the first and second projecting members;

wherein the second projecting member extends horizontally around the body and the first projecting member extends vertically from the body and partially around of the body.

11. The cap of claim 10 wherein the at least first projecting member comprises a vertically oriented rib extending outwardly from the body.

12. The cap of claim 10 wherein the at least first projecting member provides a visual tamper indication when damaged.

13. The cap of claim 1 wherein the body further comprises a gas flow port comprising a first opening in the interior surface and second opening in the exterior surface and a passageway between the first and second openings.

14. The cap of claim 7 wherein the body further comprises a gas flow port comprising a first opening in the interior surface and second opening in the exterior surface and a passageway between the first and second openings.

15. The cap of claim 10 wherein the body further comprises a gas flow port comprising a first opening in the interior surface and second opening in the exterior surface and a passageway between the first and second openings.

16. The cap of claim 1 wherein the first projecting member comprises an untampered state having a first geometry and a tampered state having a second geometry.

17. The cap of claim 7 wherein the first projecting member comprises an untampered state having a first geometry and a tampered state having a second geometry.

18. The cap of claim 10 wherein the first projecting member comprises an untampered state having a first geometry and a tampered state having a second geometry.

19. The cap of claim 1 wherein the first projecting member comprises an edge, an untampered state having the edge in a first geometry, and a tampered state having the edge in a second geometry.

20. The cap of claim 7 wherein the first projecting member comprises an edge, an untampered state having the edge in a first geometry, and a tampered state having the edge in a second geometry.

* * * * *